United States Patent
Mosrin et al.

(10) Patent No.: US 10,021,877 B2
(45) Date of Patent: Jul. 17, 2018

(54) SUBSTITUTED 5-HYDROXY-2,3-DIPHENYLPENTANONITRILE DERIVATIVES, PROCESSES FOR THEIR PREPARATION AND THEIR USE AS HERBICIDES AND/OR PLANT GROWTH REGULATORS

(71) Applicant: BAYER CROPSCIENCE AKTIENGESELLSCHAFT, Monheim am Rhein (DE)

(72) Inventors: Marc Mosrin, Frankfurt am Main (DE); Harald Jakobi, Frankfurt (DE); Hansjoerg Dietrich, Liederbach am Taunus (DE); Elmar Gatzweiler, Bad Nauheim (DE); Christopher Rosinger, Hofheim (DE); Dirk Schmutzler, Hattersheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 57 days.

(21) Appl. No.: 14/895,343

(22) PCT Filed: Jun. 2, 2014

(86) PCT No.: PCT/EP2014/061328
§ 371 (c)(1),
(2) Date: Dec. 2, 2015

(87) PCT Pub. No.: WO2014/195253
PCT Pub. Date: Dec. 11, 2014

(65) Prior Publication Data
US 2016/0113277 A1   Apr. 28, 2016

(30) Foreign Application Priority Data
Jun. 7, 2013   (EP) .................... 13171035

(51) Int. Cl.
| | | |
|---|---|---|
| *A01N 37/36* | (2006.01) | |
| *A01N 37/34* | (2006.01) | |
| *C07C 255/37* | (2006.01) | |
| *C07C 255/36* | (2006.01) | |
| *C07C 253/30* | (2006.01) | |
| *C07C 255/53* | (2006.01) | |
| *A01N 53/00* | (2006.01) | |

(52) U.S. Cl.
CPC ............ *A01N 37/36* (2013.01); *A01N 37/34* (2013.01); *A01N 53/00* (2013.01); *C07C 253/30* (2013.01); *C07C 255/36* (2013.01); *C07C 255/37* (2013.01); *C07C 255/53* (2013.01)

(58) Field of Classification Search
None
See application file for complete search history.

(56) References Cited

U.S. PATENT DOCUMENTS

| | | | |
|---|---|---|---|
| 4,224,052 A | | 9/1980 | Szucs |
| 4,443,246 A | * | 4/1984 | Kawamatsu ........... A01N 47/30 504/244 |
| 2014/0087945 A1 | | 3/2014 | Jakobi et al. |
| 2014/0194291 A1 | | 7/2014 | Jakobi et al. |

FOREIGN PATENT DOCUMENTS

| | | | |
|---|---|---|---|
| EP | 0005341 A2 | 11/1979 | |
| EP | 0266725 A1 | 5/1988 | |
| EP | 0270830 A1 | 6/1988 | |
| FR | 2561918 A1 * | 10/1985 | ........... A61K 31/365 |
| WO | 2011003775 A2 | 1/2011 | |
| WO | 2011003776 A2 | 1/2011 | |
| WO | 2011042378 A1 | 4/2011 | |
| WO | 2011073143 A1 | 6/2011 | |
| WO | 2012126764 A1 | 9/2012 | |
| WO | 2012126765 A1 | 9/2012 | |
| WO | 2013010882 A2 | 1/2013 | |

OTHER PUBLICATIONS

Axiotis, Stella; et. al. "Tetrahydropyran-2-ones. I. Synthesis and pharmacological activity" 1981, 16(5), 431-438. (Year: 1981).*
International Search Report and Written Opinion from corresponding PCT/EP2014/061328, dated Jul. 16, 2014.

* cited by examiner

*Primary Examiner* — Mina Haghighatian
*Assistant Examiner* — Erin Hirt
(74) *Attorney, Agent, or Firm* — McBee Moore Woodward & Vanik IP, LLC

(57) ABSTRACT

Primarily, the present invention relates to the use of substances of the formula (I) as herbicides, in particular for controlling broad-leaved weeds and/or weed grasses in crops of useful plants and/or as plant growth regulators for influencing the growth of crops of useful plants. The invention furthermore relates to the novel herbicidal substances of the formulae (Ib) and (Ia). The present invention also relates to corresponding compositions comprising one or more of the herbicides of the formula (I) and further agrochemically active substances, and also to plant growth-regulating or herbicidal compositions comprising one or more of these compounds. Moreover, the present invention relates to processes for preparing the compounds of the formula (I).

7 Claims, No Drawings

SUBSTITUTED 5-HYDROXY-2,3-DIPHENYLPENTANONITRILE DERIVATIVES, PROCESSES FOR THEIR PREPARATION AND THEIR USE AS HERBICIDES AND/OR PLANT GROWTH REGULATORS

CROSS REFERENCE TO RELATED APPLICATIONS

This application is a § 371 National Stage Application of PCT/EP2014/061328, filed 2 Jun. 2014, which claims priority to EP 13171035.2, filed 7 Jun. 2013.

BACKGROUND

Field of the Invention

Primarily, the present invention relates to the use of substances of the formula (I) defined below as herbicides, in particular for controlling broad-leaved weeds and/or weed grasses in crops of useful plants and/or as plant growth regulators for influencing the growth of crops of useful plants. The invention furthermore relates to the novel herbicidal substances of the formulae (Ib) and (Ia) defined below. The present invention also relates to corresponding compositions comprising one or more of the herbicides of the formula (I) and further agrochemically active substances, and also to plant growth-regulating or herbicidal compositions comprising one or more of these compounds. Moreover, the present invention relates to processes for preparing the compounds of the formula (I).

Description of Related Art

In their application, crop protection agents known to date for the selective control of harmful plants in crops of useful plants or active compounds for controlling unwanted vegetation sometimes have disadvantages, be it (a) that they have no or else insufficient herbicidal activity against particular harmful plants, (b) that the spectrum of harmful plants which can be controlled with an active compound is not wide enough, (c) that their selectivity in crops of useful plants is too low and/or (d) that they have a toxicologically unfavourable profile. Furthermore, some active compounds which can be used as plant growth regulators for a number of useful plants cause unwanted reduced harvest yields in other useful plants or are not compatible with the crop plant, or only within a narrow application rate range. Some of the known active compounds cannot be produced economically on an industrial scale owing to precursors and reagents which are difficult to obtain, or they have only insufficient chemical stabilities. In the case of other active compounds, the activity is too highly dependent on environmental conditions, such as weather and soil conditions.

Herbicidal cyanobutyrates are known inter alia from the documents EP-A-0 005 341 (corresponds to U.S. Pat. No. 4,224,052), EP-A-0 266 725, EP-A-0 270 830, WO 2011/003775 A2, WO 2011/003776 A2, WO 2011/073143 A1, WO 2011/042378 A1, WO 2012/126764 A1 and WO 2012/126765 A1.

EP-A-0 005 341 describes herbicidal esters and amides of 4-cyano-3,4-diphenylbutanoic acids which are optionally substituted at the phenyl radicals. According to EP-A-0 005 341, the threo isomers are generally suitable for the non-selective control of harmful plants, whereas the erythro/threo isomer mixtures are suitable for the selective control of harmful plants in some crops of useful plants. Moreover, EP-A-0 005 341 mentions that the 2 enantiomers belonging to the threo form have different activities, which was investigated in an exemplary manner on the different activities of the enantiomers of the enantiomer pair of 4-cyano-3,4-diphenylbutanoic acid unsubstituted in the phenyl radicals.

EP-A-0 266 725 discloses some erythro/threo isomer mixtures which can be used selectively for controlling weeds in rice crops.

EP-A-0 270 830 describes that threo isomers and erythro/threo isomer mixtures can be used as plant regulators, preventing the development of an infructescence in various harmful grasses.

WO 2011/003775 A2 discloses specific esters of 4-cyano-3,4-diphenylbutanoic acids which can be used as effective herbicides, preferably in crops of useful plants.

WO 2011/003776 A2, WO 2011/042378 A1, WO 2011/073143 A1, WO 2012/126764 A1 and WO 2012/126765 A1 disclose 4-cyano-3,4-diphenylbutanoic acids and esters which have specific substitutions at the phenyl radicals and can be used as effective herbicides, preferably also in crops of useful plants.

WO 2013/010882 describes 2,3-diphenylvaleronitrile derivatives and their use as herbicides and plant growth regulators.

The herbicidal activity of these known compounds, in particular at low application rates, and/or their compatibility with crop plants remain deserving of improvement.

For the reasons stated, there is still a need for potent herbicides and/or plant growth regulators for the selective use in crop plants or the use on non-crop land, where these active compounds preferably should have further advantageous properties in application, for example with respect to their compatibility with crop plants.

SUMMARY

It is the primary object of the present invention to provide compounds having herbicidal activity (herbicides) which are highly effective against economically important harmful plants even at relatively low application rates and can be used selectively in crop plants, preferably with good activity for harmful plants, and at the same time preferably have good compatibility with crop plants. Preferably, these herbicidal compounds should be particularly effective and efficient against a broad spectrum of weeds and preferably also have good activity against a large number of weeds.

Surprisingly, it has now been found that this object is achieved by the compounds of the formula (I) defined below and their salts.

Accordingly, the present invention primarily relates to the use of one or more compounds of the formula (I) and/or their salts,

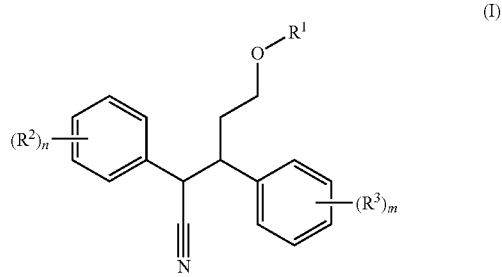

in which $R^1$ represents hydrogen or a hydrolyzable radical, $(R^2)_n$ represents n substituents $R^2$, where $R^2$ (if n=1) or each of the substituents $R^2$ (if n is greater than 1) independently of the others represents halogen, cyano, nitro, $(C_1\text{-}C_8)$-alkyl, $(C_1\text{-}C_8)$-alkoxy, $(C_1\text{-}C_8)$-alkylthio, $(C_1\text{-}C_8)$-alkylsulphinyl, $(C_1\text{-}C_8)$-alkylsulphonyl, $(C_1\text{-}C_6)$-haloalkyl, $(C_2\text{-}C_6)$-haloalkenyl, $(C_1\text{-}C_6)$-haloalkoxy, $(C_1\text{-}C_6)$-haloalkylthio, $(C_1\text{-}C_6)$-haloalkylsulphinyl, $(C_1\text{-}C_6)$-haloalkylsulphonyl, $(C_2\text{-}C_6)$-alkenyl, $(C_2\text{-}C_6)$-alkynyl, silyl or tri-$[(C_1\text{-}C_4)$-alkyl]silyl-$(C_1\text{-}C_4)$alkyl, or in each case two groups $R^2$ directly adjacent to one another at the ring (i.e. ortho to one another) together represent a group of the formula $—Z^1\text{-}A^*\text{-}Z^2$ in which $A^*$ represents an alkylene group having 1 to 4 carbon atoms which is optionally substituted by one or more radicals selected from the group consisting of halogen, $(C_1\text{-}C_4)$-alkyl, $(C_1\text{-}C_4)$-haloalkyl, $(C_1\text{-}C_4)$-alkoxy and $(C_1\text{-}C_4)$-haloalkoxy, $Z^1$ represents a direct bond, O or S and $Z^2$ represents a direct bond, O or S, where the group $—Z^1\text{-}A^*\text{-}Z^2$ together with the carbon atoms, attached to this group, of the phenyl ring form a 5- or 6-membered ring, and $(R^3)_m$ represents m substituents $R^3$, where $R^3$ (if m=1) or each of the substituents $R^3$ (if m is greater than 1) independently of the others represents halogen, cyano, nitro, $(C_1\text{-}C_8)$-alkyl, $(C_1\text{-}C_8)$-alkoxy, $(C_1\text{-}C_8)$-alkylthio, $(C_1\text{-}C_8)$-alkylsulphinyl, $(C_1\text{-}C_8)$-alkylsulphonyl, $(C_1\text{-}C_6)$-haloalkyl, $(C_2\text{-}C_6)$-haloalkenyl, $(C_1\text{-}C_6)$-haloalkoxy, $(C_1\text{-}C_6)$-haloalkylthio, $(C_1\text{-}C_6)$-haloalkylsulphinyl, $(C_1\text{-}C_6)$-haloalkylsulphonyl, $(C_2\text{-}C_6)$-alkenyl, $(C_2\text{-}C_6)$-alkynyl, tri-$[(C_1\text{-}C_4)$alkyl]silyl, tri-$[(C_1\text{-}C_4)$alkyl]silyl-$(C_1\text{-}C_4)$alkyl or $—NR^*R^{**}$, where $R^*$ and $R^{**}$ independently of one another and independently of any further radicals $—NR^*R^{**}$ present are in each case selected from the group consisting of H, $(C_1\text{-}C_8)$-alkyl, $(C_2\text{-}C_8)$-alkenyl, $(C_2\text{-}C_8)$-alkynyl, $(C_1\text{-}C_4)$-alkoxy-$(C_1\text{-}C_4)$-alkyl, $(C_1\text{-}C_6)$-alkanoyl, $[(C_1\text{-}C_4)\text{-haloalkyl}]$-carbonyl, $[(C_1\text{-}C_4)$-alkoxy]-carbonyl, $[(C_1\text{-}C_4)$-haloalkoxy]-carbonyl, $(C_3\text{-}C_6)$-cycloalkyl, $(C_3\text{-}C_6)$-cycloalkyl-$(C_1\text{-}C_4)$-alkyl, $(C_3\text{-}C_6)$-cycloalkenyl, $(C_3\text{-}C_6)$-cycloalkenyl-$(C_1\text{-}C_4)$-alkyl, phenyl and phenyl-$(C_1\text{-}C_4)$-alkyl, where each of the $(C_3\text{-}C_6)$-cycloalkyl, $(C_3\text{-}C_6)$-cycloalkyl-$(C_1\text{-}C_4)$-alkyl, $(C_3\text{-}C_6)$-cycloalkenyl, $(C_3\text{-}C_6)$-cycloalkenyl-$(C_1\text{-}C_4)$-alkyl, phenyl and phenyl-$(C_1\text{-}C_4)$-alkyl radicals mentioned is optionally substituted in the cycle by one or more identical or different radicals $R^{bb}$, where $R^{bb}$ in each case represents halogen, $(C_1\text{-}C_4)$-alkyl, $(C_1\text{-}C_4)$-haloalkyl, $(C_1\text{-}C_4)$-alkoxy or $(C_1\text{-}C_4)$-haloalkoxy and, in the case of $(C_3\text{-}C_6)$-cycloalkyl, $(C_3\text{-}C_6)$-cycloalkyl-$(C_1\text{-}C_4)$-alkyl, $(C_3\text{-}C_6)$-cycloalkenyl, $(C_3\text{-}C_6)$-cycloalkenyl-$(C_1\text{-}C_4)$-alkyl, $R^{bb}$ may additionally represent oxo, or $NR^*R^{}$ represents a 3- to 8-membered heterocycle which, in addition to this nitrogen atom, may optionally contain one or two further ring heteroatoms selected from the group consisting of N, O and S and which is unsubstituted or substituted by one or more radicals selected from the group consisting of $(C_1\text{-}C_4)$-alkyl, $(C_1\text{-}C_4)$-haloalkyl and oxo, or where in each case two groups $R^3$ directly adjacent to one another at the ring together represent a group of the formula $—Z^3\text{-}A^{}\text{-}Z^4$ in which $A^{}$ represents an alkylene group having 1 to 4 carbon atoms which is optionally substituted by one or more radicals selected from the group consisting of halogen, $(C_1\text{-}C_4)$-alkyl, $(C_1\text{-}C_4)$-haloalkyl, $(C_1\text{-}C_4)$-alkoxy and $(C_1\text{-}C_4)$-haloalkoxy, $Z^3$ represents a direct bond, O or S and $Z^4$ represents a direct bond, O or S, where the group $—Z^3\text{-}A^{}\text{-}Z^4$ together with the carbon atoms, attached to this group, of the phenyl ring form a 5- or 6-membered ring, and n represents 0, 1, 2, 3, 4 or 5, preferably 0, 1, 2 or 3, m represents 0, 1, 2, 3, 4 or 5, preferably 0, 1, 2 or 3, as herbicides and/or plant growth regulators, preferably in crops of useful plants and/or ornamental plants.

DETAILED DESCRIPTION OF A PREFERRED EMBODIMENT

Hitherto, only very few compounds of the formula (I) have been disclosed in the prior art.

J. Med. Chem. 2005, 48, 6366-6378 discloses the synthesis of 5-fluoro-(2R*,3S*)-2,3-bis(4-hydroxyphenyl)pentanonitrile and its properties as ligand of the oestrogen receptor β. In the various preparation routes described therein, compounds of the formula (I), inter alia, were obtained as synthesis intermediates.

Organic Letters 2010, 12, 3586-3589 describes nitrophenylacetonitriles as suitable nucleophiles in enantioselective organocatalytic addition reactions which also afforded compounds of the formula (I).

The compounds of the formula (I) to be used according to the invention or the compounds of the formula (I) according to the invention and/or their salts have excellent herbicidal activity against a broad spectrum of economically important mono- and dicotyledonous annual harmful plants. The compounds to be used according to the invention or the compounds according to the invention also have good control over perennial harmful plants which are difficult to control and produce shoots from rhizomes, root stocks or other perennial organs.

The compounds of the formula (I) to be used according to the invention or the compounds of the formula (I) according to the invention and/or their salts, for example compared to the compounds described in WO 2012/126765 A1, generally have more potent action at the same dosage, for example against weed grasses. Furthermore, the compounds to be used according to the invention or the compounds according to the invention have a broader spectrum of activity against weeds, i.e. the compounds to be used according to the invention or the compounds according to the invention and/or their salts can be used to control effectively a relatively large number of different weeds.

The compounds of the formula (I) to be used according to the invention or the compounds of the formula (I) according to the invention and/or their salts were found to be highly effective in the control of harmful plants such as *Alopecurus myosuroides, Avena fatua, Cyperus esculentus, Echinochloa crus-galli, Lolium multiflorum, Setaria viridis, Abutilon theophrasti, Amaranthus retroflexus, Matricaria inodora* (=*Tripleurospermum maritimum* subsp. *inodorum*), *Polygonum convolvulus* (=*Fallopia convolvulus*), *Stellaria media, Viola tricolor, Veronica persica*, and *Pharbitis purpurea*.

The compounds of the formula (I) to be used according to the invention or the compounds of the formula (I) according to the invention and/or their salts were found to have particularly good herbicidal efficacy against *Alopecurus myosuroides, Echinochloa crus-galli, Lolium multiflorum, Setaria viridis, Stellaria media, Viola tricolor* and *Veronica persica*.

In addition, the compounds of the formula (I) to be used according to the invention or the compounds of the formula (I) according to the invention and/or their salts show particularly good activity in the pre-emergence method, in particular against weed grasses. The pre-emergence activity of the compounds to be used according to the invention or the compounds according to the invention is generally better than the pre-emergence activity of the compounds described in WO 2012/126765 A1.

Furthermore, it has been found that the compounds of the formula (I) to be used according to the invention or the compounds of the formula (I) according to the invention and/or their salts show this better pre-emergence action particularly selectively in certain crops, in particular in oilseed rape, soya beans, cotton and cereals (and here in particular in maize, barley, wheat, rye, oats, triticale, millet varieties, rice).

In general, the compounds of the formula (I) to be used according to the invention or the compounds of the formula (I) according to the invention also have a considerably broader activity spectrum.

In the formula (I), the formula "$(R^2)_n$" means n radicals $R^2$ which are attached as substituents at the phenyl ring in question, where the radicals in the case of n greater than 1 may be identical or different and have the meaning mentioned in each case in more detail. In the case n=0, the phenyl ring in question is not substituted by substituents $R^2$, i.e. all ring carbon atoms of the phenyl ring in positions 2 to 6 are attached to a hydrogen atom. This applies correspondingly to the substitution of the other phenyl ring according to formula $(R^3)_m$.

In the case of $R^1$=H or in the case of suitable acidic substituents, the compounds of the formula (I) are able to form salts by reaction with bases where the acidic hydrogen is replaced by an agriculturally suitable cation.

By addition of a suitable inorganic or organic acid onto a basic group, such as, for example, amino or alkylamino, the compounds of the formula (I) are able to form salts. Suitable acidic groups present, such as, for example, carboxylic acid groups, are able to form inner salts with groups which for their part can be protonated, such as amino groups.

The compounds of the formula (I) may preferably be present in the form of agriculturally usable salts, where the type of salt is otherwise generally immaterial. In general, suitable salts are the salts of those cations or the acid addition salts of those acids whose cations and anions, respectively, have no adverse effect on the herbicidal activity of the compounds of the formula (I).

Suitable cations are in particular ions of the alkali metals, here preferably lithium, sodium or potassium, of the alkaline earth metals, here preferably calcium or magnesium, and of the transition metals, here preferably manganese, copper, zinc or iron. The cation used may also be ammonium ($NH_4^+$) or substituted ammonium, where one to four hydrogen atoms may be replaced here by $(C_1-C_4)$-alkyl, hydroxy-$(C_1-C_4)$-alkyl, $(C_1-C_4)$-alkoxy-$(C_1-C_4)$-alkyl, hydroxy-$(C_1-C_4)$-alkoxy-$(C_1-C_4)$-alkyl, phenyl or benzyl, preferred ammonium ions are ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium. Also suitable are phosphonium ions, sulphonium ions, preferably tri-$(C_1-C_4)$-alkylsulphonium, in particular trimethylsulphonium, or sulphoxonium ions, preferably tri-$(C_1-C_4)$-alkylsulphoxonium, in particular trimethylsulphoxonium.

Anions of suitable acid addition salts are preferably chloride, bromide, fluoride, hydrogensulphate, sulphate, dihydrogenphosphate, hydrogenphosphate, nitrate, bicarbonate, carbonate, hexafluorosilicate, hexafluorophosphate, benzoate and also the anions of $(C_1-C_4)$-alkanoic acids, here in turn preferably formate, acetate, propionate, butyrate or trifluoroacetate.

In formula (I) and in all subsequent formulae, chemical radicals are referred to by names which are collective terms for the enumeration of individual group members or specifically refer to individual chemical radicals. Here, terms are used which are familiar to the person skilled in the art or have the meanings defined below.

A hydrolyzable radical (see definition of R') is a radical which can be hydrolyzed under the application conditions, for example a radical which can be hydrolyzed even in the spray liquor or in particular under the physiological conditions in plants, where a compound of the formula (I) where $R^1$ is not hydrogen is hydrolyzed to the corresponding compound of the formula (I) where $R^1$=H (hydrogen). Expressly, the definition of the hydrolyzable radicals also includes the radicals where $R^1$=hydrocarbon radical or heterocyclyl radical, the two last-mentioned radicals being unsubstituted or substituted, even if some of them are hydrolyzable comparatively slowly.

A hydrocarbon radical is an aliphatic, cycloaliphatic or aromatic monocyclic or, in the case of an optionally substituted hydrocarbon radical, also a bicyclic or polycyclic organic radical based on the elements carbon and hydrogen, including, for example, the radicals alkyl, alkenyl, alkynyl, cycloalkyl, cycloalkenyl, aryl, phenyl, naphthyl, indanyl, indenyl, etc. This applies correspondingly to hydrocarbon radicals in composite meanings, such as hydrocarbonoxy radicals or other hydrocarbon radicals attached via heteroatom groups.

Unless defined in more detail, the hydrocarbon radicals preferably have 1 to 20 carbon atoms, more preferably 1 to 16 carbon atoms, in particular 1 to 12 carbon atoms.

The hydrocarbon radicals, also in the special radicals alkyl, alkoxy, haloalkyl, haloalkoxy, alkylamino and alkylthio, and also the corresponding unsaturated and/or substituted radicals may in each case be straight-chain or branched in the carbon skeleton.

The expression "$(C_1-C_4)$-alkyl" is a brief notation for alkyl having from 1 to 4 carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also encompass straight-chain or branched alkyl radicals with a greater number of carbon atoms, i.e. according to the example also the alkyl radicals having 5 and 6 carbon atoms.

Unless stated specifically or differently, preference is given to the lower carbon skeletons, for example having from 1 to 6 carbon atoms, or having from 2 to 6 carbon atoms in the case of unsaturated groups, in the case of the hydrocarbon radicals such as alkyl, alkenyl and alkynyl radicals, including in composite radicals. Alkyl radicals, including in the combined definitions such as alkoxy, haloalkyl, etc., are, for example, methyl, ethyl, n- or i-propyl, n-, t- or 2-butyl, pentyls, hexyls such as n-hexyl, hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl.

Alkenyl also includes in particular straight-chain or branched hydrocarbon radicals having more than one double bond, such as 1,3-butadienyl and 1,4-pentadienyl, but also allenyl or cumulenyl radicals having one or more cumulated double bonds, for example allenyl(1,2-propadienyl), 1,2-butadienyl and 1,2,3-pentatrienyl.

Alkynyl is, for example, propargyl, but-2-yn-1-yl, but-3-yn-1-yl, 1-methylbut-3-yn-1-yl. Alkynyl also includes, in particular, straight-chain or branched hydrocarbon radicals having more than one triple bond or else having one or more triple bonds and one or more double bonds, for example 1,3-butatrienyl or 3-penten-1-yn-1-yl.

A 3- to 9-membered carbocyclic ring is $(C_3-C_9)$-cycloalkyl or $(C_5-C_9)$-cycloalkenyl.

$(C_3-C_9)$-Cycloalkyl is a carbocyclic saturated ring system having preferably 3-9 carbon atoms, for example cyclopropyl, cyclobutyl, cyclopentyl, cyclohexyl, cycloheptyl, cyclooctyl or cyclononyl. In the case of substituted cycloalkyl, cyclic systems with substituents are included, where the substituents may also be bonded by a double bond on the cycloalkyl radical, for example an alkylidene group such as methylidene.

$(C_5-C_9)$-Cycloalkenyl is a carbocyclic, nonaromatic, partially unsaturated ring system having 5-9 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly.

Alkylidene, for example also in the form of $(C_1-C_{10})$-alkylidene, is the radical of a straight-chain or branched alkane which is bonded via a double bond, the position of the bonding site not being fixed. In the case of a branched alkane, the only positions possible are, of course, those in which two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$.

"Halogen" preferably refers to the group consisting of fluorine, chlorine, bromine and iodine. Haloalkyl, -alkenyl and -alkynyl are alkyl, alkenyl and alkynyl, respectively, which are partially or fully substituted by identical or different halogen atoms, preferably from the group consisting of fluorine, chlorine and bromine, in particular from the group consisting of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

Optionally substituted aryl also includes polycyclic systems, such as tetrahydronaphthyl, indenyl, indanyl, fluorenyl, biphenylyl, where the point of attachment is at the aromatic system.

A heterocyclic radical (heterocyclyl) comprises at least one heterocyclic ring (=carbocyclic ring in which at least one carbon atom is replaced by a heteroatom, preferably by a heteroatom from the group consisting of N, O, S, P, B, Si, Se), which is saturated, unsaturated or heteroaromatic and may be unsubstituted or substituted, where the point of attachment is located at a ring atom. Unless defined otherwise it preferably contains one or more, in particular 1, 2 or 3, heteroatoms in the heterocyclic ring, preferably from the group consisting of N, O, and S; it is preferably an aliphatic heterocyclyl radical having 3 to 7 ring atoms or a heteroaromatic radical having 5 or 6 ring atoms. The heterocyclic radical may, for example, be a heteroaromatic radical or ring (heteroaryl), such as, for example, a monocyclic, bicyclic or polycyclic aromatic system in which at least 1 ring contains one or more heteroatoms.

If the heterocyclyl radical or the heterocyclic ring is optionally substituted, it can be fused to other carbocyclic or heterocyclic rings. Preference is given to benzo-fused heterocyclic or heteroaromatic rings.

Optionally substituted heterocyclyl also includes polycyclic systems, such as, for example, 8-aza-bicyclo[3.2.1]octanyl or 1-aza-bicyclo[2.2.1]heptyl. Optionally substituted heterocyclyl also includes spirocyclic systems, such as, for example, 1-oxa-5-aza-spiro[2.3]hexyl.

Preferably it is a radical of a heteroaromatic ring with a heteroatom from the group consisting of N, O, and S, for example the radical of a five- or six-membered ring such as pyridyl, pyrrolyl, thienyl or furyl; with further preference it is a radical of a corresponding heteroaromatic ring having 2, 3 or 4 heteroatoms, such as pyrimidinyl, pyridazinyl, pyrazinyl, triazinyl, tetrazinyl, thiazolyl, thiadiazolyl, oxazolyl, isoxazolyl, pyrazolyl, imidazolyl or triazolyl or tetrazolyl.

Here, preference is given to a radical of a heteroaromatic five- or six-membered ring having 1 to 4 heteroatoms, such as, for example, 1,2,3-triazolyl, 1,2,4-triazolyl, tetrazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, tetrazolyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, thiazolyl, isothiazolyl, oxazolyl, isoxazolyl, pyrazolyl, imidazolyl.

More preference is given here to heteroaromatic radicals of five-membered heterocycles having 3 nitrogen atoms such as 1,2,3-triazol-1-yl, 1,2,3-triazol-4-yl, 1,2,3-triazol-5-yl, 1,2,5-triazol-1-yl, 1,2,5-triazol-3-yl, 1,3,4-triazol-1-yl, 1,3,4-triazol-2-yl, 1,2,4-triazol-3-yl, 1,2,4-triazol-5-yl; more preference is also given to heteroaromatic radicals of six-membered heterocycles having 3 nitrogen atoms such as 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl; more preference is also given to heteroaromatic radicals of five-membered heterocycles having two nitrogen atoms and one oxygen atom such as 1,2,4-oxadiazol-3-yl; 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl; more preference is also given to heteroaromatic radicals of five-membered heterocycles having two nitrogen atoms and one sulphur atom such as 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl; more preference is also given to heteroaromatic radicals of five-membered heterocycles having four nitrogen atoms such as 1,2,3,4-tetrazol-1-yl, 1,2,3,4-tetrazol-5-yl, 1,2,3,5-tetrazol-1-yl, 1,2,3,5-tetrazol-4-yl, 2H-1,2,3,4-tetrazol-5-yl, 1H-1,2,3,4-tetrazol-5-yl, more preference is also given to heteroaromatic radicals of six-membered heterocycles such as 1,2,4,5-tetrazin-3-yl; more preference is also given to heteroaromatic radicals of five-membered heterocycles having three nitrogen atoms and one oxygen or sulphur atom such as 1,2,3,4-oxatriazol-5-yl; 1,2,3,5-oxatriazol-4-yl; 1,2,3,4-thiatriazol-5-yl; 1,2,3,5-thiatriazol-4-yl; more preference is also given to heteroaromatic radicals of six-membered heterocycles such as, for example, 1,2,4,6-thiatriazin-1-yl; 1,2,4,6-thiatriazin-3-yl; 1,2,4,6-thiatriazin-5-yl.

Furthermore preferably, the heterocyclic radical or ring is a partially or fully hydrogenated heterocyclic radical having one heteroatom from the group of N, O and S, for example oxiranyl, oxetanyl, oxolanyl (=tetrahydrofuryl), oxanyl, pyrrolinyl, pyrrolidyl or piperidyl.

It is also preferably a partially or fully hydrogenated heterocyclic radical having 2 heteroatoms from the group of N, O and S, for example piperazinyl, dioxolanyl, oxazolinyl, isoxazolinyl, oxazolidinyl, isoxazolidinyl and morpholinyl. Suitable substituents for a substituted heterocyclic radical are the substituents specified later on below, and additionally also oxo. The oxo group may also occur on the hetero-ring atoms which are able to exist in different oxidation states, as in the case of N and S, for example.

Preferred examples of heterocyclyl are a heterocyclic radical having from 3 to 6 ring atoms from the group of pyridyl, thienyl, furyl, pyrrolyl, oxiranyl, 2-oxetanyl, 3-oxetanyl, oxolanyl (=tetrahydrofuryl), pyrrolidyl, piperidyl, especially oxiranyl, 2-oxetanyl, 3-oxetanyl or oxolanyl, or is a heterocyclic radical having two or three heteroatoms, for example pyrimidinyl, pyridazinyl, pyrazinyl, triazinyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

Preferred heterocyclic radicals are also benzo-fused heteroaromatic rings, for example benzofuryl, benzisofuryl, benzothiophenyl, benzisothiophenyl, isobenzothiophenyl, indolyl, isoindolyl, indazolyl, benzimidazolyl, benzotriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,1,3-benzoxadiazolyl, 1,2,3-benzothiadiazolyl, 2,1,3-benzothiadiazolyl, quinolyl (quinolinyl), isoquinolyl (isoquinolinyl), quinnolinyl, phtalazinyl, quinazolinyl, quinoxalinyl, naphthyridinyl, benzotriazinyl, purinyl, pteridinyl, indolizinyl, benzo-1,3-dioxylyl, 4H-benzo-1,3-dioxinyl and 4H-benzo-1,4-dioxinyl, and, where possible, N-oxides and salts thereof.

When a base structure is substituted "by one or more radicals" from a list of radicals (=group) or a generically defined group of radicals, this in each case includes simultaneous substitution by a plurality of identical and/or structurally different radicals.

Substituted radicals, such as a substituted alkyl, alkenyl, alkynyl, cycloalkyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulphinyl, alkylsulphonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as substituted alkyl, etc., substituents include, in addition to the saturated hydrocarbon containing radicals mentioned, corresponding unsaturated aliphatic and aromatic radicals, such as optionally substituted alkenyl, alkynyl, alkenyloxy, alkynyloxy, phenyl and phenoxy. In the case of substituted cyclic radicals having aliphatic moieties in the ring, cyclic systems with those substituents which are bonded on the ring by a double bond are also included, for example substituted by an alkylidene group such as methylidene or ethylidene.

The term "radicals from the group consisting of" followed by a group (list of the substituents) is, wherever used, synonymous with "radicals selected from the group consisting of" (list of the substituents).

The substituents given by way of example ("first substituent level") can, if they include hydrocarbon-containing fractions, be further substituted therein if desired ("second substituent level"), by for example one of the substituents as defined for the first substituent level. Corresponding further substituent levels are possible. The term "substituted radical" preferably embraces just one or two substituent levels.

Here, preferred substituents for the substituent levels are amino, hydroxyl, halogen, nitro, cyano, mercapto, carboxyl, carbonamide, $SF_5$, aminosulphonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulphinyl, alkylsulphonyl, monoalkylaminosulphonyl, dialkylaminosulphonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino.

Two substituents together may also form a saturated or unsaturated hydrocarbon bridge or a corresponding bridge in which carbon atoms, CH groups or $CH_2$ groups are replaced by heteroatoms, thus forming a fused-on or fused cycle. Here, with preference benzo-fused systems based on the base structure are formed.

Optionally substituted phenyl is preferably unsubstituted phenyl or phenyl which is substituted by one or more radicals from the group consisting of halogen, cyano, $(C_1-C_4)$-alkyl, $(C_1-C_4)$-haloalkyl, $(C_1-C_4)$-alkoxy-$(C_1-C_4)$alkyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and nitro, in particular phenyl which is optionally substituted by one or more radicals from the group consisting of halogen, $(C_1-C_4)$-alkyl, $(C_1-C_4)$-haloalkyl and $(C_1-C_4)$-alkoxy.

In the case of substituents having carbon atoms, preference is given to those having 1 to 6 carbon atoms, preferably to those having 1 to 4 carbon atoms, especially to those having 1 or 2 carbon atoms. Preference is generally given to substituents from the group of halogen, e.g. fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy, fluorine and chlorine.

Substituted amino, such as mono- or disubstituted amino, is a radical from the group of the substituted amino radicals which are N-substituted, for example, by one or two identical or different radicals from the group of alkyl, alkoxy, acyl and aryl; preferably mono- and dialkylamino, mono- and diarylamino, acylamino, N-alkyl-N-arylamino, N-alkyl-N-acylamino and N-heterocycles; preference is given to alkyl radicals having from 1 to 4 carbon atoms; aryl is preferably phenyl or substituted phenyl; acyl is as defined below, preferably $(C_1-C_4)$-alkanoyl. The same applies to substituted hydroxylamino or hydrazino.

Acyl is a radical of an organic acid which arises in a formal sense by removal of a hydroxyl group on the acid function, and the organic radical in the acid may also be bonded to the acid function via a heteroatom. Examples of acyl are the radicals of a carboxylic acid and radicals of acids derived therefrom, such as those of thiocarboxylic acid, optionally N-substituted iminocarboxylic acids or the radical of carbonic monoesters, N-substituted carbamic acid, sulphonic acids, sulphinic acids, N-substituted sulphonamide acids, phosphonic acids or phosphinic acids.

Acyl is, for example, formyl, alkylcarbonyl, here preferably [($C_1$-$C_4$)-alkyl]carbonyl, phenylcarbonyl, alkyloxycarbonyl, phenyloxycarbonyl, benzyloxycarbonyl, alkylsulphonyl, alkylsulphinyl, N-alkyl-1-iminoalkyl and other radicals of organic acids. The radicals may each for their part be substituted in the alkyl or phenyl moiety, for example in the alkyl moiety by one or more radicals from the group of halogen, alkoxy, phenyl and phenoxy; examples of substituents in the phenyl moiety are the substituents already mentioned above in general for substituted phenyl.

Acyl is preferably an acyl radical in the narrower sense, i.e. a radical of an organic acid in which the acid group is bonded directly to the carbon atom of an organic radical, for example formyl, alkylcarbonyl such as acetyl or [($C_1$-$C_4$)-alkyl]carbonyl, phenylcarbonyl, alkylsulphonyl, alkylsulphinyl and other radicals of organic acids.

In a preferred embodiment, acyl is an alkanoyl radical having 1 to 8 carbon atoms, preferably 1 to 6 carbon atoms, particularly preferably 1 to 4 carbon atoms. Here, ($C_1$-$C_4$)-alkanoyl is the radical of an alkanoic acid having 1 to 6 carbon atoms formed after removal of the OH group of the acid group, i.e. formyl, acetyl, n-propionyl, isopropionyl, n-, iso-, sec- or tert-butanoyl, n-, iso-, sec- or tert-pentanoyl, n-, iso- or sec-hexanoyl.

The "yl position" of a radical denotes the carbon atom having the free bond.

In the context of the present text, compounds of the formula (I) according to the invention and compounds of the formula (I) to be used according to the invention and/or salts thereof are in short also referred to as "compounds (I)".

The invention also provides all stereoisomers which are encompassed by formula (I) and mixtures thereof. Compounds of the formula (I) contain two or more asymmetric carbon atoms, and may also contain double bonds, the stereochemistry of which is not stated separately in the general formula (I). The possible stereoisomers defined by their specific three-dimensional shape, such as enantiomers, diastereomers, Z- and E-isomers, are all encompassed by the formula (I) and can be obtained from mixtures of the stereoisomers by customary methods or else prepared by stereoselective reactions in combination with the use of stereochemically pure starting materials.

The compounds of the formula (I) to be used according to the invention and the compounds of the formulae (Ia) and (Ib) defined below include all stereoisomers which can occur on the basis of the centres of asymmetry and/or double bonds in the molecule whose configuration is not designated specifically or not stated specifically in the respective structural formulae, and mixtures thereof, including the racemic mixtures and the mixtures enriched partly with particular stereoisomers.

The invention also provides all tautomers of the compounds of the formula (I) which may result from a hydrogen atom shift (for example keto-enol tautomers). The compound of the formula (I) also includes the tautomers, even if formally the formula (I) correctly describes only one of the respective tautomers which are in equilibrium with one another or which can be converted into one another.

The compounds of the formula (I) also include all physical forms in which they may be present as a pure substance or, if appropriate, as a mixture with other compounds, in particular also polymorphic crystal forms of the compounds of the formula (I) and salts thereof and solvent adducts (for example hydrates).

Primarily for reasons of higher herbicidal activity, better selectivity and/or better producibility, compounds of the abovementioned formula (I) according to the invention or their salts or their use according to the invention are of particular interest in which individual radicals have one of the preferred meanings already specified or specified below, or in particular those in which one or more of the preferred meanings already specified or specified below occur in combination.

Irrespective of the respective other radicals from the group consisting of $R^1$, $(R^2)_n$ and $(R^3)_m$ and the subdefinitions corresponding to the general radicals, and preferably in combination with preferred definitions of one or more of these radicals, compounds according to the invention or uses according to the invention of compounds of particular interest are those with the preferred meanings listed below of the radicals in question.

Preference is given to compounds of the formula (I) according to the invention and compounds of the formula (I) to be used according to the invention or salts thereof in which $R^1$ represents hydrogen or a hydrolyzable radical having a total of up to 30 carbon atoms, with preference a hydrolyzable radical having a total of 1 to 24 carbon atoms, preferably having a total of 1 to 20 carbon atoms, more preferably having a total of 1 to 16 carbon atoms, particularly preferably having a total of 1 to 12 carbon atoms.

More preference is given to compounds of the formula (I) according to the invention and compounds of the formula (I) to be used according to the invention or salts thereof in which $R^1$ represents hydrogen or a hydrolyzable radical having a total of 1 to 24 carbon atoms, where $R^1$
represents an optionally substituted hydrocarbon radical or an optionally substituted heterocyclyl radical, or
represents a radical of the formula $SiR^aR^bR^c$, or —$NR^aR^b$,
where each of the radicals $R^a$ and $R^b$ independently of the other represents hydrogen or an optionally substituted hydrocarbon radical and W independently represents an optionally substituted hydrocarbon radical, or —$NR^aR^b$ represents a 3- to 9-membered heterocycle which, in addition to this nitrogen atom, may contain one or two further ring heteroatoms from the group consisting of N, O and S and which is substituted or unsubstituted, or
represents a radical of the formula —C(=O)—$R^e$ or —P(=O)($R^f$)$_2$ where $R^e$ and the two radicals $R^f$ each independently of one another are selected from the group consisting of hydrogen, OH, unsubstituted or substituted ($C_1$-$C_8$)-alkyl, unsubstituted or substituted ($C_1$-$C_4$)-haloalkyl, unsubstituted or substituted ($C_2$-$C_8$)-alkenyl, unsubstituted or substituted ($C_2$-$C_8$)-alkynyl, unsubstituted or substituted ($C_1$-$C_6$)-alkoxy, unsubstituted or substituted ($C_1$-$C_6$)-alkoxy-($C_1$-$C_8$)-alkyl, unsubstituted or substituted ($C_1$-$C_4$)-haloalkoxy, unsubstituted or substituted ($C_1$-$C_4$)-haloalkoxy-($C_1$-$C_8$)-alkyl, unsubstituted or substituted ($C_3$-$C_8$)-alkenyloxy, unsubstituted or substituted ($C_3$-$C_8$)-alkenyloxy-($C_1$-$C_8$)-alkyl, unsubstituted or substituted ($C_3$-$C_8$)-alkynyloxy, unsubstituted or substituted ($C_3$-$C_8$)-alkynyloxy-($C_1$-$C_8$)-alkyl, unsubstituted or substituted —NR*R**, where R* and R** are as defined above, unsubstituted or substituted tri-[($C_1$-$C_4$)-alkyl]silyl, unsubstituted or substituted tri-[($C_1$-$C_4$)-alkyl]silyl-($C_1$-$C_8$)alkyl, unsubstituted or substituted ($C_3$-$C_6$)-cycloalkyl, unsubstituted or substituted ($C_3$-$C_6$)-cycloalkyl-($C_1$-$C_8$)-alkyl, unsubstituted or substituted ($C_5$-$C_6$)-cycloalkenyl, unsubstituted or substituted ($C_5$-$C_6$)-cycloalkenyl-($C_1$-$C_8$)-alkyl, unsubstituted or substituted ($C_5$-$C_6$)-cycloalkynyl, unsubstituted or substituted ($C_5$-$C_6$)-cycloalkynyl-($C_1$-$C_8$)-alkyl, unsubstituted or substituted phenyl, unsubstituted or substituted phenyl-($C_1$-$C_8$)-alkyl, unsubstituted or substituted phenoxy, unsubstituted or substituted phenoxy-($C_1$-$C_8$)-alkyl, unsubstituted or substituted phenylamino, unsubstituted or substituted phenylamino-($C_1$-$C_8$)-alkyl, unsubstituted or substituted Het, unsubstituted or substituted Het-($C_1$-$C_6$)-alkyl and unsubstituted or substituted Het-O—($C_1$-$C_6$)-alkyl, where Het in each case represents a saturated, partially unsaturated or heteroaromatic monocyclic heterocyclyl radical having 3 to 9 ring atoms or a 9- or 10-membered bicyclic heterocycle in each case containing 1, 2, 3 or 4 heteroatoms selected from the group consisting of O, N and S, where each of the substituted radicals mentioned is substituted in the acyclic moiety by one or more identical or different radicals $R^A$ and/or where each of the substituted radicals mentioned is substituted in the cyclic moiety by one or more identical or different radicals $R^B$, where $R^A$ represents halogen, cyano, hydroxy or ($C_1$-$C_6$)-alkoxy, and $R^B$ independently of any other radicals $R^B$ present is selected from the group consisting of halogen, cyano, hydroxyl, oxo, nitro, ($C_1$-$C_8$)-alkyl, ($C_1$-$C_6$)-haloalkyl, cyano-($C_1$-$C_6$)-alkyl, hydroxy-($C_1$-$C_6$)-alkyl, nitro-($C_1$-$C_6$)-alkyl, ($C_2$-$C_8$)-alkenyl, ($C_2$-$C_8$)-haloalkenyl, ($C_2$-$C_8$)-alkynyl, ($C_2$-$C_8$)-haloalkynyl, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_6$)-alkoxy-($C_1$-$C_6$)-alkyl, ($C_1$-$C_6$)-alkoxy-($C_1$-$C_4$)-alkoxy, ($C_1$-$C_6$)-haloalkoxy-($C_1$-$C_4$)-alkyl, ($C_1$-$C_6$)-haloalkoxy-($C_1$-$C_4$)-alkoxy, ($C_1$-$C_8$)-alkylthio, ($C_2$-$C_6$)-alkenylthio, ($C_2$-$C_6$)-alkynylthio, ($C_1$-$C_8$)-alkylsulphinyl, ($C_1$-$C_6$)-haloalkylsulphinyl, ($C_1$-$C_8$)-alkylsulphonyl, ($C_1$-$C_6$)-haloalkylsulphonyl, $R^{aa}$—C(=O)—, $R^{aa}$—C(=O)—($C_1$-$C_6$)-alkyl, —NR*R**, tri-[($C_1$-$C_4$)-alkyl]silyl, tri-[($C_1$-$C_4$)-alkyl]silyl-($C_1$-$C_6$)-alkyl, ($C_3$-$C_8$)-cycloalkyl, ($C_3$-$C_8$)-cycloalkoxy, ($C_3$-$C_8$)-cycloalkyl-($C_1$-$C_8$)-alkyl, ($C_3$-$C_8$)-cycloalkyl-($C_1$-$C_8$)-alkoxy, phenyl, phenyl-($C_1$-$C_8$)-alkyl, phenoxy, phenoxy-($C_1$-$C_8$)-alkyl, phenylamino, phenylamino-($C_1$-$C_8$)-alkyl or a 5- or 6-membered monocyclic or 9- or 10-membered bicyclic heterocycle which contains 1, 2, 3 or 4 heteroatoms selected from the group consisting of O, N and S, where each of these radicals mentioned may be substituted in the cyclic moiety by one or more identical or different radicals $R^{bb}$, where $R^{aa}$ independently of one another each represent hydrogen, OH, ($C_1$-$C_8$)-alkyl, ($C_1$-$C_6$)-haloalkyl, ($C_2$-$C_8$)-alkenyl, ($C_2$-$C_8$)-alkynyl, ($C_1$-$C_8$)-alkoxy, ($C_1$-$C_6$)-alkoxy-($C_1$-$C_6$)-alkyl, ($C_1$-$C_6$)-alkoxy-($C_1$-$C_6$)-alkyloxy, ($C_1$-$C_6$)-haloalkoxy, ($C_1$-$C_6$)-haloalkoxy-($C_1$-$C_6$)-alkyl, ($C_1$-$C_6$)-haloalkoxy-($C_1$-$C_6$)-alkoxy, ($C_3$-$C_8$)-alkenyloxy, ($C_3$-$C_8$)-alkenyloxy-($C_1$-$C_6$)-alkyl, ($C_3$-$C_8$)-alkenyloxy-($C_1$-$C_6$)-alkoxy, ($C_3$-$C_8$)-alkynyloxy, ($C_3$-$C_8$)-alkynyloxy-($C_1$-$C_6$)-alkyl, ($C_3$-$C_8$)-alkynyloxy-($C_1$-$C_6$)-alkoxy, —NR*R**, tri-[($C_1$-$C_4$)-alkyl]silyl, tri-[($C_1$-$C_4$)-alkyl]silyl-($C_1$-$C_6$)-alkyl, tri-[($C_1$-$C_4$)-alkyl]silyl-($C_1$-$C_6$)-alkoxy, ($C_3$-$C_8$)-cycloalkyl, ($C_3$-$C_8$)-cycloalkyl, ($C_3$-$C_8$)-cycloalkyl-($C_1$-$C_8$)-alkyl, ($C_3$-$C_8$)-cycloalkyl-($C_1$-$C_8$)-alkoxy, ($C_5$-$C_8$)-cycloalkenyl, ($C_5$-$C_8$)-cycloalkenyl-($C_1$-$C_6$)-alkyl, ($C_5$-$C_8$)-cycloalkenyloxy, ($C_5$-$C_8$)-cycloalkynyl, ($C_5$-$C_8$)-cycloalkynyl-($C_1$-$C_6$)-alkyl, ($C_5$-$C_8$)-cycloalkynyl-($C_1$-$C_6$)-alkoxy, phenyl, phenyl-($C_1$-$C_8$)-alkyl, phenyl-($C_1$-$C_8$)-alkoxy, phenoxy, phenoxy-($C_1$-$C_8$)-alkyl, phenoxy-($C_1$-$C_8$)-alkoxy, phenylamino, phenylamino-($C_1$-$C_8$)-alkyl, phenylamino-($C_1$-$C_8$)-alkoxy or a 5- or 6-membered monocyclic or 9- or 10-membered bicyclic heterocycle which is optionally attached via an alkylene group or an alkoxy group and contains 1, 2, 3 or 4 heteroatoms selected from the group consisting of O, N and S, where each of the radicals $R^{aa}$ comprising a cycle is optionally substituted in the cyclic moiety by one or more identical or different radicals $R^{bb}$, and where R*, R**, —NR*R** and $R^{bb}$ have the meaning given above.

More preference is given to compounds of the formula (I) according to the invention and compounds of the formula (I) to be used according to the invention or salts thereof in which $R^1$ represents hydrogen, unsubstituted ($C_1$-$C_{18}$)-alkyl, unsubstituted ($C_2$-$C_{18}$)-alkenyl, unsubstituted ($C_2$-$C_{18}$)-alkynyl, substituted ($C_1$-$C_{18}$)-alkyl, substituted ($C_2$-$C_{18}$)-alkenyl or substituted ($C_2$-$C_{18}$)-alkynyl, where in the case of substituted ($C_1$-$C_{18}$)-alkyl, substituted ($C_2$-$C_{18}$)-alkenyl and substituted ($C_2$-$C_{18}$)-alkynyl the substituent(s) is/are in each case independently of one another selected from groups (a)-(e) below:

(a) halogen, cyano, thio, nitro, hydroxyl, carboxyl, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_4$)-alkoxy-($C_1$-$C_4$)-alkoxy, ($C_1$-$C_8$)-alkylthio, ($C_2$-$C_8$)-alkenylthio, ($C_2$-$C_8$)-alkynylthio, ($C_1$-$C_8$)-haloalkylthio, ($C_2$-$C_8$)-haloalkenylthio, ($C_2$-$C_8$)-haloalkynylthio, ($C_1$-$C_8$)-alkylsulphinyl, ($C_2$-$C_8$)-alkenylsulphinyl, ($C_2$-$C_8$)-alkynylsulphinyl, ($C_1$-$C_8$)-haloalkylsulphinyl, ($C_2$-$C_8$)-haloalkenylsulphinyl, ($C_2$-$C_8$)-haloalkynylsulphinyl, ($C_1$-$C_8$)-alkylsulphonyl, ($C_2$-$C_8$)-alkenylsulphonyl, ($C_2$-$C_8$)-alkynylsulphonyl, ($C_1$-$C_8$)-haloalkylsulphonyl, ($C_2$-$C_8$)-haloalkenylsulphonyl, ($C_2$-$C_8$)-haloalkynylsulphonyl, —NR*R**, where R*, R** and —NR*R** each have the meaning given above, (b) ($C_3$-$C_8$)-cycloalkyl, ($C_5$-$C_8$)-cycloalkenyl, ($C_5$-$C_8$)-cycloalkynyl, ($C_3$-$C_8$)-cycloalkyl-($C_1$-$C_6$)-alkoxy, ($C_3$-$C_8$)-cycloalkyl, ($C_1$-$C_6$)-alkyl-S(O)$_p$—, ($C_5$-$C_8$)-cycloalkenyl-($C_1$-$C_6$)-alkoxy, ($C_5$-$C_8$)-cycloalkenyl-($C_1$-$C_6$)-alkyl-S(O)$_p$—, ($C_5$-$C_8$)-cycloalkynyl-($C_1$-$C_6$)-alkoxy, ($C_5$-$C_8$)-cycloalkynyl-($C_1$-$C_6$)-alkyl-S(O)$_p$—, ($C_3$-$C_8$)-cycloalkoxy, ($C_3$-$C_8$)-cycloalkyl-S(O)$_p$—, ($C_5$-$C_8$)-cycloalkenyloxy, ($C_5$-$C_8$)-cycloalkenyl-S(O)$_p$—, ($C_5$-$C_8$)-cycloalkynyloxy, ($C_5$-$C_8$)-cycloalkynyl-S(O)$_p$—, ($C_3$-$C_8$)-cycloalkoxy-($C_1$-$C_6$)-alkoxy, ($C_3$-$C_8$)-cycloalkoxy-($C_1$-$C_6$)-alkyl-S(O)$_p$—, phenyl, phenyl-($C_1$-$C_6$)-alkoxy, phenoxy, phenyl-S(O)$_p$—, phenyl-($C_1$-$C_6$)-alkyl-S(O)$_p$—, phenoxy-($C_1$-$C_6$)-alkoxy, phenoxy-($C_1$-$C_6$)-alkyl-S(O)$_p$—, a radical Het$^1$, Het$^1$-S(O)$_p$—, Het$^1$-($C_1$-$C_6$)-alkoxy, Het$^1$-O—, Het$^1$-O—($C_1$-$C_6$)-alkoxy, where the radical Het$^1$ has the meaning given above and where each of the last-mentioned radicals of group (b) is unsubstituted in the acyclic moiety or substituted by one or more identical or different radicals selected from the group consisting of halogen, cyano, hydroxyl and ($C_1$-$C_6$)-alkoxy, and/or unsubstituted in the cyclic moiety or substituted by one or more identical or different radicals $R^B$, where $R^B$ has the meaning given above, and the index p in each case represents 0, 1 or 2,
- (c) —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), —P(=O)(O$R^C$)(O$R^D$) or —O—P(=O)(O$R^C$)(O$R^D$),
  where R*, R** and —NR*R** each have the meaning given above and $R^C$ and $R^D$ are as defined below,
- (d) —SiR'$_3$, —O—SiR'$_3$, (R')$_3$Si—(C$_1$-C$_6$)alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$, in which each of the radicals R' is independently selected from the group consisting of H, (C$_1$-C$_4$)-alkyl or phenyl which is unsubstituted or substituted by one or more radicals from the group consisting of halogen, (C$_1$-C$_4$)-alkyl, (C$_1$-C$_4$)-alkoxy, (C$_1$-C$_4$)-haloalkyl, (C$_1$-C$_4$)-haloalkoxy and nitro or substituted at two adjacent positions by a (C$_2$-C$_6$)-alkylene bridge, and the index q represents an integer from 0 to 6, and
- (e) R"O—CHR'''CH(OR")—(C$_1$-C$_6$)-alkoxy,
  in which each of the radicals R" independently of the others represents H or (C$_1$-C$_4$)-alkyl or together the radicals represent a (C$_1$-C$_6$)-alkylene group and R''' represents H or (C$_1$-C$_4$)-alkyl, or $R^1$ represents (C$_3$-C$_9$)-cycloalkyl, (C$_5$-C$_9$)-cycloalkenyl, (C$_5$-C$_9$)-cycloalkynyl or phenyl,
  where each of these radicals is unsubstituted or substituted by one or more radicals from the group consisting of the radicals of subgroups (a')-(e') below:
- (a') halogen, cyano, thio, nitro, hydroxyl, carboxyl, (C$_1$-C$_8$)-alkyl, (C$_1$-C$_8$)-haloalkyl, (C$_1$-C$_4$)-alkoxy-(C$_1$-C$_4$)-alkyl, (C$_2$-C$_8$)-alkenyl, (C$_2$-C$_8$)-haloalkenyl, (C$_2$-C$_8$)-alkynyl, (C$_2$-C$_8$)-haloalkynyl, (C$_1$-C$_8$)-alkoxy, (C$_2$-C$_8$)-alkenyloxy, (C$_2$-C$_8$)-alkynyloxy, (C$_1$-C$_8$)-haloalkoxy, (C$_1$-C$_4$)-alkoxy-(C$_1$-C$_4$)-alkoxy, (C$_1$-C$_8$)-alkylthio, (C$_2$-C$_8$)-alkenylthio, (C$_2$-C$_8$)-alkynylthio and —NR*R**, where R*, R**, —NR*R** and $R^{bb}$ each have the meaning given above,
- (b') radicals of the formulae —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), —P(=O)(O$R^C$)(O$R^D$) or —O—P(=O)(O$R^C$)(O$R^D$),
  where R*, R**, —NR*R** and $R^{bb}$ have the meaning given above and $R^C$ and $R^D$ have the meaning defined below,
- (c') radicals of the formulae —SiR'$_3$, —O—SiR'$_3$, (R')$_3$Si—(C$_1$-C$_6$)-alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$,
  in which each of the radicals R' independently of the others represents H, (C$_1$-C$_4$)-alkyl or phenyl which is unsubstituted or substituted by one or more radicals from the group consisting of halogen, (C$_1$-C$_4$)-alkyl, (C$_1$-C$_4$)-alkoxy, (C$_1$-C$_4$)-haloalkyl, (C$_1$-C$_4$)-haloalkoxy and nitro or is substituted at two adjacent positions by a (C$_2$-C$_6$)-alkylene bridge, and q represents an integer from 0 to 6, and
- (d') radicals of the formula R"O—CHR'''CH(OR")—(C$_1$-C$_6$)-alkoxy,
  in which each of the radicals R" independently of the others represents H or (C$_1$-C$_4$)-alkyl or together the radicals represent a (C$_1$-C$_6$)-alkylene group and R''' represents H or (C$_1$-C$_4$)-alkyl, and
- (e') a radical of the formula Het$^1$ which is unsubstituted or substituted by one or more identical or different radicals $R^B$, where $R^B$ has the meaning given above, or $R^1$ represents a polycyclic radical based on (C$_3$-C$_9$)-cycloalkyl, (C$_5$-C$_9$)-cycloalkenyl, (C$_5$-C$_9$)-cycloalkynyl or phenyl, where the base ring is fused with a carbocyclic or heterocyclic ring, preferably a 5- or 6-membered ring having 0, 1, 2 or 3 ring heteroatoms from the group consisting of N, O and S, preferably benzo-fused, and where the base ring or the polycyclic system is unsubstituted or substituted by one or more identical or different radicals $R^B$, where $R^B$ has the meaning given above,
  preferably unsubstituted or substituted by one or more radicals selected from the group consisting of halogen, cyano, nitro, hydroxyl, carboxyl, (C$_1$-C$_6$)-alkyl, (C$_1$-C$_6$)-haloalkyl, (C$_1$-C$_4$)-alkoxy-(C$_1$-C$_4$)-alkyl, (C$_2$-C$_6$)-alkenyl, (C$_2$-C$_6$)-haloalkenyl, (C$_2$-C$_6$)-alkynyl, (C$_2$-C$_6$)-haloalkynyl, (C$_1$-C$_6$)-alkoxy, (C$_2$-C$_6$)-alkenyloxy, (C$_2$-C$_6$)-alkynyloxy, (C$_1$-C$_6$)-haloalkoxy, C$_4$-alkoxy-(C$_1$-C$_4$)-alkoxy, (C$_1$-C$_6$)-alkylthio, (C$_2$-C$_6$)-alkenylthio, (C$_2$-C$_6$)-alkynylthio, (C$_3$-C$_6$)-cycloalkyl, (C$_3$-C$_6$)-cycloalkoxy, [(C$_1$-C$_8$)-alkoxy]carbonyl, [(C$_1$-C$_6$)-haloalkoxy]carbonyl and oxo, or $R^1$ represents a heterocyclic radical Het$^1$ which is unsubstituted in the ring or in the polycyclic system or substituted by one or more identical or different radicals $R^B$, where $R^B$ has the meaning given above, preferably unsubstituted or substituted by one or more radicals from the group consisting of halogen, cyano, thio, nitro, hydroxyl, carboxyl, (C$_1$-C$_6$)-alkyl, (C$_1$-C$_6$)-haloalkyl, (C$_1$-C$_4$)-alkoxy-(C$_1$-C$_4$)-alkyl, (C$_2$-C$_6$)-alkenyl, (C$_2$-C$_6$)-haloalkenyl, (C$_2$-C$_6$)-alkynyl, (C$_2$-C$_6$)-haloalkynyl, (C$_1$-C$_6$)-alkoxy, (C$_2$-C$_6$)-alkenyloxy, (C$_2$-C$_6$)-alkynyloxy, (C$_1$-C$_6$)-haloalkoxy, (C$_1$-C$_4$)-alkoxy-(C$_1$-C$_4$)-alkoxy, (C$_1$-C$_6$)-alkylthio, (C$_2$-C$_6$)-alkenylthio, (C$_2$-C$_6$)-alkynylthio, (C$_3$-C$_6$)-cycloalkyl, (C$_3$-C$_6$)-cycloalkoxy, [(C$_1$-C$_8$)-alkoxy]carbonyl, [(C$_1$-C$_6$)-haloalkoxy]carbonyl and oxo, where Het$^1$ in each case independently of the others is a saturated, partially unsaturated or heteroaromatic monocyclic heterocyclyl radical having 3 to 9 ring atoms, preferably having 5 or 6 ring atoms, or a 9- or 10-membered bicyclic heterocycle which contains 1, 2, 3 or 4 heteroatoms selected from the group consisting of O, N and S, preferably a 5- or 6-membered heterocycle having 1 to 3 ring heteroatoms from the group consisting of N, O and S which is optionally also fused to a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably optionally benzo-fused, $R^A$ has the meaning given above, $R^B$ has the meaning given above, and where $R^B$ preferably represents a radical selected from the group consisting of halogen, cyano, hydroxyl, oxo, nitro, (C$_1$-C$_6$)-alkyl, (C$_1$-C$_4$)-haloalkyl, cyano-(C$_1$-C$_4$)-alkyl, hydroxy-(C$_1$-C$_4$)-alkyl, nitro-(C$_1$-C$_4$)-alkyl, (C$_2$-C$_6$)-alkenyl, (C$_2$-C$_6$)-haloalkenyl, ($C_2$-$C_6$)-alkynyl, ($C_2$-$C_6$)-haloalkynyl, ($C_1$-$C_6$)-alkoxy, ($C_2$-$C_6$)-alkenyloxy, ($C_2$-$C_6$)-alkynyloxy, ($C_1$-$C_6$)-haloalkoxy, ($C_1$-$C_4$)-alkoxy-($C_1$-$C_4$)-alkyl, ($C_1$-$C_4$)-alkoxy-($C_1$-$C_4$)-alkoxy-($C_1$-$C_4$)-haloalkoxy-($C_1$-$C_4$)-alkyl, ($C_1$-$C_4$)-haloalkoxy-($C_1$-$C_4$)-alkoxy, ($C_1$-$C_6$)-alkylthio, ($C_2$-$C_6$)-alkenylthio, ($C_2$-$C_6$)-alkynylthio, ($C_1$-$C_6$)-alkylsulphinyl, ($C_1$-$C_6$)-haloalkylsulphinyl, ($C_1$-$C_6$)-alkylsulphonyl, ($C_1$-$C_6$)-haloalkylsulphonyl, a radical of the formula $R^{aa}$—C(=O)— or $R^{aa}$—C(=O)—($C_1$-$C_6$)-alkyl where $R^{aa}$ has the meaning given above, —NR*R**, where R*, R**, —NR*R** and $R^{bb}$ each have the meaning given above, tri-[($C_1$-$C_4$)-alkyl]silyl, tri-[($C_1$-$C_4$)-alkyl]silyl-($C_1$-$C_6$)-alkyl, ($C_3$-$C_6$)-cycloalkyl, ($C_3$-$C_6$)-cycloalkoxy, ($C_3$-$C_6$)-cycloalkyl-($C_1$-$C_4$)-alkyl, ($C_3$-$C_6$)-cycloalkyl-($C_1$-$C_8$)-alkoxy, phenyl, phenyl-($C_1$-$C_6$)-alkyl, phenoxy, phenoxy-($C_1$-$C_6$)-alkyl, phenylamino, phenylamino-($C_1$-$C_6$)-alkyl or a 5- or 6-membered monocyclic or 9- or 10-membered bicyclic heterocycle which contains 1, 2, 3 or 4 heteroatomes selected from the group consisting of O, N and S, where each of the radicals $R^B$ is optionally substituted in the cyclic moiety by one or more identical or different radicals $R^{bb}$, where $R^B$ and $R^{bb}$ each have the meaning given above, $R^C$ and $R^D$ each independently of one another (and also independently of radicals $R^C$, $R^D$ in other groups) represents a radical selected from the group consisting of:
(i) hydrogen, unsubstituted ($C_1$-$C_8$)-alkyl, unsubstituted ($C_2$-$C_8$)-alkenyl, unsubstituted ($C_2$-$C_8$)-alkynyl, substituted ($C_1$-$C_8$)-alkyl, substituted ($C_2$-$C_8$)-alkenyl and substituted ($C_2$-$C_8$)-alkynyl, where each of these substituted radicals is substituted by one or more radicals from the group consisting of halogen, cyano, nitro, hydroxyl, ($C_1$-$C_6$)-alkoxy, ($C_2$-$C_6$)-alkenyloxy, ($C_2$-$C_6$)-alkinyloxy, ($C_1$-$C_8$)-haloalkoxy, ($C_1$-$C_4$)-alkoxy-($C_1$-$C_4$)-alkoxy, ($C_1$-$C_8$)-alkylthio, ($C_1$-$C_8$)-haloalkylthio, ($C_1$-$C_8$)-alkylsulphinyl, ($C_1$-$C_8$)-haloalkylsulphinyl, ($C_1$-$C_8$)-alkylsulphonyl, ($C_1$-$C_8$)-haloalkylsulphonyl and tri-[($C_1$-$C_4$)alkyl]silyl, and
(ii) ($C_3$-$C_8$)-cycloalkyl, ($C_5$-$C_8$)-cycloalkenyl, ($C_5$-$C_8$)-cycloalkynyl, phenyl, ($C_3$-$C_8$)-cycloalkyl-($C_1$-$C_6$)-alkyl, ($C_5$-$C_8$)-cycloalkenyl-($C_1$-$C_6$)-alkyl, ($C_5$-$C_8$)-cycloalkynyl-($C_1$-$C_6$)-alkyl, phenyl-($C_1$-$C_6$)-alkyl, ($C_3$-$C_8$)-cycloalkyloxy-($C_1$-$C_6$)-alkyl, ($C_3$-$C_8$)-cycloalkyl-S(O)$_p$—($C_1$-$C_6$)-alkyl, ($C_5$-$C_8$)-cycloalkenyloxy-($C_1$-$C_6$)-alkyl, ($C_5$-$C_8$)-cycloalkynyloxy-($C_1$-$C_6$)-alkyl, phenoxy-($C_1$-$C_6$)-alkyl, phenyl-S(O)$_p$—($C_1$-$C_6$)-alkyl, ($C_3$-$C_8$)-cycloalkylamino-($C_1$-$C_6$)-alkyl, ($C_5$-$C_8$)-cycloalkenylamino-($C_1$-$C_6$)-alkyl, ($C_5$-$C_8$)-cycloalkynylamino-($C_1$-$C_6$)-alkyl, phenylamino-($C_1$-$C_6$)-alkyl, $Het^1$, $Het^1$-($C_1$-$C_6$)-alkyl, $Het^1$-O—($C_1$-$C_6$)-alkyl or $Het^1$-S(O)$_p$—($C_1$-$C_6$)-alkyl, where $Het^1$ has the meaning mentioned above and where each of these radicals is unsubstituted in the acyclic moiety or substituted by one or more identical or different radicals $R^A$ and unsubstituted in the cyclic moiety or substituted by one or more identical or different radicals $R^B$ and p in each case represents 0, 1 or 2, where $R^A$ and $R^B$ each have the meaning given above, $R^{aa}$ has the meaning given above, and where $R^{aa}$ preferably independently represents a radical selected from the group consisting of hydrogen, OH, ($C_1$-$C_6$)-alkyl, ($C_1$-$C_4$)-haloalkyl, ($C_2$-$C_6$)-alkenyl, ($C_2$-$C_6$)-alkynyl, ($C_1$-$C_6$)-alkoxy, ($C_1$-$C_6$)-alkoxy-($C_1$-$C_6$)-alkyl, ($C_1$-$C_6$)-alkoxy-($C_1$-$C_6$)-alkyloxy, ($C_1$-$C_4$)-haloalkoxy, ($C_1$-$C_4$)-haloalkoxy-($C_1$-$C_6$)-alkyl, ($C_1$-$C_4$)-haloalkoxy-($C_1$-$C_6$)-alkoxy, ($C_3$-$C_6$)-alkenyloxy, ($C_3$-$C_6$)-alkenyloxy-($C_1$-$C_6$)-alkyl, ($C_3$-$C_6$)-alkenyloxy-($C_1$-$C_6$)-alkoxy, ($C_3$-$C_6$)-alkynyloxy, ($C_3$-$C_6$)-alkynyloxy-($C_1$-$C_6$)-alkyl, ($C_3$-$C_6$)-alkynyloxy-($C_1$-$C_6$)-alkoxy, —NR*R**, where R* and R** are as defined above, tri-[($C_1$-$C_4$)alkyl]silyl, tri-[($C_1$-$C_4$)-alkyl]silyl-($C_1$-$C_6$)-alkyl, tri-[($C_1$-$C_4$)-alkyl]silyl-($C_1$-$C_6$)-alkoxy, ($C_3$-$C_6$)-cycloalkyl, ($C_3$-$C_6$)-cycloalkoxy, ($C_3$-$C_6$)-cycloalkyl-($C_1$-$C_8$)-alkyl, ($C_3$-$C_6$)-cycloalkyl-($C_1$-$C_8$)-alkoxy, ($C_5$-$C_6$)-cycloalkenyl, ($C_5$-$C_6$)-cycloalkenyl-($C_1$-$C_6$)-alkyl, ($C_5$-$C_6$)-cycloalkenyloxy, ($C_5$-$C_6$)-cycloalkynyl, ($C_5$-$C_6$)-cycloalkynyl-($C_1$-$C_6$)-alkyl, ($C_5$-$C_6$)-cycloalkynyl-($C_1$-$C_6$)-alkoxy, phenyl, phenyl-($C_1$-$C_6$)-alkyl, phenyl-($C_1$-$C_6$)-alkoxy, phenoxy, phenoxy-($C_1$-$C_6$)-alkyl, phenoxy-($C_1$-$C_6$)-alkoxy, phenylthio, phenyl-S(O)$_p$—($C_1$-$C_6$)-alkyl, phenyl-S(O)$_p$—($C_1$-$C_6$)-alkoxy, where p independently of the others in each case represents 0, 1 or 2, phenylamino, phenylamino-($C_1$-$C_6$)-alkyl, phenylamino-($C_1$-$C_6$)-alkoxy or a 5- or 6-membered monocyclic or 9- or 10-membered bicyclic heterocycle which is optionally attached via an alkylene group or an alkoxy group and contains 1, 2, 3 or 4 heteroatoms selected from the group consisting of O, N and S, where each of the cyclic radicals $R^{aa}$ mentioned is optionally substituted in the cyclic moiety by one or more identical or different radicals selected from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy.

For reasons of higher herbicidal activity, better selectivity and better or easier handling, inter alia, compounds of the formula (I) according to the invention and compounds of the formula (I) to be used according to the invention and/or salts thereof in which $R^1$=H (hydrogen), preferably compounds of the formula (Ia) defined below, are particularly preferable in the context of the present invention.

Particular preference is likewise given to compounds of the formula (I) according to the invention and compounds of the formula (I) to be used according to the invention and/or salts thereof which, under application conditions, comparatively more easily lead to a compound of the formula (I) where $R^1$=H, for example by degradation or hydrolyzis.

In this case, the actual structure of group $R^1$ is not critical, where—as mentioned—preferably under the application conditions—for example by (enzymatic) degradation, cleavage or hydrolyzis—at least to some extend a compound of the formula (I) where $R^1$=H, preferably a compound of the formula (Ia) defined below, is formed.

In the context of what was discussed above, in a preferred aspect R' represents hydrogen or a group selected from the group consisting of —C(=O)—$R^C$, —C(=O)—O—$R^C$, —C(=O)—S—$R^C$, —C(=S)—S—$R^C$ and —C(=O)—NR*R**, particularly preferably hydrogen or a group —C(=O)—$R^C$, where $R^C$, R* and R** each have the meaning defined above, preferably each have one of the meanings given above as being preferred.

Especially preferably, $R^C$ represents hydrogen or a group selected from the group consisting of —C(=O)—$R^C$ and —C(=O)—O—$R^C$, here in turn particularly preferably hydrogen or —C(=O)—$R^C$, where $R^C$ preferably comprises a total of 1 to 16 carbon atoms, with preference a total of 1 to 12 carbon atoms.

Particularly preferably, $R^C$ in each case particularly preferably represents a radical selected from the group consisting of:
(i) hydrogen, unsubstituted ($C_1$-$C_8$)-alkyl, unsubstituted ($C_2$-$C_8$)-alkenyl, unsubstituted ($C_2$-$C_8$)-alkynyl, substituted ($C_1$-$C_8$)-alkyl, substituted ($C_2$-$C_8$)-alkenyl and substituted ($C_2$-$C_8$)-alkynyl, where each of these substituted radicals is substituted by one or more radicals from the group consisting of halogen, cyano, hydroxyl, ($C_1$-$C_4$)-alkoxy, ($C_2$-$C_6$)-alkenyloxy, ($C_1$-$C_4$)-haloalkoxy, ($C_1$-$C_4$)-alkoxy-($C_1$-$C_6$)alkoxy, ($C_1$-$C_6$)-alkylthio, ($C_1$-$C_6$)-haloalkylthio, ($C_1$-$C_6$)-alkylsulphinyl, ($C_1$-$C_6$)-alkylsulphonyl, ($C_1$-$C_8$)-haloalkylsulphonyl and tri-[($C_1$-$C_4$)-alkyl]silyl,
and (ii) ($C_3$-$C_8$)-cycloalkyl, ($C_5$-$C_8$)-cycloalkenyl, phenyl, phenyl-($C_1$-$C_6$)-alkyl, ($C_3$-$C_8$)-cycloalkyloxy-($C_1$-$C_6$)-alkyl, phenoxy-($C_1$-$C_6$)-alkyl, $Het^1$, $Het^1$-($C_1$-$C_6$)-alkyl, $Het^1$-O—($C_1$-$C_6$)-alkyl, where $Het^1$ has the meaning mentioned above and where each of these radicals is unsubstituted in the acyclic moiety or substituted by one or more identical or different radicals $R^A$ and unsubstituted in the cyclic moiety or substituted by one or more identical or different radicals $R^B$, where $R^A$ and $R^B$ each have the meaning given above, where in turn $R^A$ and $R^B$ preferably have the following meaning:

$R^A$ independently of any other radicals $R^A$ present is selected from the group consisting of halogen, cyano, hydroxy and ($C_1$-$C_4$)-alkoxy, and $R^B$ independently of any other radicals $R^B$ present is selected from the group consisting of halogen, cyano, hydroxyl, nitro, ($C_1$-$C_6$)-alkyl, ($C_1$-$C_6$)-haloalkyl, cyano-($C_1$-$C_6$)-alkyl, hydroxy-($C_1$-$C_6$)-alkyl, ($C_2$-$C_8$)-alkenyl, ($C_2$-$C_8$)-haloalkenyl, ($C_2$-$C_6$)-alkynyl, ($C_2$-$C_6$)-haloalkynyl, ($C_1$-$C_6$)-alkoxy, ($C_2$-$C_6$)-alkenyloxy, ($C_1$-$C_6$)-haloalkoxy, ($C_1$-$C_6$)-alkoxy-($C_1$-$C_4$)-alkyl, ($C_1$-$C_4$)-alkoxy-($C_1$-$C_4$)-alkoxy, ($C_1$-$C_4$)-haloalkoxy-($C_1$-$C_4$)-alkyl, ($C_1$-$C_4$)-haloalkoxy-($C_1$-$C_4$)-alkoxy, ($C_1$-$C_6$)-alkylthio, ($C_2$-$C_6$)-alkenylthio, ($C_1$-$C_6$)-alkylsulphinyl, ($C_1$-$C_6$)-haloalkylsulphinyl, ($C_1$-$C_6$)-alkylsulphonyl and ($C_1$-$C_6$)-haloalkylsulphonyl, where $R^C$ preferably comprises a total of 1 to 16 carbon atoms, with preference a total of 1 to 12 carbon atoms.

In formula (I), especially preferably $R^1$ represents hydrogen, —C(=O)—O—$R^C$ or —C(=O)—$R^C$, where the group $R^C$ is in each case selected from the group consisting of:

(i) unsubstituted ($C_1$-$C_6$)-alkyl, unsubstituted ($C_2$-$C_6$)-alkenyl, unsubstituted ($C_2$-$C_6$)-alkynyl, substituted ($C_1$-$C_6$)-alkyl, substituted ($C_2$-$C_6$)-alkenyl and substituted ($C_2$-$C_6$)-alkynyl, where each of these substituted radicals is substituted by one or more radicals from the group consisting of methyl, hydroxyl, fluorine and chlorine, (ii) ($C_3$-$C_6$)-cycloalkyl, ($C_3$-$C_6$)-cycloalkyloxy-($C_1$-$C_4$)-alkyl, phenyl, where each of these radicals is unsubstituted in the cyclic moiety or substituted by one or more identical or different radicals $R^B$, where $R^B$ is independently of any other radicals $R^B$ present selected from the group consisting of halogen (here preferably fluorine, chlorine, bromine), cyano, nitro and ($C_1$-$C_4$)-alkyl (here in turn preferably methyl), where $R^C$ preferably comprises a total of 1 to 12 carbon atoms, with preference a total of 1 to 10 carbon atoms.

In formula (I), $R^1$ especially preferably represents hydrogen or a group selected from the group consisting of:
acetyl, propanoyl, butanoyl, pentanoyl, hexanoyl, 2-methylpropanoyl (=isopropanoyl), 2,2-difluoroacetyl, 2,2,2-trifluoroacetyl, C(=O)OMe, cyclopropanecarbonyl, 1-methylcyclopropanecarbonyl, acryl, prop-2-ynoyl, but-2-ynoyl, 2-methylacryl, benzoyl, 4-chlorobenzoyl, 3-chlorobenzoyl, 2-chlorobenzoyl, 4-fluorobenzoyl, 3-fluorobenzoyl, 2-fluorobenzoyl, 2,2-dimethylpropanoyl (=pivaloyl), 3,3-dimethylbutanoyl, 2-nitrobenzoyl, 2-fluoroacetyl, 2-chloroacetyl, 2-bromoacetyl, 2,2-dichloroacetyl, 2-methoxyacetyl, 2,6-difluorobenzoyl, C(O)C(=O)OMe and C(O)$CH_2$C(O)OMe.

In formula (I), $R^1$ especially preferably represents hydrogen or a group selected from the group consisting of:
acetyl, propanoyl, butanoyl, pentanoyl, hexanoyl, 2-methylpropanoyl (=isopropanoyl), 2,2-difluoroacetyl, 2,2,2-trifluoroacetyl, C(=O)OMe, cyclopropanecarbonyl, 1-methylcyclopropanecarbonyl, acryl, prop-2-ynoyl, but-2-ynoyl, 2-methylacryl, benzoyl, 4-chlorobenzoyl, 3-chlorobenzoyl, 2-chlorobenzoyl, 4-fluorobenzoyl, 3-fluorobenzoyl, 2-fluorobenzoyl, 2,2-dimethylpropanoyl (=pivaloyl), 3,3-dimethylbutanoyl and 2-nitrobenzoyl.

In a preferred embodiment of the present invention, m+n>0, i.e. preferably at least one of the radicals $R^2$ and $R^3$ does not represent hydrogen.

In a preferred embodiment of the present invention, m+n>1, i.e. preferably at least two radicals $R^2$, at least two radicals $R^3$ or at least one radical $R^2$ and at least one radical $R^3$ do not represent hydrogen.

In particularly preferred compounds of the formula (I) according to the invention and compounds of the formula (I) used according to the invention, n is greater than or equal to 1 and one or more radicals $R^2$ represent halogen, preferably halogen selected from the group consisting of F, Cl and Br.

In particularly preferred compounds of the formula (I) according to the invention and compounds of the formula (I) used according to the invention, m is greater than or equal to 1 and one or more radicals $R^3$ represent halogen, preferably halogen selected from the group consisting of F, Cl and Br.

More preference is given to compounds of the formula (I) according to the invention and compounds of the formula (I) to be used according to the invention or salts thereof in which ($R^2$)$_n$ represents n substituents $R^2$,
where $R^2$ (if n=1) or each of the substituents $R^2$ (if n is greater than 1) independently of the others represents halogen, cyano, nitro, ($C_1$-$C_6$)-alkyl, ($C_1$-$C_6$)-alkoxy, ($C_1$-$C_6$)-alkylthio, ($C_1$-$C_6$)-alkylsulphinyl, ($C_1$-$C_6$)-alkylsulphonyl, ($C_1$-$C_6$)-haloalkyl, ($C_2$-$C_6$)-haloalkenyl, ($C_1$-$C_6$)-haloalkoxy, ($C_1$-$C_6$)-haloalkylthio, ($C_1$-$C_6$)-haloalkylsulphinyl, ($C_1$-$C_6$)-haloalkylsulphonyl, ($C_2$-$C_6$)-alkenyl, ($C_2$-$C_6$)-alkynyl, tri-[($C_1$-$C_4$)-alkyl]silyl or tri-[($C_1$-$C_4$)-alkyl]silyl-($C_1$-$C_4$)alkyl, or where in each case two groups $R^2$ directly adjacent to one another at the ring together represent a group of the formula —$Z^1$-A*-$Z^2$ in which A* represents an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^1$ represents a direct bond, O or S and $Z^2$ represents a direct bond, O or S, where the group —$Z^1$-A*-$Z^2$ together with the carbon atoms, attached to the group, of the phenyl ring form a fused-on 5- or 6-membered ring, and/or ($R^3$)$_m$ represents m substituents $R^3$,
where $R^3$ (if m=1) or each of the substituents $R^3$ (if m is greater than 1) independently of the others represents halogen, cyano, nitro, ($C_1$-$C_6$)-alkyl, ($C_1$-$C_6$)-alkoxy, ($C_1$-$C_6$)-alkylthio, ($C_1$-$C_6$)-alkylsulphinyl, ($C_1$-$C_6$)-alkyl sulphonyl, ($C_1$-$C_6$)-haloalkyl, ($C_2$-$C_6$)-haloalkenyl, ($C_1$-$C_6$)-haloalkoxy, ($C_1$-$C_6$)-haloalkylthio, ($C_1$-$C_6$)-haloalkylsulphinyl, ($C_1$-$C_6$)-haloalkylsulphonyl, ($C_2$-$C_6$)-alkenyl, ($C_2$-$C_6$)-alkynyl, NR*R, tri-[($C_1$-$C_4$)-alkyl]silyl or tri-[($C_1$-$C_4$)-alkyl]silyl-($C_1$-$C_4$)-alkyl, or where in each case two groups $R^3$ directly adjacent to one another at the ring together represent a group of the formula —$Z^3$-A-$Z^4$ in which A represents an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^3$ represents a direct bond, O or S and $Z^4$ represents a direct bond, O or S, where the group —$Z^3$-A-$Z^4$ together with the carbon atoms, attached to the group, of the phenyl ring form a fused-on 5- or 6-membered ring, R*, R** each independently of one another or together with the nitrogen atom have the meaning given above, n, m independently of one another each represent 0, 1, 2, 3, 4 or 5, preferably 0, 1, 2 or 3, in particular 0, 1 or 2.

More preference is given to compounds of the formula (I) according to the invention and compounds of the formula (I) to be used according to the invention or salts thereof in which ($R^2$)$_n$ represents n substituents $R^2$, where, in the case that n=1, the substituent $R^2$ or, in the case that n is greater than 1, each of the substituents $R^2$ independently of the others represents halogen, cyano, nitro, ($C_1$-$C_4$)-alkyl, ($C_1$-$C_4$)-alkoxy, ($C_1$-$C_4$)-alkylthio, ($C_1$-$C_4$)-alkylsulphinyl, ($C_1$-$C_4$)-alkylsulphonyl, ($C_1$-$C_4$)-haloalkyl, ($C_2$-$C_4$)-haloalkenyl, ($C_1$-$C_4$)-haloalkoxy, ($C_1$-$C_4$)-haloalkylthio, ($C_1$-$C_4$)-haloalkylsulphinyl, ($C_1$-$C_4$)-haloalkylsulphonyl, ($C_2$-$C_4$)-alkenyl, ($C_2$-$C_4$)-alkynyl, tri-[($C_1$-$C_4$)-alkyl]silyl or tri-[($C_1$-$C_4$)-alkyl]silyl-($C_1$-$C_4$)-alkyl and n represents 0, 1, 2, 3, 4 or 5, preferably 0, 1, 2 or 3, in particular 0, 1 or 2, and/or ($R^3$)$_m$ represents m substituents $R^3$, where, in the case that m=1, the substituent $R^3$, or, in the case that m is greater than 1, each of the substituents $R^3$ independently of the others represents halogen, cyano, nitro, ($C_1$-$C_4$)-alkyl, ($C_1$-$C_4$)-alkoxy, ($C_1$-$C_4$)-alkylthio, ($C_1$-$C_4$)-alkylsulphinyl, ($C_1$-$C_4$)-alkylsulphonyl, ($C_1$-$C_4$)-haloalkyl, ($C_2$-$C_4$)-haloalkenyl, ($C_1$-$C_4$)-haloalkoxy, ($C_1$-$C_4$)-haloalkylthio, ($C_1$-$C_4$)-haloalkylsulphinyl, ($C_1$-$C_4$)-haloalkylsulphonyl, ($C_2$-$C_6$)-alkenyl, ($C_2$-$C_6$)-alkynyl or tri-[($C_1$-$C_4$)-alkyl]silyl-$Z^b$—, where $Z^b$=a covalent bond or ($C_1$-$C_4$)-alkylene, or in each case two groups $R^3$ directly adjacent to one another at the ring together represent a group of the formula —$Z^3$-A-$Z^4$ where A represents an alkylene group which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^3$ represents O or S, and $Z^4$ represents O or S, where the group —$Z^3$-A**-$Z^4$ together with the carbon atoms, attached to the group, of the phenyl ring form a fused-on 5- or 6-membered ring, m represents 0, 1, 2, 3, 4 or 5, preferably 0, 1, 2 or 4, in particular 0, 1 or 2 or 3.

More preference is given to compounds of the formula (I) according to the invention and compounds of the formula (I) to be used according to the invention or salts thereof in which ($R^2$)$_n$ represents n substituents $R^2$, where, in the case that n=1, the substituent $R^2$ or, in the case that n is greater than 1, each of the substituents $R^2$ independently of the others represents fluorine, chlorine, bromine, iodine, cyano, nitro, methyl, ethyl, methoxy, methylthio, methylsulphinyl, methylsulphonyl, trifluoromethyl, trifluoromethoxy, trifluoroalkylthio, trifluoromethylsulphinyl or trifluoromethylsulphonyl, and ($R^3$)$_m$ represents m substituents $R^3$, where, in the case that m=1, the substituent $R^3$ or, in the case that m is greater than 1, each of the substituents $R^3$ independently of the others represents fluorine, chlorine, bromine, iodine, cyano, nitro, methyl, methoxy, methylthio, methylsulphinyl, methylsulphonyl, trifluoromethyl, trifluoromethoxy, trifluoroalkylthio, trifluoromethylsulphinyl or trifluoromethylsulphonyl, and m represents 0, 1, 2, 3, 4 or 5, preferably 0, 1, 2, 3 or 4, in particular 0, 1, 2 or 3, and n represents 0, 1, 2, 3, 4 or 5, preferably 0, 1, 2 or 3, in particular 0, 1 or 2.

Particular preference is given to compounds of the formula (I) according to the invention and compounds of the formula (I) to be used according to the invention or salts thereof in which ($R^2$)$_n$ represents 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-$CF_3$, 3-$CF_3$, 4-$CF_3$, 2-methoxy, 3-methoxy, 4-methoxy, 2-ethoxy, 3-ethoxy, 4-ethoxy, 2-methylthio, 3-methylthio, 4-methylthio, 2-methylsulphinyl, 3-methylsulphinyl, 4-methylsulphinyl, 2-methylsulphonyl, 3-methylsulphonyl, 4-methylsulphonyl, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-3-F), (3-Br-4-F), (3-Br-5-F), (4-Br-3-Cl), (3-Br-4-Cl), (4-CN-3-F), (3-CN-4-F), (3-CN-5-F), (3-CN-3-Cl), (3-CN-4-Cl), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or (2,6-$F_2$-4-Cl), and/or ($R^3$)$_m$ 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-$CF_3$, 3-$CF_3$, 4-$CF_3$, 2-methoxy, 3-methoxy, 4-methoxy, 2-ethoxy, 3-ethoxy, 4-ethoxy, 2-methylthio, 3-methylthio, 4-methylthio, 2-methylsulphinyl, 3-methylsulphinyl, 4-methylsulphinyl, 2-methylsulphonyl, 3-methylsulphonyl, 4-methylsulphonyl, 2-nitro, 3-nitro, 4-nitro, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, 2,5-dicyano, 2,6-dicyano, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-2-F), (4-Br-3-F), (4-CN-3-F), (4-$NO_2$-3-F), (4-OMe-3-F), (3-CN-4-F), (3-$NO_2$-4-F), (3-CN-4-

Cl), (3-$NO_2$-4-Cl), (5-CN-2-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or (2,6-$F_2$-4-Cl).

The present invention furthermore provides the compounds of the formula (Ib) and/or salts thereof

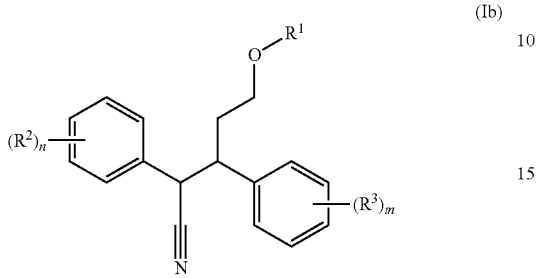
(Ib)

in which $R^1$ represents hydrogen or a hydrolyzable radical, where the hydrolyzable radical is preferably an acyl radical, particularly preferably, $R^1$ represents hydrogen or a group selected from the group consisting of —C(=O)—$R^C$ and —C(=O)—O—$R^C$, here in turn particularly preferably hydrogen or —C(=O)—$R^C$, where $R^C$ preferably comprises a total of 1 to 16 carbon atoms, with preference a total of 1 to 12 carbon atoms, and particularly preferably $R^C$ has the preferred or particularly preferred meaning defined above, $(R^2)_n$ represents n substituents $R^2$, where $R^2$ (if n=1) or each of the substituents $R^2$ (if n is greater than 1) independently of the others represents halogen, cyano, nitro, ($C_1$-$C_8$)-alkyl, ($C_1$-$C_8$)-alkoxy, ($C_1$-$C_8$)-alkylthio, ($C_1$-$C_8$)-alkylsulphinyl, ($C_1$-$C_8$)-alkylsulphonyl, ($C_1$-$C_6$)-haloalkyl, ($C_2$-$C_6$)-haloalkenyl, ($C_1$-$C_6$)-haloalkoxy, ($C_1$-$C_6$)-haloalkylthio, ($C_1$-$C_6$)-haloalkylsulphinyl, ($C_1$-$C_6$)-haloalkylsulphonyl, ($C_2$-$C_6$)-alkenyl, ($C_2$-$C_6$)-alkynyl, tri-[($C_1$-$C_4$)-alkyl]silyl or tri-[($C_1$-$C_4$)-alkyl]silyl-($C_1$-$C_4$)-alkyl, or in each case two $R^2$ immediately adjacent to one another at the ring together represent a group of the formula —$Z^1$-$A^*$-$Z^2$ in which $A^*$ represents an alkylene group having 1 to 4 carbon atoms which is optionally substituted by one or more radicals selected from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^1$ represents a direct bond, O or S and
$Z^2$ represents a direct bond, O or S, where the group —$Z^1$-$A^*$-$Z^2$ together with the carbon atoms, attached to this group, of the phenyl ring form a 5- or 6-membered ring, and $(R^3)_m$ represents m substituents $R^3$, where $R^3$ (if m=1) or each of the substituents $R^3$ (if m is greater than 1) independently of the others represents halogen, cyano, nitro, ($C_1$-$C_8$)-alkyl, ($C_1$-$C_8$)-alkoxy, ($C_1$-$C_8$)-alkylthio, ($C_1$-$C_8$)-alkylsulphinyl, ($C_1$-$C_8$)-alkylsulphonyl, ($C_1$-$C_6$)-haloalkyl, ($C_2$-$C_6$)-haloalkenyl, ($C_1$-$C_6$)-haloalkoxy, ($C_1$-$C_6$)-haloalkylthio, ($C_1$-$C_6$)-haloalkylsulphinyl, ($C_1$-$C_6$)-haloalkylsulphonyl, ($C_2$-$C_6$)-alkenyl, ($C_2$-$C_6$)-alkynyl, tri-[($C_1$-$C_4$)-alkyl]silyl-($C_1$-$C_4$)-alkyl or —NR*R**, where R* and R** independently of one another and independently of any further radicals —NR*R** present are in each case selected from the group consisting of H, ($C_1$-$C_8$)-alkyl, ($C_2$-$C_8$)-alkenyl, ($C_2$-$C_8$)-alkynyl, ($C_1$-$C_4$)-alkoxy-($C_1$-$C_4$)-alkyl, ($C_1$-$C_6$)-alkanoyl, [($C_1$-$C_4$)-haloalkyl]-carbonyl, [($C_1$-$C_4$)-alkoxy]-carbonyl, [($C_1$-$C_4$)-haloalkoxy]-carbonyl, ($C_3$-$C_6$)-cycloalkyl, ($C_3$-$C_6$)-cycloalkyl-($C_1$-$C_4$)-alkyl, ($C_3$-$C_6$)-cycloalkenyl, ($C_3$-$C_6$)-cycloalkenyl-($C_1$-$C_4$)-alkyl, phenyl and phenyl-($C_1$-$C_4$)-alkyl, where each of the ($C_3$-$C_6$)-cycloalkyl, ($C_3$-$C_6$)-cycloalkyl-($C_1$-$C_4$)-alkyl, ($C_3$-$C_6$)-cycloalkenyl, ($C_3$-$C_6$)-cycloalkenyl-($C_1$-$C_4$)-alkyl, phenyl and phenyl-($C_1$-$C_4$)-alkyl radicals mentioned is optionally substituted in the cycle by one or more identical or different radicals $R^{bb}$, where $R^{bb}$ in each case represents halogen, ($C_1$-$C_4$)-alkyl, ($C_1$-$C_4$)-haloalkyl, ($C_1$-$C_4$)-alkoxy or ($C_1$-$C_4$)-haloalkoxy and, in the case of ($C_3$-$C_6$)-cycloalkyl, ($C_3$-$C_6$)-cycloalkyl-($C_1$-$C_4$)-alkyl, ($C_3$-$C_6$)-cycloalkenyl, ($C_3$-$C_6$)-cycloalkenyl-($C_1$-$C_4$)-alkyl, $R^{bb}$ may additionally represent oxo, or NR*R represents a 3- to 8-membered heterocycle which, in addition to this nitrogen atom, may optionally contain one or two further ring heteroatoms selected from the group consisting of N, O and S and which is unsubstituted or substituted by one or more radicals from the group consisting of ($C_1$-$C_4$)-alkyl, ($C_1$-$C_4$)-haloalkyl and oxo, or where in each case two groups $R^3$ directly adjacent to one another at the ring together represent a group of the formula —$Z^3$-$A^{}$-$Z^4$ in which $A^{**}$ represents an alkylene group having 1 to 4 carbon atoms which is optionally substituted by one or more radicals selected from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^3$ represents a direct bond, O or S and
$Z^4$ represents a direct bond, O or S, where the group —$Z^3$-$A^{**}$-$Z^4$ together with the carbon atoms, attached to this group, of the phenyl ring form a 5- or 6-membered ring, and n represents 0, 1, 2, 3, 4 or 5, preferably 0, 1, 2 or 3,
m represents 0, 1, 2, 3, 4 or 5, preferably 0, 1, 2 or 3,
except for compounds in which $R^1$=H and
n=1, m=0, $R^2$=4-$NO_2$,
n=1, m=0, $R^2$=2-$NO_2$,
n=1, m=1, $R^2$=4-$NO_2$ and $R^3$=4-$NO_2$, 4-OMe or 4-Br,
n=1, m=1, $R^2$=$R^3$=4-OMe,
n=1, m=1, $R^2$=$R^3$=4-O-benzyl,
n=1, m=1, $R^2$=$R^3$=4-(2-methoxyethoxy)methoxy.

The compounds disclosed in J. Med. Chem. 2005, 48, 6366-6378 and in Organic Letters 2010, 12, 3586-3589 do not from part of the subject matter of the present invention.

In preferred compounds of the formulae (I), (Ia) and (Ib) according to the invention or compounds formulae (I), (Ia) and (Ib) preferably used according to the invention, $R^2$=not 4-$NO_2$ and not 2-$NO_2$.

In preferred compounds of the formulae (I), (Ia) and (Ib) according to the invention or compounds of the formulae (I), (Ia) and (Ib) preferably used according to the invention, $R^3$=not 4-O-benzyl and not 4-(2-methoxyethoxy)methoxy.

In preferred compounds of the formulae (I), (Ia) and (Ib) according to the invention or compounds of the formulae (I), (Ia) and (Ib) preferably used according to the invention, $R^3$=not O-benzyl (OBn) and not (2-methoxyethoxy)methoxy (OMEM).

Preferred compounds according to the invention are compounds of the formula (Ia) shown below, (corresponding to compounds of the formula (Ib) in which the radical $R^1$=hydrogen), their salts and their esters

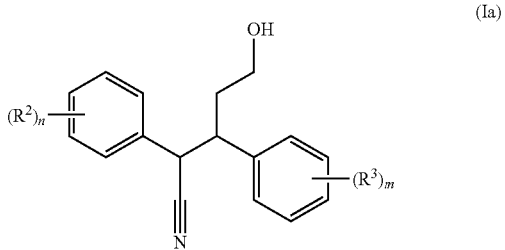

(Ia)

in which
($R^2$)$_n$ represents n substituents $R^2$, where $R^2$ (if n=1) or each of the substituents $R^2$ (if n is greater than 1) independently of the others represents halogen, cyano, ($C_1$-$C_8$)-alkyl, ($C_1$-$C_8$)-alkoxy, ($C_1$-$C_8$)-alkylthio, ($C_1$-$C_8$)-alkylsulphinyl, ($C_1$-$C_8$)-alkylsulphonyl, ($C_1$-$C_6$)-haloalkyl, ($C_2$-$C_6$)-haloalkenyl, ($C_1$-$C_6$)-haloalkoxy, ($C_1$-$C_6$)-haloalkylthio, ($C_1$-$C_6$)-haloalkylsulphinyl, ($C_1$-$C_6$)-haloalkylsulphonyl, ($C_2$-$C_6$)-alkenyl, ($C_2$-$C_6$)-alkynyl, tri-[($C_1$-$C_4$)-alkyl]silyl or tri-[($C_1$-$C_4$)-alkyl]silyl-($C_1$-$C_4$)-alkyl, or in each case two $R^2$ immediately adjacent to one another at the ring together represent a group of the formula —$Z^1$-$A^*$-$Z^2$ in which $A^*$ represents an alkylene group having 1 to 4 carbon atoms which is optionally substituted by one or more radicals selected from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^1$ represents a direct bond, O or S and
$Z^2$ represents a direct bond, O or S,
where the group —$Z^1$-$A^*$-$Z^2$ together with the carbon atoms, attached to this group, of the phenyl ring form a 5- or 6-membered ring, and ($R^3$)$_m$ represents m substituents $R^3$,
where $R^3$ (if m=1) or each of the substituents $R^3$ (if m is greater than 1) independently of the others represents halogen, cyano, nitro, ($C_1$-$C_8$)-alkyl, ($C_1$-$C_8$)-alkoxy, ($C_1$-$C_8$)-alkylthio, ($C_1$-$C_8$)-alkylsulphinyl, ($C_1$-$C_8$)-alkylsulphonyl, ($C_1$-$C_6$)-haloalkyl, ($C_2$-$C_6$)-haloalkenyl, ($C_1$-$C_6$)-haloalkoxy, ($C_1$-$C_6$)-haloalkylthio, ($C_1$-$C_6$)-haloalkylsulphinyl, ($C_1$-$C_6$)-haloalkylsulphonyl, ($C_2$-$C_6$)-alkenyl, ($C_2$-$C_6$)-alkynyl, tri-[($C_1$-$C_4$)-alkyl]silyl, tri-[($C_1$-$C_4$)-alkyl]silyl-($C_1$-$C_4$)-alkyl or —NR*R**, where R* and R** independently of one another and independently of any further radicals —NR*R** present are in each case selected from the group consisting of H, ($C_1$-$C_8$)-alkyl, ($C_2$-$C_8$)-alkenyl, ($C_2$-$C_8$)-alkynyl, ($C_1$-$C_4$)-alkoxy-($C_1$-$C_4$)-alkyl, ($C_1$-$C_6$)-alkanoyl, [($C_1$-$C_4$)-haloalkyl]-carbonyl, [($C_1$-$C_4$)-alkoxy]-carbonyl, [($C_1$-$C_4$)-haloalkoxy]-carbonyl, ($C_3$-$C_6$)-cycloalkyl, ($C_3$-$C_6$)-cycloalkyl-($C_1$-$C_4$)-alkyl, ($C_3$-$C_6$)-cycloalkenyl, ($C_3$-$C_6$)-cycloalkenyl-($C_1$-$C_4$)-alkyl, phenyl and phenyl-($C_1$-$C_4$)-alkyl, where each of the ($C_3$-$C_6$)-cycloalkyl, ($C_3$-$C_6$)-cycloalkyl-($C_1$-$C_4$)-alkyl, ($C_3$-$C_6$)-cycloalkenyl, ($C_3$-$C_6$)-cycloalkenyl-($C_1$-$C_4$)-alkyl, phenyl and phenyl-($C_1$-$C_4$)-alkyl radicals mentioned is optionally substituted in the cycle by one or more identical or different radicals $R^{bb}$, where $R^{bb}$ in each case represents halogen, ($C_1$-$C_4$)-alkyl, ($C_1$-$C_4$)-haloalkyl, ($C_1$-$C_4$)-alkoxy or ($C_1$-$C_4$)-haloalkoxy and, in the case of ($C_3$-$C_6$)-cycloalkyl, ($C_3$-$C_6$)-cycloalkyl-($C_1$-$C_4$)-alkyl, ($C_3$-$C_6$)-cycloalkenyl, ($C_3$-$C_6$)-cycloalkenyl-($C_1$-$C_4$)-alkyl, $R^{bb}$ may additionally represent oxo, or NR*R represents a 3- to 8-membered heterocycle which, in addition to this nitrogen atom, optionally contains one or two further ring heteroatoms selected from the group consisting of N, O and S and which is unsubstituted or substituted by one or more radicals selected from the group consisting of ($C_1$-$C_4$)-alkyl, ($C_1$-$C_4$)-haloalkyl and oxo, or where in each case two groups $R^3$ directly adjacent to one another at the ring together represent a group of the formula —$Z^3$-$A^{}$-$Z^4$ in which $A^{**}$ represents an alkylene group having 1 to 4 carbon atoms which is optionally substituted by one or more radicals selected from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^3$ represents a direct bond, O or S and
$Z^4$ represents a direct bond, O or S,
where the group —$Z^3$-$A^{**}$-$Z^4$ together with the carbon atoms, attached to this group, of the phenyl ring form a 5- or 6-membered ring, and n represents 0, 1, 2, 3, 4 or 5, preferably 0, 1, 2 or 3,
m represents 0, 1, 2, 3, 4 or 5, preferably 0, 1, 2 or 3,
except for compounds in which
n=1, m=1 and $R^2$=$R^3$=4-OMe,
n=1, m=1 and $R^2$=$R^3$=4-O-benzyl,
n=1, m=1 and $R^2$=$R^3$=4-(2-methoxyethoxy)methoxy.

Preferred compounds according to the invention correspond to the formula (Ia) and/or salts thereof

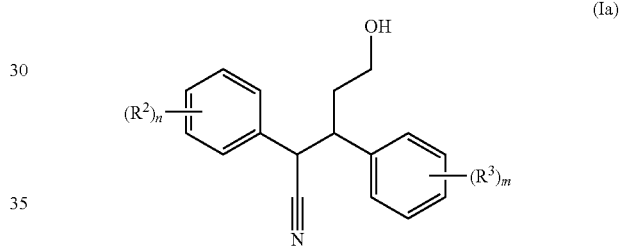

(Ia)

in which
($R^2$)$_n$ represents n substituents $R^2$, where $R^2$ (if n=1) or each of the substituents $R^2$ (if n is greater than 1) independently of the others represents halogen, cyano, ($C_1$-$C_8$)-alkyl, ($C_1$-$C_8$)-alkoxy, ($C_1$-$C_8$)-alkylthio, ($C_1$-$C_8$)-alkylsulphinyl, ($C_1$-$C_8$)-alkylsulphonyl, ($C_1$-$C_6$)-haloalkyl, ($C_2$-$C_6$)-haloalkenyl, ($C_1$-$C_6$)-haloalkoxy, ($C_1$-$C_6$)-haloalkylthio, ($C_1$-$C_6$)-haloalkylsulphinyl, ($C_1$-$C_6$)-haloalkylsulphonyl, ($C_2$-$C_6$)-alkenyl, ($C_2$-$C_6$)-alkynyl, tri-[($C_1$-$C_4$)-alkyl]silyl or tri-[($C_1$-$C_4$)-alkyl]silyl-($C_1$-$C_4$)-alkyl, or in each case two $R^2$ immediately adjacent to one another at the ring together represent a group of the formula —$Z^1$-$A^*$-$Z^2$ in which $A^*$ represents an alkylene group having 1 to 4 carbon atoms which is optionally substituted by one or more radicals selected from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^1$ represents a direct bond, O or S and
$Z^2$ represents a direct bond, O or S,
where the group —$Z^1$-$A^*$-$Z^2$ together with the carbon atoms, attached to this group, of the phenyl ring form a 5- or 6-membered ring, and ($R^3$)$_m$ represents m substituents $R^3$,
where $R^3$ (if m=1) or each of the substituents $R^3$ (if m is greater than 1) independently of the others represents halogen, cyano, nitro, ($C_1$-$C_8$)-alkyl, ($C_1$-$C_8$)-alkoxy, ($C_1$-$C_8$)-alkylthio, ($C_1$-$C_8$)-alkylsulphinyl, ($C_1$-$C_8$)-alkylsulphonyl, ($C_1$-$C_6$)-haloalkyl, ($C_2$-$C_6$)-haloalkenyl, ($C_1$-$C_6$)-haloalkoxy, ($C_1$-$C_6$)-haloalkylthio, ($C_1$-

$C_6$)-haloalkylsulphinyl, $(C_1-C_6)$-haloalkylsulphonyl, $(C_2-C_6)$-alkenyl, $(C_2-C_6)$-alkynyl, tri-$[(C_1-C_4)$-alkyl]silyl, tri-$[(C_1-C_4)$-alkyl]silyl-$(C_1-C_4)$-alkyl or —NR*R**, where R* and R** independently of one another and independently of any further radicals —NR*R** present are in each case selected from the group consisting of H, $(C_1-C_8)$-alkyl, $(C_2-C_8)$-alkenyl, $(C_2-C_8)$-alkynyl, $(C_1-C_4)$-alkoxy-$(C_1-C_4)$-alkyl, $(C_1-C_6)$-alkanoyl, $[(C_1-C_4)$-haloalkyl]-carbonyl, $[(C_1-C_4)$-alkoxy]-carbonyl, $[(C_1-C_4)$-haloalkoxy]-carbonyl, $(C_3-C_6)$-cycloalkyl, $(C_3-C_6)$-cycloalkyl-$(C_1-C_4)$-alkyl, $(C_3-C_6)$-cycloalkenyl, $(C_3-C_6)$-cycloalkenyl-$(C_1-C_4)$-alkyl, phenyl and phenyl-$(C_1-C_4)$-alkyl, where each of the $(C_3-C_6)$-cycloalkyl, $(C_3-C_6)$-cycloalkyl-$(C_1-C_4)$-alkyl, $(C_3-C_6)$-cycloalkenyl, $(C_3-C_6)$-cycloalkenyl-$(C_1-C_4)$-alkyl, phenyl and phenyl-$(C_1-C_4)$-alkyl radicals mentioned is optionally substituted in the cycle by one or more identical or different radicals $R^{bb}$, where $R^{bb}$ in each case represents halogen, $(C_1-C_4)$-alkyl, $(C_1-C_4)$-haloalkyl, $(C_1-C_4)$-alkoxy or $(C_1-C_4)$-haloalkoxy and, in the case of $(C_3-C_6)$-cycloalkyl, $(C_3-C_6)$-cycloalkyl-$(C_1-C_4)$-alkyl, $(C_3-C_6)$-cycloalkenyl, $(C_3-C_6)$-cycloalkenyl-$(C_1-C_4)$-alkyl, $R^{bb}$ may additionally represent oxo, or NR*R represents a 3- to 8-membered heterocycle which, in addition to this nitrogen atom, optionally contains one or two further ring heteroatoms selected from the group consisting of N, O and S and which is unsubstituted or substituted by one or more radicals selected from the group consisting of $(C_1-C_4)$-alkyl, $(C_1-C_4)$-haloalkyl and oxo, or where in each case two groups $R^3$ directly adjacent to one another at the ring together represent a group of the formula —$Z^3$-A-$Z^4$ in which A represents an alkylene group having 1 to 4 carbon atoms which is optionally substituted by one or more radicals selected from the group consisting of halogen, $(C_1-C_4)$-alkyl, $(C_1-C_4)$-haloalkyl, $(C_1-C_4)$-alkoxy and $(C_1-C_4)$-haloalkoxy, $Z^3$ represents a direct bond, O or S and $Z^4$ represents a direct bond, O or S, where the group —$Z^3$-A-$Z^4$ together with the carbon atoms, attached to this group, of the phenyl ring form a 5- or 6-membered ring, and n represents 0, 1, 2, 3, 4 or 5, preferably 0, 1, 2 or 3, m represents 0, 1, 2, 3, 4 or 5, preferably 0, 1, 2 or 3, except for compounds in which n=1, m=1 and $R^2=R^3$=4-OMe, n=1, m=1 and $R^2=R^3$=4-O-benzyl, n=1, m=1 and $R^2=R^3$=4-(2-methoxyethoxy)methoxy.

Preferred radicals $(R^2)_n$ and $(R^3)_m$ are listed in Table 1 below, where in each case preferably the radical R1=H (hydrogen), which define compounds of the formulae (I) and (Ia) preferably used according to the invention and preferred compounds of the formulae (I) and (Ia).

Abbreviations and annotations used herein are discussed in detail in the Example Section.

TABLE 1

Preferred meanings of the radicals $(R^2)_n$ and $(R^3)_m$ in the formulae (I), (Ib) and (Ia):

| No. | $(R^2)_n$ | $(R^3)_m$ |
|---|---|---|
| 1 | H | 2,6-$F_2$ |
| 2 | 2-F | 2,6-$F_2$ |
| 3 | 3-F | 2,6-$F_2$ |
| 4 | 4-F | 2,6-$F_2$ |

TABLE 1-continued

Preferred meanings of the radicals $(R^2)_n$ and $(R^3)_m$ in the formulae (I), (Ib) and (Ia):

| No. | $(R^2)_n$ | $(R^3)_m$ |
|---|---|---|
| 5 | 3-Cl | 2,6-$F_2$ |
| 6 | 4-Cl | 2,6-$F_2$ |
| 7 | 3-Br | 2,6-$F_2$ |
| 8 | 4-Br | 2,6-$F_2$ |
| 9 | 3-I | 2,6-$F_2$ |
| 10 | 3-CN | 2,6-$F_2$ |
| 11 | 4-CN | 2,6-$F_2$ |
| 12 | 3-$NO_2$ | 2,6-$F_2$ |
| 13 | 3-Me | 2,6-$F_2$ |
| 14 | 4-Me | 2,6-$F_2$ |
| 15 | 2,3-$F_2$ | 2,6-$F_2$ |
| 16 | 2,4-$F_2$ | 2,6-$F_2$ |
| 17 | 2,5-$F_2$ | 2,6-$F_2$ |
| 18 | 2,6-$F_2$ | 2,6-$F_2$ |
| 19 | 3,4-$F_2$ | 2,6-$F_2$ |
| 20 | 3,5-$F_2$ | 2,6-$F_2$ |
| 21 | 3,4,5-$F_3$ | 2,6-$F_2$ |
| 22 | 3-F, 4-Cl | 2,6-$F_2$ |
| 23 | 3-F, 4-Br | 2,6-$F_2$ |
| 24 | 3-CN, 4-F | 2,6-$F_2$ |
| 25 | 3-Br, 4-F | 2,6-$F_2$ |
| 26 | 3-Cl, 4-F | 2,6-$F_2$ |
| 27 | 3,4-$Cl_2$ | 2,6-$F_2$ |
| 28 | H | 2,5-$F_2$ |
| 29 | 2-F | 2,5-$F_2$ |
| 30 | 3-F | 2,5-$F_2$ |
| 31 | 4-F | 2,5-$F_2$ |
| 32 | 3-Cl | 2,5-$F_2$ |
| 33 | 4-Cl | 2,5-$F_2$ |
| 34 | 3-Br | 2,5-$F_2$ |
| 35 | 4-Br | 2,5-$F_2$ |
| 36 | 3-I | 2,5-$F_2$ |
| 37 | 3-CN | 2,5-$F_2$ |
| 38 | 4-CN | 2,5-$F_2$ |
| 39 | 3-$NO_2$ | 2,5-$F_2$ |
| 40 | 3-Me | 2,5-$F_2$ |
| 41 | 4-Me | 2,5-$F_2$ |
| 42 | 2,3-$F_2$ | 2,5-$F_2$ |
| 43 | 2,4-$F_2$ | 2,5-$F_2$ |
| 44 | 2,5-$F_2$ | 2,5-$F_2$ |
| 45 | 2,6-$F_2$ | 2,5-$F_2$ |
| 46 | 3,4-$F_2$ | 2,5-$F_2$ |
| 47 | 3,5-$F_2$ | 2,5-$F_2$ |
| 48 | 3,4,5-$F_3$ | 2,5-$F_2$ |
| 49 | 3-F, 4-Cl | 2,5-$F_2$ |
| 50 | 3-F, 4-Br | 2,5-$F_2$ |
| 51 | 3-CN, 4-F | 2,5-$F_2$ |
| 52 | 3-Br, 4-F | 2,5-$F_2$ |
| 53 | 3-Cl, 4-F | 2,5-$F_2$ |
| 54 | 3,4-$Cl_2$ | 2,5-$F_2$ |
| 55 | H | 2,3,6-$F_3$ |
| 56 | 2-F | 2,3,6-$F_3$ |
| 57 | 3-F | 2,3,6-$F_3$ |
| 58 | 4-F | 2,3,6-$F_3$ |
| 59 | 3-Cl | 2,3,6-$F_3$ |
| 60 | 4-Cl | 2,3,6-$F_3$ |
| 61 | 3-Br | 2,3,6-$F_3$ |
| 62 | 4-Br | 2,3,6-$F_3$ |
| 63 | 3-I | 2,3,6-$F_3$ |
| 64 | 3-CN | 2,3,6-$F_3$ |
| 65 | 4-CN | 2,3,6-$F_3$ |
| 66 | 3-$NO_2$ | 2,3,6-$F_3$ |
| 67 | 3-Me | 2,3,6-$F_3$ |
| 68 | 4-Me | 2,3,6-$F_3$ |
| 69 | 2,3-$F_2$ | 2,3,6-$F_3$ |
| 70 | 2,4-$F_2$ | 2,3,6-$F_3$ |
| 71 | 2,5-$F_2$ | 2,3,6-$F_3$ |
| 72 | 2,6-$F_2$ | 2,3,6-$F_3$ |
| 73 | 3,4-$F_2$ | 2,3,6-$F_3$ |
| 74 | 3,5-$F_2$ | 2,3,6-$F_3$ |
| 75 | 3,4,5-$F_3$ | 2,3,6-$F_3$ |
| 76 | 3-F, 4-Cl | 2,3,6-$F_3$ |
| 77 | 3-F, 4-Br | 2,3,6-$F_3$ |
| 78 | 3-CN, 4-F | 2,3,6-$F_3$ |
| 79 | 3-Br, 4-F | 2,3,6-$F_3$ |

TABLE 1-continued

Preferred meanings of the radicals $(R^2)_n$ and $(R^3)_m$ in the formulae (I), (Ib) and (Ia):

| No. | $(R^2)_n$ | $(R^3)_m$ |
|---|---|---|
| 80 | 3-Cl, 4-F | 2,3,6-F$_3$ |
| 81 | 3,4-Cl$_2$ | 2,3,6-F$_3$ |
| 82 | H | 2,4,6-F$_3$ |
| 83 | 2-F | 2,4,6-F$_3$ |
| 84 | 3-F | 2,4,6-F$_3$ |
| 85 | 4-F | 2,4,6-F$_3$ |
| 86 | 3-Cl | 2,4,6-F$_3$ |
| 87 | 4-Cl | 2,4,6-F$_3$ |
| 88 | 3-Br | 2,4,6-F$_3$ |
| 89 | 4-Br | 2,4,6-F$_3$ |
| 90 | 3-I | 2,4,6-F$_3$ |
| 91 | 3-CN | 2,4,6-F$_3$ |
| 92 | 4-CN | 2,4,6-F$_3$ |
| 93 | 3-NO$_2$ | 2,4,6-F$_3$ |
| 94 | 3-Me | 2,4,6-F$_3$ |
| 95 | 4-Me | 2,4,6-F$_3$ |
| 96 | 2,3-F$_2$ | 2,4,6-F$_3$ |
| 97 | 2,4-F$_2$ | 2,4,6-F$_3$ |
| 98 | 2,5-F$_2$ | 2,4,6-F$_3$ |
| 99 | 2,6-F$_2$ | 2,4,6-F$_3$ |
| 100 | 3,4-F$_2$ | 2,4,6-F$_3$ |
| 101 | 3,5-F$_2$ | 2,4,6-F$_3$ |
| 102 | 3,4,5-F$_3$ | 2,4,6-F$_3$ |
| 103 | 3-F, 4-Cl | 2,4,6-F$_3$ |
| 104 | 3-F, 4-Br | 2,4,6-F$_3$ |
| 105 | 3-CN, 4-F | 2,4,6-F$_3$ |
| 106 | 3-Br, 4-F | 2,4,6-F$_3$ |
| 107 | 3-Cl, 4-F | 2,4,6-F$_3$ |
| 108 | 3,4-Cl$_2$ | 2,4,6-F$_3$ |
| 109 | H | 2,6-F$_2$, 4-Cl |
| 110 | 2-F | 2,6-F$_2$, 4-Cl |
| 111 | 3-F | 2,6-F$_2$, 4-Cl |
| 112 | 4-F | 2,6-F$_2$, 4-Cl |
| 113 | 3-Cl | 2,6-F$_2$, 4-Cl |
| 114 | 4-Cl | 2,6-F$_2$, 4-Cl |
| 115 | 3-Br | 2,6-F$_2$, 4-Cl |
| 116 | 4-Br | 2,6-F$_2$, 4-Cl |
| 117 | 3-I | 2,6-F$_2$, 4-Cl |
| 118 | 3-CN | 2,6-F$_2$, 4-Cl |
| 119 | 4-CN | 2,6-F$_2$, 4-Cl |
| 120 | 3-NO$_2$ | 2,6-F$_2$, 4-Cl |
| 121 | 3-Me | 2,6-F$_2$, 4-Cl |
| 122 | 4-Me | 2,6-F$_2$, 4-Cl |
| 123 | 2,3-F$_2$ | 2,6-F$_2$, 4-Cl |
| 124 | 2,4-F$_2$ | 2,6-F$_2$, 4-Cl |
| 125 | 2,5-F$_2$ | 2,6-F$_2$, 4-Cl |
| 126 | 2,6-F$_2$ | 2,6-F$_2$, 4-Cl |
| 127 | 3,4-F$_2$ | 2,6-F$_2$, 4-Cl |
| 128 | 3,5-F$_2$ | 2,6-F$_2$, 4-Cl |
| 129 | 3,4,5-F$_3$ | 2,6-F$_2$, 4-Cl |
| 130 | 3-F, 4-Cl | 2,6-F$_2$, 4-Cl |
| 131 | 3-F, 4-Br | 2,6-F$_2$, 4-Cl |
| 132 | 3-CN, 4-F | 2,6-F$_2$, 4-Cl |
| 133 | 3-Br, 4-F | 2,6-F$_2$, 4-Cl |
| 134 | 3-Cl, 4-F | 2,6-F$_2$, 4-Cl |
| 135 | 3,4-Cl$_2$ | 2,6-F$_2$, 4-Cl |
| 136 | H | 3,5-F$_2$ |
| 137 | 2-F | 3,5-F$_2$ |
| 138 | 3-F | 3,5-F$_2$ |
| 139 | 4-F | 3,5-F$_2$ |
| 140 | 3-Cl | 3,5-F$_2$ |
| 141 | 4-Cl | 3,5-F$_2$ |
| 142 | 3-Br | 3,5-F$_2$ |
| 143 | 4-Br | 3,5-F$_2$ |
| 144 | 3-I | 3,5-F$_2$ |
| 145 | 3-CN | 3,5-F$_2$ |
| 146 | 4-CN | 3,5-F$_2$ |
| 147 | 3-NO$_2$ | 3,5-F$_2$ |
| 148 | 3-Me | 3,5-F$_2$ |
| 149 | 4-Me | 3,5-F$_2$ |
| 150 | 2,3-F$_2$ | 3,5-F$_2$ |
| 151 | 2,4-F$_2$ | 3,5-F$_2$ |
| 152 | 2,5-F$_2$ | 3,5-F$_2$ |
| 153 | 2,6-F$_2$ | 3,5-F$_2$ |
| 154 | 3,4-F$_2$ | 3,5-F$_2$ |
| 155 | 3,5-F$_2$ | 3,5-F$_2$ |
| 156 | 3,4,5-F$_3$ | 3,5-F$_2$ |
| 157 | 3-F, 4-Cl | 3,5-F$_2$ |
| 158 | 3-F, 4-Br | 3,5-F$_2$ |
| 159 | 3-CN, 4-F | 3,5-F$_2$ |
| 160 | 3-Br, 4-F | 3,5-F$_2$ |
| 161 | 3-Cl, 4-F | 3,5-F$_2$ |
| 162 | 3,4-Cl$_2$ | 3,5-F$_2$ |
| 163 | H | 2,3-F$_2$ |
| 164 | 2-F | 2,3-F$_2$ |
| 165 | 3-F | 2,3-F$_2$ |
| 166 | 4-F | 2,3-F$_2$ |
| 167 | 3-Cl | 2,3-F$_2$ |
| 168 | 4-Cl | 2,3-F$_2$ |
| 169 | 3-Br | 2,3-F$_2$ |
| 170 | 4-Br | 2,3-F$_2$ |
| 171 | 3-I | 2,3-F$_2$ |
| 172 | 3-CN | 2,3-F$_2$ |
| 173 | 4-CN | 2,3-F$_2$ |
| 174 | 3-NO$_2$ | 2,3-F$_2$ |
| 175 | 3-Me | 2,3-F$_2$ |
| 176 | 4-Me | 2,3-F$_2$ |
| 177 | 2,3-F$_2$ | 2,3-F$_2$ |
| 178 | 2,4-F$_2$ | 2,3-F$_2$ |
| 179 | 2,5-F$_2$ | 2,3-F$_2$ |
| 180 | 2,6-F$_2$ | 2,3-F$_2$ |
| 181 | 3,4-F$_2$ | 2,3-F$_2$ |
| 182 | 3,5-F$_2$ | 2,3-F$_2$ |
| 183 | 3,4,5-F$_3$ | 2,3-F$_2$ |
| 184 | 3-F, 4-Cl | 2,3-F$_2$ |
| 185 | 3-F, 4-Br | 2,3-F$_2$ |
| 186 | 3-CN, 4-F | 2,3-F$_2$ |
| 187 | 3-Br, 4-F | 2,3-F$_2$ |
| 188 | 3-Cl, 4-F | 2,3-F$_2$ |
| 189 | 3,4-Cl$_2$ | 2,3-F$_2$ |
| 190 | H | 3,4-F$_2$ |
| 191 | 2-F | 3,4-F$_2$ |
| 192 | 3-F | 3,4-F$_2$ |
| 193 | 4-F | 3,4-F$_2$ |
| 194 | 3-Cl | 3,4-F$_2$ |
| 195 | 4-Cl | 3,4-F$_2$ |
| 196 | 3-Br | 3,4-F$_2$ |
| 197 | 4-Br | 3,4-F$_2$ |
| 198 | 3-I | 3,4-F$_2$ |
| 199 | 3-CN | 3,4-F$_2$ |
| 200 | 4-CN | 3,4-F$_2$ |
| 201 | 3-NO$_2$ | 3,4-F$_2$ |
| 202 | 3-Me | 3,4-F$_2$ |
| 203 | 4-Me | 3,4-F$_2$ |
| 204 | 2,3-F$_2$ | 3,4-F$_2$ |
| 205 | 2,4-F$_2$ | 3,4-F$_2$ |
| 206 | 2,5-F$_2$ | 3,4-F$_2$ |
| 207 | 2,6-F$_2$ | 3,4-F$_2$ |
| 208 | 3,4-F$_2$ | 3,4-F$_2$ |
| 209 | 3,5-F$_2$ | 3,4-F$_2$ |
| 210 | 3,4,5-F$_3$ | 3,4-F$_2$ |
| 211 | 3-F, 4-Cl | 3,4-F$_2$ |
| 212 | 3-F, 4-Br | 3,4-F$_2$ |
| 213 | 3-CN, 4-F | 3,4-F$_2$ |
| 214 | 3-Br, 4-F | 3,4-F$_2$ |
| 215 | 3-Cl, 4-F | 3,4-F$_2$ |
| 216 | 3,4-Cl$_2$ | 3,4-F$_2$ |
| 217 | H | 2-F |
| 218 | 2-F | 2-F |
| 219 | 3-F | 2-F |
| 220 | 4-F | 2-F |
| 221 | 3-Cl | 2-F |
| 222 | 4-Cl | 2-F |
| 223 | 3-Br | 2-F |
| 224 | 4-Br | 2-F |
| 225 | 3-I | 2-F |
| 226 | 3-CN | 2-F |
| 227 | 4-CN | 2-F |
| 228 | 3-NO$_2$ | 2-F |
| 229 | 3-Me | 2-F |

TABLE 1-continued

Preferred meanings of the radicals $(R^2)_n$ and $(R^3)_m$ in the formulae (I), (Ib) and (Ia):

| No. | $(R^2)_n$ | $(R^3)_m$ |
|---|---|---|
| 230 | 4-Me | 2-F |
| 231 | 2,3-F$_2$ | 2-F |
| 232 | 2,4-F$_2$ | 2-F |
| 233 | 2,5-F$_2$ | 2-F |
| 234 | 2,6-F$_2$ | 2-F |
| 235 | 3,4-F$_2$ | 2-F |
| 236 | 3,5-F$_2$ | 2-F |
| 237 | 3,4,5-F$_3$ | 2-F |
| 238 | 3-F, 4-Cl | 2-F |
| 239 | 3-F, 4-Br | 2-F |
| 240 | 3-CN, 4-F | 2-F |
| 241 | 3-Br, 4-F | 2-F |
| 242 | 3-Cl, 4-F | 2-F |
| 243 | 3,4-Cl$_2$ | 2-F |
| 244 | H | 2-Cl |
| 245 | 2-F | 2-Cl |
| 246 | 3-F | 2-Cl |
| 247 | 4-F | 2-Cl |
| 248 | 3-Cl | 2-Cl |
| 249 | 4-Cl | 2-Cl |
| 250 | 3-Br | 2-Cl |
| 251 | 4-Br | 2-Cl |
| 252 | 3-I | 2-Cl |
| 253 | 3-CN | 2-Cl |
| 254 | 4-CN | 2-Cl |
| 255 | 3-NO$_2$ | 2-Cl |
| 256 | 3-Me | 2-Cl |
| 257 | 4-Me | 2-Cl |
| 258 | 2,3-F$_2$ | 2-Cl |
| 259 | 2,4-F$_2$ | 2-Cl |
| 260 | 2,5-F$_2$ | 2-Cl |
| 261 | 2,6-F$_2$ | 2-Cl |
| 262 | 3,4-F$_2$ | 2-Cl |
| 263 | 3,5-F$_2$ | 2-Cl |
| 264 | 3,4,5-F$_3$ | 2-Cl |
| 265 | 3-F, 4-Cl | 2-Cl |
| 266 | 3-F, 4-Br | 2-Cl |
| 267 | 3-CN, 4-F | 2-Cl |
| 268 | 3-Br, 4-F | 2-Cl |
| 269 | 3-Cl, 4-F | 2-Cl |
| 270 | 3,4-Cl$_2$ | 2-Cl |
| 271 | H | 3-F |
| 272 | 2-F | 3-F |
| 273 | 3-F | 3-F |
| 274 | 4-F | 3-F |
| 275 | 3-Cl | 3-F |
| 276 | 4-Cl | 3-F |
| 277 | 3-Br | 3-F |
| 278 | 4-Br | 3-F |
| 279 | 3-I | 3-F |
| 280 | 3-CN | 3-F |
| 281 | 4-CN | 3-F |
| 282 | 3-NO$_2$ | 3-F |
| 283 | 3-Me | 3-F |
| 284 | 4-Me | 3-F |
| 285 | 2,3-F$_2$ | 3-F |
| 286 | 2,4-F$_2$ | 3-F |
| 287 | 2,5-F$_2$ | 3-F |
| 288 | 2,6-F$_2$ | 3-F |
| 289 | 3,4-F$_2$ | 3-F |
| 290 | 3,5-F$_2$ | 3-F |
| 291 | 3,4,5-F$_3$ | 3-F |
| 292 | 3-F, 4-Cl | 3-F |
| 293 | 3-F, 4-Br | 3-F |
| 294 | 3-CN, 4-F | 3-F |
| 295 | 3-Br, 4-F | 3-F |
| 296 | 3-Cl, 4-F | 3-F |
| 297 | 3,4-Cl$_2$ | 3-F |
| 298 | H | 3-Cl |
| 299 | 2-F | 3-Cl |
| 300 | 3-F | 3-Cl |
| 301 | 4-F | 3-Cl |
| 302 | 3-Cl | 3-Cl |
| 303 | 4-Cl | 3-Cl |
| 304 | 3-Br | 3-Cl |
| 305 | 4-Br | 3-Cl |
| 306 | 3-I | 3-Cl |
| 307 | 3-CN | 3-Cl |
| 308 | 4-CN | 3-Cl |
| 309 | 3-NO$_2$ | 3-Cl |
| 310 | 3-Me | 3-Cl |
| 311 | 4-Me | 3-Cl |
| 312 | 2,3-F$_2$ | 3-Cl |
| 313 | 2,4-F$_2$ | 3-Cl |
| 314 | 2,5-F$_2$ | 3-Cl |
| 315 | 2,6-F$_2$ | 3-Cl |
| 316 | 3,4-F$_2$ | 3-Cl |
| 317 | 3,5-F$_2$ | 3-Cl |
| 318 | 3,4,5-F$_3$ | 3-Cl |
| 319 | 3-F, 4-Cl | 3-Cl |
| 320 | 3-F, 4-Br | 3-Cl |
| 321 | 3-CN, 4-F | 3-Cl |
| 322 | 3-Br, 4-F | 3-Cl |
| 323 | 3-Cl, 4-F | 3-Cl |
| 324 | 3,4-Cl$_2$ | 3-Cl |
| 325 | H | 4-F |
| 326 | 2-F | 4-F |
| 327 | 3-F | 4-F |
| 328 | 4-F | 4-F |
| 329 | 3-Cl | 4-F |
| 330 | 4-Cl | 4-F |
| 331 | 3-Br | 4-F |
| 332 | 4-Br | 4-F |
| 333 | 3-I | 4-F |
| 334 | 3-CN | 4-F |
| 335 | 4-CN | 4-F |
| 336 | 3-NO$_2$ | 4-F |
| 337 | 3-Me | 4-F |
| 338 | 4-Me | 4-F |
| 339 | 2,3-F$_2$ | 4-F |
| 340 | 2,4-F$_2$ | 4-F |
| 341 | 2,5-F$_2$ | 4-F |
| 342 | 2,6-F$_2$ | 4-F |
| 343 | 3,4-F$_2$ | 4-F |
| 344 | 3,5-F$_2$ | 4-F |
| 345 | 3,4,5-F$_3$ | 4-F |
| 346 | 3-F, 4-Cl | 4-F |
| 347 | 3-F, 4-Br | 4-F |
| 348 | 3-CN, 4-F | 4-F |
| 349 | 3-Br, 4-F | 4-F |
| 350 | 3-Cl, 4-F | 4-F |
| 351 | 3,4-Cl$_2$ | 4-F |
| 352 | H | 4-Cl |
| 353 | 2-F | 4-Cl |
| 354 | 3-F | 4-Cl |
| 355 | 4-F | 4-Cl |
| 356 | 3-Cl | 4-Cl |
| 357 | 4-Cl | 4-Cl |
| 358 | 3-Br | 4-Cl |
| 359 | 4-Br | 4-Cl |
| 360 | 3-I | 4-Cl |
| 361 | 3-CN | 4-Cl |
| 362 | 4-CN | 4-Cl |
| 363 | 3-NO$_2$ | 4-Cl |
| 364 | 3-Me | 4-Cl |
| 365 | 4-Me | 4-Cl |
| 366 | 2,3-F$_2$ | 4-Cl |
| 367 | 2,4-F$_2$ | 4-Cl |
| 368 | 2,5-F$_2$ | 4-Cl |
| 369 | 2,6-F$_2$ | 4-Cl |
| 370 | 3,4-F$_2$ | 4-Cl |
| 371 | 3,5-F$_2$ | 4-Cl |
| 372 | 3,4,5-F$_3$ | 4-Cl |
| 373 | 3-F, 4-Cl | 4-Cl |
| 374 | 3-F, 4-Br | 4-Cl |
| 375 | 3-CN, 4-F | 4-Cl |
| 376 | 3-Br, 4-F | 4-Cl |
| 377 | 3-Cl, 4-F | 4-Cl |
| 378 | 3,4-Cl$_2$ | 4-Cl |
| 379 | H | 2-NO$_2$ |

TABLE 1-continued

Preferred meanings of the radicals $(R^2)_n$ and $(R^3)_m$ in the formulae (I), (Ib) and (Ia):

| No. | $(R^2)_n$ | $(R^3)_m$ |
|---|---|---|
| 380 | 2-F | 2-NO$_2$ |
| 381 | 3-F | 2-NO$_2$ |
| 382 | 4-F | 2-NO$_2$ |
| 383 | 3-Cl | 2-NO$_2$ |
| 384 | 4-Cl | 2-NO$_2$ |
| 385 | 3-Br | 2-NO$_2$ |
| 386 | 4-Br | 2-NO$_2$ |
| 387 | 3-I | 2-NO$_2$ |
| 388 | 3-CN | 2-NO$_2$ |
| 389 | 4-CN | 2-NO$_2$ |
| 390 | 3-NO$_2$ | 2-NO$_2$ |
| 391 | 3-Me | 2-NO$_2$ |
| 392 | 4-Me | 2-NO$_2$ |
| 393 | 2,3-F$_2$ | 2-NO$_2$ |
| 394 | 2,4-F$_2$ | 2-NO$_2$ |
| 395 | 2,5-F$_2$ | 2-NO$_2$ |
| 396 | 2,6-F$_2$ | 2-NO$_2$ |
| 397 | 3,4-F$_2$ | 2-NO$_2$ |
| 398 | 3,5-F$_2$ | 2-NO$_2$ |
| 399 | 3,4,5-F$_3$ | 2-NO$_2$ |
| 400 | 3-F, 4-Cl | 2-NO$_2$ |
| 401 | 3-F, 4-Br | 2-NO$_2$ |
| 402 | 3-CN, 4-F | 2-NO$_2$ |
| 403 | 3-Br, 4-F | 2-NO$_2$ |
| 404 | 3-Cl, 4-F | 2-NO$_2$ |
| 405 | 3,4-Cl$_2$ | 2-NO$_2$ |
| 406 | H | 3-NO$_2$ |
| 407 | 2-F | 3-NO$_2$ |
| 408 | 3-F | 3-NO$_2$ |
| 409 | 4-F | 3-NO$_2$ |
| 410 | 3-Cl | 3-NO$_2$ |
| 411 | 4-Cl | 3-NO$_2$ |
| 412 | 3-Br | 3-NO$_2$ |
| 413 | 4-Br | 3-NO$_2$ |
| 414 | 3-I | 3-NO$_2$ |
| 415 | 3-CN | 3-NO$_2$ |
| 416 | 4-CN | 3-NO$_2$ |
| 417 | 3-NO$_2$ | 3-NO$_2$ |
| 418 | 3-Me | 3-NO$_2$ |
| 419 | 4-Me | 3-NO$_2$ |
| 420 | 2,3-F$_2$ | 3-NO$_2$ |
| 421 | 2,4-F$_2$ | 3-NO$_2$ |
| 422 | 2,5-F$_2$ | 3-NO$_2$ |
| 423 | 2,6-F$_2$ | 3-NO$_2$ |
| 424 | 3,4-F$_2$ | 3-NO$_2$ |
| 425 | 3,5-F$_2$ | 3-NO$_2$ |
| 426 | 3,4,5-F$_3$ | 3-NO$_2$ |
| 427 | 3-F, 4-Cl | 3-NO$_2$ |
| 428 | 3-F, 4-Br | 3-NO$_2$ |
| 429 | 3-CN, 4-F | 3-NO$_2$ |
| 430 | 3-Br, 4-F | 3-NO$_2$ |
| 431 | 3-Cl, 4-F | 3-NO$_2$ |
| 432 | 3,4-Cl$_2$ | 3-NO$_2$ |
| 433 | H | 3-NO$_2$ |
| 434 | 2-F | 3-NO$_2$ |
| 435 | 3-F | 3-NO$_2$ |
| 436 | 4-F | 3-NO$_2$ |
| 437 | 3-Cl | 3-NO$_2$ |
| 438 | 4-Cl | 3-NO$_2$ |
| 439 | 3-Br | 3-NO$_2$ |
| 440 | 4-Br | 3-NO$_2$ |
| 441 | 3-I | 3-NO$_2$ |
| 442 | 3-CN | 3-NO$_2$ |
| 443 | 4-CN | 3-NO$_2$ |
| 444 | 3-NO$_2$ | 3-NO$_2$ |
| 445 | 3-Me | 3-NO$_2$ |
| 446 | 4-Me | 3-NO$_2$ |
| 447 | 2,3-F$_2$ | 3-NO$_2$ |
| 448 | 2,4-F$_2$ | 3-NO$_2$ |
| 449 | 2,5-F$_2$ | 3-NO$_2$ |
| 450 | 2,6-F$_2$ | 3-NO$_2$ |
| 451 | 3,4-F$_2$ | 3-NO$_2$ |
| 452 | 3,5-F$_2$ | 3-NO$_2$ |
| 453 | 3,4,5-F$_3$ | 3-NO$_2$ |
| 454 | 3-F, 4-Cl | 3-NO$_2$ |
| 455 | 3-F, 4-Br | 3-NO$_2$ |
| 456 | 3-CN, 4-F | 3-NO$_2$ |
| 457 | 3-Br, 4-F | 3-NO$_2$ |
| 458 | 3-Cl, 4-F | 3-NO$_2$ |
| 459 | 3,4-Cl$_2$ | 3-NO$_2$ |
| 460 | H | 4-NO$_2$ |
| 461 | 2-F | 4-NO$_2$ |
| 462 | 3-F | 4-NO$_2$ |
| 463 | 4-F | 4-NO$_2$ |
| 464 | 3-Cl | 4-NO$_2$ |
| 465 | 4-Cl | 4-NO$_2$ |
| 466 | 3-Br | 4-NO$_2$ |
| 467 | 4-Br | 4-NO$_2$ |
| 468 | 3-I | 4-NO$_2$ |
| 469 | 3-CN | 4-NO$_2$ |
| 470 | 4-CN | 4-NO$_2$ |
| 471 | 3-NO$_2$ | 4-NO$_2$ |
| 472 | 3-Me | 4-NO$_2$ |
| 473 | 4-Me | 4-NO$_2$ |
| 474 | 2,3-F$_2$ | 4-NO$_2$ |
| 475 | 2,4-F$_2$ | 4-NO$_2$ |
| 476 | 2,5-F$_2$ | 4-NO$_2$ |
| 477 | 2,6-F$_2$ | 4-NO$_2$ |
| 478 | 3,4-F$_2$ | 4-NO$_2$ |
| 479 | 3,5-F$_2$ | 4-NO$_2$ |
| 480 | 3,4,5-F$_3$ | 4-NO$_2$ |
| 481 | 3-F, 4-Cl | 4-NO$_2$ |
| 482 | 3-F, 4-Br | 4-NO$_2$ |
| 483 | 3-CN, 4-F | 4-NO$_2$ |
| 484 | 3-Br, 4-F | 4-NO$_2$ |
| 485 | 3-Cl, 4-F | 4-NO$_2$ |
| 486 | 3,4-Cl$_2$ | 4-NO$_2$ |
| 487 | H | 2,3-Cl$_2$ |
| 488 | 2-F | 2,3-Cl$_2$ |
| 489 | 3-F | 2,3-Cl$_2$ |
| 490 | 4-F | 2,3-Cl$_2$ |
| 491 | 3-Cl | 2,3-Cl$_2$ |
| 492 | 4-Cl | 2,3-Cl$_2$ |
| 493 | 3-Br | 2,3-Cl$_2$ |
| 494 | 4-Br | 2,3-Cl$_2$ |
| 495 | 3-I | 2,3-Cl$_2$ |
| 496 | 3-CN | 2,3-Cl$_2$ |
| 497 | 4-CN | 2,3-Cl$_2$ |
| 498 | 3-NO$_2$ | 2,3-Cl$_2$ |
| 499 | 3-Me | 2,3-Cl$_2$ |
| 500 | 4-Me | 2,3-Cl$_2$ |
| 501 | 2,3-F$_2$ | 2,3-Cl$_2$ |
| 502 | 2,4-F$_2$ | 2,3-Cl$_2$ |
| 503 | 2,5-F$_2$ | 2,3-Cl$_2$ |
| 504 | 2,6-F$_2$ | 2,3-Cl$_2$ |
| 505 | 3,4-F$_2$ | 2,3-Cl$_2$ |
| 506 | 3,5-F$_2$ | 2,3-Cl$_2$ |
| 507 | 3,4,5-F$_3$ | 2,3-Cl$_2$ |
| 508 | 3-F, 4-Cl | 2,3-Cl$_2$ |
| 509 | 3-F, 4-Br | 2,3-Cl$_2$ |
| 510 | 3-CN, 4-F | 2,3-Cl$_2$ |
| 511 | 3-Br, 4-F | 2,3-Cl$_2$ |
| 512 | 3-Cl, 4-F | 2,3-Cl$_2$ |
| 513 | 3,4-Cl$_2$ | 2,3-Cl$_2$ |
| 514 | H | 2,4-F$_2$ |
| 515 | 2-F | 2,4-F$_2$ |
| 516 | 3-F | 2,4-F$_2$ |
| 517 | 4-F | 2,4-F$_2$ |
| 518 | 3-Cl | 2,4-F$_2$ |
| 519 | 4-Cl | 2,4-F$_2$ |
| 520 | 3-Br | 2,4-F$_2$ |
| 521 | 4-Br | 2,4-F$_2$ |
| 522 | 3-I | 2,4-F$_2$ |
| 523 | 3-CN | 2,4-F$_2$ |
| 524 | 4-CN | 2,4-F$_2$ |
| 525 | 3-NO$_2$ | 2,4-F$_2$ |
| 526 | 3-Me | 2,4-F$_2$ |
| 527 | 4-Me | 2,4-F$_2$ |
| 528 | 2,3-F$_2$ | 2,4-F$_2$ |
| 529 | 2,4-F$_2$ | 2,4-F$_2$ |

TABLE 1-continued

Preferred meanings of the radicals $(R^2)_n$ and $(R^3)_m$ in the formulae (I), (Ib) and (Ia):

| No. | $(R^2)_n$ | $(R^3)_m$ |
|---|---|---|
| 530 | 2,5-F$_2$ | 2,4-F$_2$ |
| 531 | 2,6-F$_2$ | 2,4-F$_2$ |
| 532 | 3,4-F$_2$ | 2,4-F$_2$ |
| 533 | 3,5-F$_2$ | 2,4-F$_2$ |
| 534 | 3,4,5-F$_3$ | 2,4-F$_2$ |
| 535 | 3-F, 4-Cl | 2,4-F$_2$ |
| 536 | 3-F, 4-Br | 2,4-F$_2$ |
| 537 | 3-CN, 4-F | 2,4-F$_2$ |
| 538 | 3-Br, 4-F | 2,4-F$_2$ |
| 539 | 3-Cl, 4-F | 2,4-F$_2$ |
| 540 | 3,4-Cl$_2$ | 2,4-F$_2$ |
| 541 | H | 2,5-Cl$_2$ |
| 542 | 2-F | 2,5-Cl$_2$ |
| 543 | 3-F | 2,5-Cl$_2$ |
| 544 | 4-F | 2,5-Cl$_2$ |
| 545 | 3-Cl | 2,5-Cl$_2$ |
| 546 | 4-Cl | 2,5-Cl$_2$ |
| 547 | 3-Br | 2,5-Cl$_2$ |
| 548 | 4-Br | 2,5-Cl$_2$ |
| 549 | 3-I | 2,5-Cl$_2$ |
| 550 | 3-CN | 2,5-Cl$_2$ |
| 551 | 4-CN | 2,5-Cl$_2$ |
| 552 | 3-NO$_2$ | 2,5-Cl$_2$ |
| 553 | 3-Me | 2,5-Cl$_2$ |
| 554 | 4-Me | 2,5-Cl$_2$ |
| 555 | 2,3-F$_2$ | 2,5-Cl$_2$ |
| 556 | 2,4-F$_2$ | 2,5-Cl$_2$ |
| 557 | 2,5-F$_2$ | 2,5-Cl$_2$ |
| 558 | 2,6-F$_2$ | 2,5-Cl$_2$ |
| 559 | 3,4-F$_2$ | 2,5-Cl$_2$ |
| 560 | 3,5-F$_2$ | 2,5-Cl$_2$ |
| 561 | 3,4,5-F$_3$ | 2,5-Cl$_2$ |
| 562 | 3-F, 4-Cl | 2,5-Cl$_2$ |
| 563 | 3-F, 4-Br | 2,5-Cl$_2$ |
| 564 | 3-CN, 4-F | 2,5-Cl$_2$ |
| 565 | 3-Br, 4-F | 2,5-Cl$_2$ |
| 566 | 3-Cl, 4-F | 2,5-Cl$_2$ |
| 567 | 3,4-Cl$_2$ | 2,5-Cl$_2$ |
| 568 | H | 2,6-Cl$_2$ |
| 569 | 2-F | 2,6-Cl$_2$ |
| 570 | 3-F | 2,6-Cl$_2$ |
| 571 | 4-F | 2,6-Cl$_2$ |
| 572 | 3-Cl | 2,6-Cl$_2$ |
| 573 | 4-Cl | 2,6-Cl$_2$ |
| 574 | 3-Br | 2,6-Cl$_2$ |
| 575 | 4-Br | 2,6-Cl$_2$ |
| 576 | 3-I | 2,6-Cl$_2$ |
| 577 | 3-CN | 2,6-Cl$_2$ |
| 578 | 4-CN | 2,6-Cl$_2$ |
| 579 | 3-NO$_2$ | 2,6-Cl$_2$ |
| 580 | 3-Me | 2,6-Cl$_2$ |
| 581 | 4-Me | 2,6-Cl$_2$ |
| 582 | 2,3-F$_2$ | 2,6-Cl$_2$ |
| 583 | 2,4-F$_2$ | 2,6-Cl$_2$ |
| 584 | 2,5-F$_2$ | 2,6-Cl$_2$ |
| 585 | 2,6-F$_2$ | 2,6-Cl$_2$ |
| 586 | 3,4-F$_2$ | 2,6-Cl$_2$ |
| 587 | 3,5-F$_2$ | 2,6-Cl$_2$ |
| 588 | 3,4,5-F$_3$ | 2,6-Cl$_2$ |
| 589 | 3-F, 4-Cl | 2,6-Cl$_2$ |
| 590 | 3-F, 4-Br | 2,6-Cl$_2$ |
| 591 | 3-CN, 4-F | 2,6-Cl$_2$ |
| 592 | 3-Br, 4-F | 2,6-Cl$_2$ |
| 593 | 3-Cl, 4-F | 2,6-Cl$_2$ |
| 594 | 3,4-Cl$_2$ | 2,6-Cl$_2$ |
| 595 | H | 3,4-Cl$_2$ |
| 596 | 2-F | 3,4-Cl$_2$ |
| 597 | 3-F | 3,4-Cl$_2$ |
| 598 | 4-F | 3,4-Cl$_2$ |
| 599 | 3-Cl | 3,4-Cl$_2$ |
| 600 | 4-Cl | 3,4-Cl$_2$ |
| 601 | 3-Br | 3,4-Cl$_2$ |
| 602 | 4-Br | 3,4-Cl$_2$ |
| 603 | 3-I | 3,4-Cl$_2$ |
| 604 | 3-CN | 3,4-Cl$_2$ |
| 605 | 4-CN | 3,4-Cl$_2$ |
| 606 | 3-NO$_2$ | 3,4-Cl$_2$ |
| 607 | 3-Me | 3,4-Cl$_2$ |
| 608 | 4-Me | 3,4-Cl$_2$ |
| 609 | 2,3-F$_2$ | 3,4-Cl$_2$ |
| 610 | 2,4-F$_2$ | 3,4-Cl$_2$ |
| 611 | 2,5-F$_2$ | 3,4-Cl$_2$ |
| 612 | 2,6-F$_2$ | 3,4-Cl$_2$ |
| 613 | 3,4-F$_2$ | 3,4-Cl$_2$ |
| 614 | 3,5-F$_2$ | 3,4-Cl$_2$ |
| 615 | 3,4,5-F$_3$ | 3,4-Cl$_2$ |
| 616 | 3-F, 4-Cl | 3,4-Cl$_2$ |
| 617 | 3-F, 4-Br | 3,4-Cl$_2$ |
| 618 | 3-CN, 4-F | 3,4-Cl$_2$ |
| 619 | 3-Br, 4-F | 3,4-Cl$_2$ |
| 620 | 3-Cl, 4-F | 3,4-Cl$_2$ |
| 621 | 3,4-Cl$_2$ | 3,4-Cl$_2$ |
| 622 | H | 3,5-Cl$_2$ |
| 623 | 2-F | 3,5-Cl$_2$ |
| 624 | 3-F | 3,5-Cl$_2$ |
| 625 | 4-F | 3,5-Cl$_2$ |
| 626 | 3-Cl | 3,5-Cl$_2$ |
| 627 | 4-Cl | 3,5-Cl$_2$ |
| 628 | 3-Br | 3,5-Cl$_2$ |
| 629 | 4-Br | 3,5-Cl$_2$ |
| 630 | 3-I | 3,5-Cl$_2$ |
| 631 | 3-CN | 3,5-Cl$_2$ |
| 632 | 4-CN | 3,5-Cl$_2$ |
| 633 | 3-NO$_2$ | 3,5-Cl$_2$ |
| 634 | 3-Me | 3,5-Cl$_2$ |
| 635 | 4-Me | 3,5-Cl$_2$ |
| 636 | 2,3-F$_2$ | 3,5-Cl$_2$ |
| 637 | 2,4-F$_2$ | 3,5-Cl$_2$ |
| 638 | 2,5-F$_2$ | 3,5-Cl$_2$ |
| 639 | 2,6-F$_2$ | 3,5-Cl$_2$ |
| 640 | 3,4-F$_2$ | 3,5-Cl$_2$ |
| 641 | 3,5-F$_2$ | 3,5-Cl$_2$ |
| 642 | 3,4,5-F$_3$ | 3,5-Cl$_2$ |
| 643 | 3-F, 4-Cl | 3,5-Cl$_2$ |
| 644 | 3-F, 4-Br | 3,5-Cl$_2$ |
| 645 | 3-CN, 4-F | 3,5-Cl$_2$ |
| 646 | 3-Br, 4-F | 3,5-Cl$_2$ |
| 647 | 3-Cl, 4-F | 3,5-Cl$_2$ |
| 648 | 3,4-Cl$_2$ | 3,5-Cl$_2$ |
| 649 | H | 2-F, 3-Cl |
| 650 | 2-F | 2-F, 3-Cl |
| 651 | 3-F | 2-F, 3-Cl |
| 652 | 4-F | 2-F, 3-Cl |
| 653 | 3-Cl | 2-F, 3-Cl |
| 654 | 4-Cl | 2-F, 3-Cl |
| 655 | 3-Br | 2-F, 3-Cl |
| 656 | 4-Br | 2-F, 3-Cl |
| 657 | 3-I | 2-F, 3-Cl |
| 658 | 3-CN | 2-F, 3-Cl |
| 659 | 4-CN | 2-F, 3-Cl |
| 660 | 3-NO$_2$ | 2-F, 3-Cl |
| 661 | 3-Me | 2-F, 3-Cl |
| 662 | 4-Me | 2-F, 3-Cl |
| 663 | 2,3-F$_2$ | 2-F, 3-Cl |
| 664 | 2,4-F$_2$ | 2-F, 3-Cl |
| 665 | 2,5-F$_2$ | 2-F, 3-Cl |
| 666 | 2,6-F$_2$ | 2-F, 3-Cl |
| 667 | 3,4-F$_2$ | 2-F, 3-Cl |
| 668 | 3,5-F$_2$ | 2-F, 3-Cl |
| 669 | 3,4,5-F$_3$ | 2-F, 3-Cl |
| 670 | 3-F, 4-Cl | 2-F, 3-Cl |
| 671 | 3-F, 4-Br | 2-F, 3-Cl |
| 672 | 3-CN, 4-F | 2-F, 3-Cl |
| 673 | 3-Br, 4-F | 2-F, 3-Cl |
| 674 | 3-Cl, 4-F | 2-F, 3-Cl |
| 675 | 3,4-Cl$_2$ | 2-F, 3-Cl |
| 676 | H | 2-F, 4-Cl |
| 677 | 2-F | 2-F, 4-Cl |
| 678 | 3-F | 2-F, 4-Cl |
| 679 | 4-F | 2-F, 4-Cl |

TABLE 1-continued

Preferred meanings of the radicals $(R^2)_n$ and $(R^3)_m$ in the formulae (I), (Ib) and (Ia):

| No. | $(R^2)_n$ | $(R^3)_m$ |
|---|---|---|
| 680 | 3-Cl | 2-F, 4-Cl |
| 681 | 4-Cl | 2-F, 4-Cl |
| 682 | 3-Br | 2-F, 4-Cl |
| 683 | 4-Br | 2-F, 4-Cl |
| 684 | 3-I | 2-F, 4-Cl |
| 685 | 3-CN | 2-F, 4-Cl |
| 686 | 4-CN | 2-F, 4-Cl |
| 687 | 3-NO$_2$ | 2-F, 4-Cl |
| 688 | 3-Me | 2-F, 4-Cl |
| 689 | 4-Me | 2-F, 4-Cl |
| 690 | 2,3-F$_2$ | 2-F, 4-Cl |
| 691 | 2,4-F$_2$ | 2-F, 4-Cl |
| 692 | 2,5-F$_2$ | 2-F, 4-Cl |
| 693 | 2,6-F$_2$ | 2-F, 4-Cl |
| 694 | 3,4-F$_2$ | 2-F, 4-Cl |
| 695 | 3,5-F$_2$ | 2-F, 4-Cl |
| 696 | 3,4,5-F$_3$ | 2-F, 4-Cl |
| 697 | 3-F, 4-Cl | 2-F, 4-Cl |
| 698 | 3-F, 4-Br | 2-F, 4-Cl |
| 699 | 3-CN, 4-F | 2-F, 4-Cl |
| 700 | 3-Br, 4-F | 2-F, 4-Cl |
| 701 | 3-Cl, 4-F | 2-F, 4-Cl |
| 702 | 3,4-Cl$_2$ | 2-F, 4-Cl |
| 703 | H | 2-F, 5-Cl |
| 704 | 2-F | 2-F, 5-Cl |
| 705 | 3-F | 2-F, 5-Cl |
| 706 | 4-F | 2-F, 5-Cl |
| 707 | 3-Cl | 2-F, 5-Cl |
| 708 | 4-Cl | 2-F, 5-Cl |
| 709 | 3-Br | 2-F, 5-Cl |
| 710 | 4-Br | 2-F, 5-Cl |
| 711 | 3-I | 2-F, 5-Cl |
| 712 | 3-CN | 2-F, 5-Cl |
| 713 | 4-CN | 2-F, 5-Cl |
| 714 | 3-NO$_2$ | 2-F, 5-Cl |
| 715 | 3-Me | 2-F, 5-Cl |
| 716 | 4-Me | 2-F, 5-Cl |
| 717 | 2,3-F$_2$ | 2-F, 5-Cl |
| 718 | 2,4-F$_2$ | 2-F, 5-Cl |
| 719 | 2,5-F$_2$ | 2-F, 5-Cl |
| 720 | 2,6-F$_2$ | 2-F, 5-Cl |
| 721 | 3,4-F$_2$ | 2-F, 5-Cl |
| 722 | 3,5-F$_2$ | 2-F, 5-Cl |
| 723 | 3,4,5-F$_3$ | 2-F, 5-Cl |
| 724 | 3-F, 4-Cl | 2-F, 5-Cl |
| 725 | 3-F, 4-Br | 2-F, 5-Cl |
| 726 | 3-CN, 4-F | 2-F, 5-Cl |
| 727 | 3-Br, 4-F | 2-F, 5-Cl |
| 728 | 3-Cl, 4-F | 2-F, 5-Cl |
| 729 | 3,4-Cl$_2$ | 2-F, 5-Cl |
| 730 | H | 2-Cl, 6-F |
| 731 | 2-F | 2-Cl, 6-F |
| 732 | 3-F | 2-Cl, 6-F |
| 733 | 4-F | 2-Cl, 6-F |
| 734 | 3-Cl | 2-Cl, 6-F |
| 735 | 4-Cl | 2-Cl, 6-F |
| 736 | 3-Br | 2-Cl, 6-F |
| 737 | 4-Br | 2-Cl, 6-F |
| 738 | 3-I | 2-Cl, 6-F |
| 739 | 3-CN | 2-Cl, 6-F |
| 740 | 4-CN | 2-Cl, 6-F |
| 741 | 3-NO$_2$ | 2-Cl, 6-F |
| 742 | 3-Me | 2-Cl, 6-F |
| 743 | 4-Me | 2-Cl, 6-F |
| 744 | 2,3-F$_2$ | 2-Cl, 6-F |
| 745 | 2,4-F$_2$ | 2-Cl, 6-F |
| 746 | 2,5-F$_2$ | 2-Cl, 6-F |
| 747 | 2,6-F$_2$ | 2-Cl, 6-F |
| 748 | 3,4-F$_2$ | 2-Cl, 6-F |
| 749 | 3,5-F$_2$ | 2-Cl, 6-F |
| 750 | 3,4,5-F$_3$ | 2-Cl, 6-F |
| 751 | 3-F, 4-Cl | 2-Cl, 6-F |
| 752 | 3-F, 4-Br | 2-Cl, 6-F |
| 753 | 3-CN, 4-F | 2-Cl, 6-F |
| 754 | 3-Br, 4-F | 2-Cl, 6-F |
| 755 | 3-Cl, 4-F | 2-Cl, 6-F |
| 756 | 3,4-Cl$_2$ | 2-Cl, 6-F |
| 757 | H | 3-F, 4-Cl |
| 758 | 2-F | 3-F, 4-Cl |
| 759 | 3-F | 3-F, 4-Cl |
| 760 | 4-F | 3-F, 4-Cl |
| 761 | 3-Cl | 3-F, 4-Cl |
| 762 | 4-Cl | 3-F, 4-Cl |
| 763 | 3-Br | 3-F, 4-Cl |
| 764 | 4-Br | 3-F, 4-Cl |
| 765 | 3-I | 3-F, 4-Cl |
| 766 | 3-CN | 3-F, 4-Cl |
| 767 | 4-CN | 3-F, 4-Cl |
| 768 | 3-NO$_2$ | 3-F, 4-Cl |
| 769 | 3-Me | 3-F, 4-Cl |
| 770 | 4-Me | 3-F, 4-Cl |
| 771 | 2,3-F$_2$ | 3-F, 4-Cl |
| 772 | 2,4-F$_2$ | 3-F, 4-Cl |
| 773 | 2,5-F$_2$ | 3-F, 4-Cl |
| 774 | 2,6-F$_2$ | 3-F, 4-Cl |
| 775 | 3,4-F$_2$ | 3-F, 4-Cl |
| 776 | 3,5-F$_2$ | 3-F, 4-Cl |
| 777 | 3,4,5-F$_3$ | 3-F, 4-Cl |
| 778 | 3-F, 4-Cl | 3-F, 4-Cl |
| 779 | 3-F, 4-Br | 3-F, 4-Cl |
| 780 | 3-CN, 4-F | 3-F, 4-Cl |
| 781 | 3-Br, 4-F | 3-F, 4-Cl |
| 782 | 3-Cl, 4-F | 3-F, 4-Cl |
| 783 | 3,4-Cl$_2$ | 3-F, 4-Cl |
| 784 | H | 3-Cl, 5-F |
| 785 | 2-F | 3-Cl, 5-F |
| 786 | 3-F | 3-Cl, 5-F |
| 787 | 4-F | 3-Cl, 5-F |
| 788 | 3-Cl | 3-Cl, 5-F |
| 789 | 4-Cl | 3-Cl, 5-F |
| 790 | 3-Br | 3-Cl, 5-F |
| 791 | 4-Br | 3-Cl, 5-F |
| 792 | 3-I | 3-Cl, 5-F |
| 793 | 3-CN | 3-Cl, 5-F |
| 794 | 4-CN | 3-Cl, 5-F |
| 795 | 3-NO$_2$ | 3-Cl, 5-F |
| 796 | 3-Me | 3-Cl, 5-F |
| 797 | 4-Me | 3-Cl, 5-F |
| 798 | 2,3-F$_2$ | 3-Cl, 5-F |
| 799 | 2,4-F$_2$ | 3-Cl, 5-F |
| 800 | 2,5-F$_2$ | 3-Cl, 5-F |
| 801 | 2,6-F$_2$ | 3-Cl, 5-F |
| 802 | 3,4-F$_2$ | 3-Cl, 5-F |
| 803 | 3,5-F$_2$ | 3-Cl, 5-F |
| 804 | 3,4,5-F$_3$ | 3-Cl, 5-F |
| 805 | 3-F, 4-Cl | 3-Cl, 5-F |
| 806 | 3-F, 4-Br | 3-Cl, 5-F |
| 807 | 3-CN, 4-F | 3-Cl, 5-F |
| 808 | 3-Br, 4-F | 3-Cl, 5-F |
| 809 | 3-Cl, 4-F | 3-Cl, 5-F |
| 810 | 3,4-Cl$_2$ | 3-Cl, 5-F |
| 811 | H | 2-Cl, 5-F |
| 812 | 2-F | 2-Cl, 5-F |
| 813 | 3-F | 2-Cl, 5-F |
| 814 | 4-F | 2-Cl, 5-F |
| 815 | 3-Cl | 2-Cl, 5-F |
| 816 | 4-Cl | 2-Cl, 5-F |
| 817 | 3-Br | 2-Cl, 5-F |
| 818 | 4-Br | 2-Cl, 5-F |
| 819 | 3-I | 2-Cl, 5-F |
| 820 | 3-CN | 2-Cl, 5-F |
| 821 | 4-CN | 2-Cl, 5-F |
| 822 | 3-NO$_2$ | 2-Cl, 5-F |
| 823 | 3-Me | 2-Cl, 5-F |
| 824 | 4-Me | 2-Cl, 5-F |
| 825 | 2,3-F$_2$ | 2-Cl, 5-F |
| 826 | 2,4-F$_2$ | 2-Cl, 5-F |
| 827 | 2,5-F$_2$ | 2-Cl, 5-F |
| 828 | 2,6-F$_2$ | 2-Cl, 5-F |
| 829 | 3,4-F$_2$ | 2-Cl, 5-F |

TABLE 1-continued

Preferred meanings of the radicals $(R^2)_n$ and $(R^3)_m$ in the formulae (I), (Ib) and (Ia):

| No. | $(R^2)_n$ | $(R^3)_m$ |
|---|---|---|
| 830 | 3,5-F$_2$ | 2-Cl, 5-F |
| 831 | 3,4,5-F$_3$ | 2-Cl, 5-F |
| 832 | 3-F, 4-Cl | 2-Cl, 5-F |
| 833 | 3-F, 4-Br | 2-Cl, 5-F |
| 834 | 3-CN, 4-F | 2-Cl, 5-F |
| 835 | 3-Br, 4-F | 2-Cl, 5-F |
| 836 | 3-Cl, 4-F | 2-Cl, 5-F |
| 837 | 3,4-Cl$_2$ | 2-Cl, 5-F |
| 838 | H | 2-Cl, 4-F |
| 839 | 2-F | 2-Cl, 4-F |
| 840 | 3-F | 2-Cl, 4-F |
| 841 | 4-F | 2-Cl, 4-F |
| 842 | 3-Cl | 2-Cl, 4-F |
| 843 | 4-Cl | 2-Cl, 4-F |
| 844 | 3-Br | 2-Cl, 4-F |
| 845 | 4-Br | 2-Cl, 4-F |
| 846 | 3-I | 2-Cl, 4-F |
| 847 | 3-CN | 2-Cl, 4-F |
| 848 | 4-CN | 2-Cl, 4-F |
| 849 | 3-NO$_2$ | 2-Cl, 4-F |
| 850 | 3-Me | 2-Cl, 4-F |
| 851 | 4-Me | 2-Cl, 4-F |
| 852 | 2,3-F$_2$ | 2-Cl, 4-F |
| 853 | 2,4-F$_2$ | 2-Cl, 4-F |
| 854 | 2,5-F$_2$ | 2-Cl, 4-F |
| 855 | 2,6-F$_2$ | 2-Cl, 4-F |
| 856 | 3,4-F$_2$ | 2-Cl, 4-F |
| 857 | 3,5-F$_2$ | 2-Cl, 4-F |
| 858 | 3,4,5-F$_3$ | 2-Cl, 4-F |
| 859 | 3-F, 4-Cl | 2-Cl, 4-F |
| 860 | 3-F, 4-Br | 2-Cl, 4-F |
| 861 | 3-CN, 4-F | 2-Cl, 4-F |
| 862 | 3-Br, 4-F | 2-Cl, 4-F |
| 863 | 3-Cl, 4-F | 2-Cl, 4-F |
| 864 | 3,4-Cl$_2$ | 2-Cl, 4-F |
| 865 | H | 3-Cl, 4-F |
| 866 | 2-F | 3-Cl, 4-F |
| 867 | 3-F | 3-Cl, 4-F |
| 868 | 4-F | 3-Cl, 4-F |
| 869 | 3-Cl | 3-Cl, 4-F |
| 870 | 4-Cl | 3-Cl, 4-F |
| 871 | 3-Br | 3-Cl, 4-F |
| 872 | 4-Br | 3-Cl, 4-F |
| 873 | 3-I | 3-Cl, 4-F |
| 874 | 3-CN | 3-Cl, 4-F |
| 875 | 4-CN | 3-Cl, 4-F |
| 876 | 3-NO$_2$ | 3-Cl, 4-F |
| 877 | 3-Me | 3-Cl, 4-F |
| 878 | 4-Me | 3-Cl, 4-F |
| 879 | 2,3-F$_2$ | 3-Cl, 4-F |
| 880 | 2,4-F$_2$ | 3-Cl, 4-F |
| 881 | 2,5-F$_2$ | 3-Cl, 4-F |
| 882 | 2,6-F$_2$ | 3-Cl, 4-F |
| 883 | 3,4-F$_2$ | 3-Cl, 4-F |
| 884 | 3,5-F$_2$ | 3-Cl, 4-F |
| 885 | 3,4,5-F$_3$ | 3-Cl, 4-F |
| 886 | 3-F, 4-Cl | 3-Cl, 4-F |
| 887 | 3-F, 4-Br | 3-Cl, 4-F |
| 888 | 3-CN, 4-F | 3-Cl, 4-F |
| 889 | 3-Br, 4-F | 3-Cl, 4-F |
| 890 | 3-Cl, 4-F | 3-Cl, 4-F |
| 891 | 3,4-Cl$_2$ | 3-Cl, 4-F |
| 892 | H | 2-Cl, 3-F |
| 893 | 2-F | 2-Cl, 3-F |
| 894 | 3-F | 2-Cl, 3-F |
| 895 | 4-F | 2-Cl, 3-F |
| 896 | 3-Cl | 2-Cl, 3-F |
| 897 | 4-Cl | 2-Cl, 3-F |
| 898 | 3-Br | 2-Cl, 3-F |
| 899 | 4-Br | 2-Cl, 3-F |
| 900 | 3-I | 2-Cl, 3-F |
| 901 | 3-CN | 2-Cl, 3-F |
| 902 | 4-CN | 2-Cl, 3-F |
| 903 | 3-NO$_2$ | 2-Cl, 3-F |
| 904 | 3-Me | 2-Cl, 3-F |
| 905 | 4-Me | 2-Cl, 3-F |
| 906 | 2,3-F$_2$ | 2-Cl, 3-F |
| 907 | 2,4-F$_2$ | 2-Cl, 3-F |
| 908 | 2,5-F$_2$ | 2-Cl, 3-F |
| 909 | 2,6-F$_2$ | 2-Cl, 3-F |
| 910 | 3,4-F$_2$ | 2-Cl, 3-F |
| 911 | 3,5-F$_2$ | 2-Cl, 3-F |
| 912 | 3,4,5-F$_3$ | 2-Cl, 3-F |
| 913 | 3-F, 4-Cl | 2-Cl, 3-F |
| 914 | 3-F, 4-Br | 2-Cl, 3-F |
| 915 | 3-CN, 4-F | 2-Cl, 3-F |
| 916 | 3-Br, 4-F | 2-Cl, 3-F |
| 917 | 3-Cl, 4-F | 2-Cl, 3-F |
| 918 | 3,4-Cl$_2$ | 2-Cl, 3-F |
| 919 | H | H |
| 920 | 2-F | H |
| 921 | 3-F | H |
| 922 | 4-F | H |
| 923 | 3-Cl | H |
| 924 | 4-Cl | H |
| 925 | 3-Br | H |
| 926 | 4-Br | H |
| 927 | 3-I | H |
| 928 | 3-CN | H |
| 929 | 4-CN | H |
| 930 | 3-NO$_2$ | H |
| 931 | 3-Me | H |
| 932 | 4-Me | H |
| 933 | 2,3-F$_2$ | H |
| 934 | 2,4-F$_2$ | H |
| 935 | 2,5-F$_2$ | H |
| 936 | 2,6-F$_2$ | H |
| 937 | 3,4-F$_2$ | H |
| 938 | 3,5-F$_2$ | H |
| 939 | 3,4,5-F$_3$ | H |
| 940 | 3-F, 4-Cl | H |
| 941 | 3-F, 4-Br | H |
| 942 | 3-CN, 4-F | H |
| 943 | 3-Br, 4-F | H |
| 944 | 3-Cl, 4-F | H |
| 945 | 3,4-Cl$_2$ | H |
| 946 | H | 2-CN |
| 947 | 2-F | 2-CN |
| 948 | 3-F | 2-CN |
| 949 | 4-F | 2-CN |
| 950 | 3-Cl | 2-CN |
| 951 | 4-Cl | 2-CN |
| 952 | 3-Br | 2-CN |
| 953 | 4-Br | 2-CN |
| 954 | 3-I | 2-CN |
| 955 | 3-CN | 2-CN |
| 956 | 4-CN | 2-CN |
| 957 | 3-NO$_2$ | 2-CN |
| 958 | 3-Me | 2-CN |
| 959 | 4-Me | 2-CN |
| 960 | 2,3-F$_2$ | 2-CN |
| 961 | 2,4-F$_2$ | 2-CN |
| 962 | 2,5-F$_2$ | 2-CN |
| 963 | 2,6-F$_2$ | 2-CN |
| 964 | 3,4-F$_2$ | 2-CN |
| 965 | 3,5-F$_2$ | 2-CN |
| 966 | 3,4,5-F$_3$ | 2-CN |
| 967 | 3-F, 4-Cl | 2-CN |
| 968 | 3-F, 4-Br | 2-CN |
| 969 | 3-CN, 4-F | 2-CN |
| 970 | 3-Br, 4-F | 2-CN |
| 971 | 3-Cl, 4-F | 2-CN |
| 972 | 3,4-Cl$_2$ | 2-CN |
| 973 | H | 3-CN |
| 974 | 2-F | 3-CN |
| 975 | 3-F | 3-CN |
| 976 | 4-F | 3-CN |
| 977 | 3-Cl | 3-CN |
| 978 | 4-Cl | 3-CN |
| 979 | 3-Br | 3-CN |

TABLE 1-continued

Preferred meanings of the radicals $(R^2)_n$ and $(R^3)_m$ in the formulae (I), (Ib) and (Ia):

| No. | $(R^2)_n$ | $(R^3)_m$ |
|---|---|---|
| 980 | 4-Br | 3-CN |
| 981 | 3-I | 3-CN |
| 982 | 3-CN | 3-CN |
| 983 | 4-CN | 3-CN |
| 984 | 3-NO$_2$ | 3-CN |
| 985 | 3-Me | 3-CN |
| 986 | 4-Me | 3-CN |
| 987 | 2,3-F$_2$ | 3-CN |
| 988 | 2,4-F$_2$ | 3-CN |
| 989 | 2,5-F$_2$ | 3-CN |
| 990 | 2,6-F$_2$ | 3-CN |
| 991 | 3,4-F$_2$ | 3-CN |
| 992 | 3,5-F$_2$ | 3-CN |
| 993 | 3,4,5-F$_3$ | 3-CN |
| 994 | 3-F, 4-Cl | 3-CN |
| 995 | 3-F, 4-Br | 3-CN |
| 996 | 3-CN, 4-F | 3-CN |
| 997 | 3-Br, 4-F | 3-CN |
| 998 | 3-Cl, 4-F | 3-CN |
| 999 | 3,4-Cl$_2$ | 3-CN |
| 1000 | H | 4-CN |
| 1001 | 2-F | 4-CN |
| 1002 | 3-F | 4-CN |
| 1003 | 4-F | 4-CN |
| 1004 | 3-Cl | 4-CN |
| 1005 | 4-Cl | 4-CN |
| 1006 | 3-Br | 4-CN |
| 1007 | 4-Br | 4-CN |
| 1008 | 3-I | 4-CN |
| 1009 | 3-CN | 4-CN |
| 1010 | 4-CN | 4-CN |
| 1011 | 3-NO$_2$ | 4-CN |
| 1012 | 3-Me | 4-CN |
| 1013 | 4-Me | 4-CN |
| 1014 | 2,3-F$_2$ | 4-CN |
| 1015 | 2,4-F$_2$ | 4-CN |
| 1016 | 2,5-F$_2$ | 4-CN |
| 1017 | 2,6-F$_2$ | 4-CN |
| 1018 | 3,4-F$_2$ | 4-CN |
| 1019 | 3,5-F$_2$ | 4-CN |
| 1020 | 3,4,5-F$_3$ | 4-CN |
| 1021 | 3-F, 4-Cl | 4-CN |
| 1022 | 3-F, 4-Br | 4-CN |
| 1023 | 3-CN, 4-F | 4-CN |
| 1024 | 3-Br, 4-F | 4-CN |
| 1025 | 3-Cl, 4-F | 4-CN |
| 1026 | 3,4-Cl$_2$ | 4-CN |
| 1027 | H | 4-Br |
| 1028 | 2-F | 4-Br |
| 1029 | 3-F | 4-Br |
| 1030 | 4-F | 4-Br |
| 1031 | 3-Cl | 4-Br |
| 1032 | 4-Cl | 4-Br |
| 1033 | 3-Br | 4-Br |
| 1034 | 4-Br | 4-Br |
| 1035 | 3-I | 4-Br |
| 1036 | 3-CN | 4-Br |
| 1037 | 4-CN | 4-Br |
| 1038 | 3-NO$_2$ | 4-Br |
| 1039 | 3-Me | 4-Br |
| 1040 | 4-Me | 4-Br |
| 1041 | 2,3-F$_2$ | 4-Br |
| 1042 | 2,4-F$_2$ | 4-Br |
| 1043 | 2,5-F$_2$ | 4-Br |
| 1044 | 2,6-F$_2$ | 4-Br |
| 1045 | 3,4-F$_2$ | 4-Br |
| 1046 | 3,5-F$_2$ | 4-Br |
| 1047 | 3,4,5-F$_3$ | 4-Br |
| 1048 | 3-F, 4-Cl | 4-Br |
| 1049 | 3-F, 4-Br | 4-Br |
| 1050 | 3-CN, 4-F | 4-Br |
| 1051 | 3-Br, 4-F | 4-Br |
| 1052 | 3-Cl, 4-F | 4-Br |
| 1053 | 3,4-Cl$_2$ | 4-Br |
| 1054 | H | 4-OMe |
| 1055 | 2-F | 4-OMe |
| 1056 | 3-F | 4-OMe |
| 1057 | 4-F | 4-OMe |
| 1058 | 3-Cl | 4-OMe |
| 1059 | 4-Cl | 4-OMe |
| 1060 | 3-Br | 4-OMe |
| 1061 | 4-Br | 4-OMe |
| 1062 | 3-I | 4-OMe |
| 1063 | 3-CN | 4-OMe |
| 1064 | 4-CN | 4-OMe |
| 1065 | 3-NO$_2$ | 4-OMe |
| 1066 | 3-Me | 4-OMe |
| 1067 | 4-Me | 4-OMe |
| 1068 | 2,3-F$_2$ | 4-OMe |
| 1069 | 2,4-F$_2$ | 4-OMe |
| 1070 | 2,5-F$_2$ | 4-OMe |
| 1071 | 2,6-F$_2$ | 4-OMe |
| 1072 | 3,4-F$_2$ | 4-OMe |
| 1073 | 3,5-F$_2$ | 4-OMe |
| 1074 | 3,4,5-F$_3$ | 4-OMe |
| 1075 | 3-F, 4-Cl | 4-OMe |
| 1076 | 3-F, 4-Br | 4-OMe |
| 1077 | 3-CN, 4-F | 4-OMe |
| 1078 | 3-Br, 4-F | 4-OMe |
| 1079 | 3-Cl, 4-F | 4-OMe |
| 1080 | 3,4-Cl$_2$ | 4-OMe |
| 1081 | H | 3,4,5-F3 |
| 1082 | 2-F | 3,4,5-F3 |
| 1083 | 3-F | 3,4,5-F3 |
| 1084 | 4-F | 3,4,5-F3 |
| 1085 | 3-Cl | 3,4,5-F3 |
| 1086 | 4-Cl | 3,4,5-F3 |
| 1087 | 3-Br | 3,4,5-F3 |
| 1088 | 4-Br | 3,4,5-F3 |
| 1089 | 3-I | 3,4,5-F3 |
| 1090 | 3-CN | 3,4,5-F3 |
| 1091 | 4-CN | 3,4,5-F3 |
| 1092 | 3-NO2 | 3,4,5-F3 |
| 1093 | 3-Me | 3,4,5-F3 |
| 1094 | 4-Me | 3,4,5-F3 |
| 1095 | 2,3-F2 | 3,4,5-F3 |
| 1096 | 2,4-F2 | 3,4,5-F3 |
| 1097 | 2,5-F2 | 3,4,5-F3 |
| 1098 | 2,6-F2 | 3,4,5-F3 |
| 1099 | 3,4-F2 | 3,4,5-F3 |
| 1100 | 3,5-F2 | 3,4,5-F3 |
| 1101 | 3,4,5-F3 | 3,4,5-F3 |
| 1102 | 3-F, 4-Cl | 3,4,5-F3 |
| 1103 | 3-F, 4-Br | 3,4,5-F3 |
| 1104 | 3-CN, 4-F | 3,4,5-F3 |
| 1105 | 3-Br, 4-F | 3,4,5-F3 |
| 1106 | 3-Cl, 4-F | 3,4,5-F3 |
| 1107 | 3,4-Cl2 | 3,4,5-F3 |

Particularly preferred compounds of the formulae (Ib) and (Ia) according to the invention and/or their salts are characterized in that $(R^2)_n$ represents n substituents $R^2$, where, in the case that n=1, the substituent $R^2$ or, in the case that n is greater than 1, each of the substituents $R^2$ independently of the others represents fluorine, chlorine, bromine, iodine, cyano, methyl, ethyl, methoxy, methylthio, methylsulphinyl, methylsulphonyl, trifluoromethyl, trifluoromethoxy, trifluoroalkylthio, trifluoromethylsulphinyl or trifluoromethylsulphonyl, and $(R^3)_m$ represents m substituents $R^3$, where, in the case that m=1, the substituent $R^3$ or, in the case that m is greater than 1, each of the substituents $R^3$ independently of the others represents fluorine, chlorine, bromine, iodine, cyano, nitro, methyl, methoxy (here preferably 2-methoxy, 3-methoxy), methylthio, methylsulphinyl, methylsulphonyl, trifluoromethyl, trifluoromethoxy, trifluoroalkylthio, trifluoromethylsulphinyl or trifluoromethylsulphonyl, and m represents 0, 1, 2, 3, 4 or 5, preferably 0, 1, 2, 3 or 4, in particular 0, 1, 2 or 3, and n represents 0, 1, 2, 3, 4 or 5, preferably 0, 1, 2 or 3, in particular 0, 1 or 2, except for the compounds in which $R^1$=H, n=1, m=1 and $R^2$=$R^3$=4-OMe.

Especially preferred compounds of the formulae (Ib) and (Ia) according to the invention and/or their salts are characterized in that $(R^2)_n$ represents 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-$CF_3$, 3-$CF_3$, 4-$CF_3$, 2-methoxy, 3-methoxy, 4-methoxy, 2-ethoxy, 3-ethoxy, 4-ethoxy, 2-methylthio, 3-methylthio, 4-methylthio, 2-methylsulphinyl, 3-methylsulphinyl, 4-methylsulphinyl, 2-methylsulphonyl, 3-methylsulphonyl, 4-methylsulphonyl, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-3-F), (3-Br-4-F), (3-Br-5-F), (4-Br-3-Cl), (3-Br-4-Cl), (4-CN-3-F), (3-CN-4-F), (3-CN-5-F), (4-CN-3-Cl), (3-CN-4-Cl), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or (2,6-$F_2$-4-Cl),
and $(R^3)_m$ 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-$CF_3$, 3-$CF_3$, 4-$CF_3$, 2-methoxy, 3-methoxy, 2-ethoxy, 3-ethoxy, 4-ethoxy, 2-methylthio, 3-methylthio, 4-methylthio, 2-methylsulphinyl, 3-methylsulphinyl, 4-methylsulphinyl, 2-methylsulphonyl, 3-methylsulphonyl, 4-methylsulphonyl, 2-nitro, 3-nitro, 4-nitro, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, 2,5-dicyano, 2,6-dicyano, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-2-F), (4-Br-3-F), (4-CN-3-F), (4-$NO_2$-3-F), (4-OMe-3-F), (3-CN-4-F), (3-$NO_2$-4-F), (3-CN-4-Cl), (3-$NO_2$-4-Cl), (5-CN-2-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or (2,6-$F_2$-4-Cl).

Compounds of the formula (Ib) or (Ia) according to the invention which are likewise preferred are described in the Examples Section below in Tables 2, 2a-2f and U1 to U3.

Preference according to the invention is given to compounds of the formula (Ib) or (Ia) or salts thereof in which n>0.

Preference according to the invention is likewise given to compounds of the formula (Ib) or (Ia) or salts thereof in which m>0.

In preferred compounds of the formula (Ib) or (Ia) according to the invention or salts thereof, the sum of m+n=2, 3, 4 or 5.

For preferred compounds of the formula (Ia) or (Ib) according to the invention, m is greater than or equal to 1, preferably greater than or equal to 2, and the following applies:

one, more than one or all radicals $R^2$ are selected from the group consisting of F, Cl, Br, I, methyl and CN,
and
one, more than one or all radicals $R^3$ are selected from the group consisting of F, Cl, Br, methyl, methoxy, nitro and CN.

For preferred compounds of the formula (Ia) or (Ib) according to the invention, the following applies:
n is greater than or equal to 1,
m is greater than or equal to 1, preferably greater than or equal to 2,
one, more than one or all radicals $R^2$ are selected from the group consisting of F, Cl, Br, I, methyl and CN,
and
one, more than one or all radicals $R^3$ are selected from the group consisting of F, Cl, Br, methyl, methoxy and CN.

Particular preference according to the invention is given to compounds of the formula (Ib) or (Ia) or salts thereof where the following applies:

n=1, 2 or 3, and at least one $R^2$ is selected, preferably all $R^2$ are selected, from the group consisting of fluorine, chlorine and bromine,
and/or
m=1, 2 or 3, and at least one $R^3$ is selected, preferably all $R^3$ are selected, from the group consisting of fluorine and chlorine.

Preference according to the invention is given to
compounds of the formula (I) or salts thereof in which $(R^2)_n$ represents 3-chloro and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-$F_2$-4-Cl);

compounds of the formula (I) or salts thereof in which $(R^2)_n$ represents 4-chloro and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-$F_2$-4-Cl);

compounds of the formula (I) or salts thereof in which $(R^2)_n$ represents 2-fluoro and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-$F_2$-4-Cl);

compounds of the formula (I) or salts thereof in which $(R^2)_n$ represents 3-fluoro and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-$F_2$-4-Cl);

compounds of the formula (I) or salts thereof in which $(R^2)_n$ represents 4-fluoro and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F$_2$-4-Cl);

compounds of the formula (I) or salts thereof in which $(R^2)_n$ represents 3-bromo and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F$_2$-4-Cl);

compounds of the formula (I) or salts thereof in which $(R^2)_n$ represents (3-CN) and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F$_2$-4-Cl);

compounds of the formula (I) or salts thereof in which $(R^2)_n$ represents 3,4-difluoro and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F$_2$-4-Cl);

compounds of the formula (I) or salts thereof in which $(R^2)_n$ represents 3,4-dichloro and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F$_2$-4-Cl);

compounds of the formula (I) or salts thereof in which $(R^2)_n$ represents 3,5-difluoro and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F$_2$-4-Cl);

compounds of the formula (I) or salts thereof in which $(R^2)_n$ represents 3,5-dichloro and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F$_2$-4-Cl);

compounds of the formula (I) or salts thereof in which $(R^2)_n$ represents (3-Cl-4-F) and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F$_2$-4-Cl);

compounds of the formula (I) or salts thereof in which $(R^2)_n$ represents (4-Cl-3-F) and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F$_2$-4-Cl);

compounds of the formula (I) or salts thereof in which $(R^2)_n$ represents (3-Br-4-F) and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F$_2$-4-Cl);

compounds of the formula (I) or salts thereof in which $(R^2)_n$ represents (3-CN-4-F) and $(R^3)_m$ represents 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F$_2$-4-Cl), where in each case the compounds where $R^1$=H are in turn preferred.

Particular preference according to the invention is given to compounds of the formula (Ib) or (Ia) or salts thereof in which $(R^2)_n$ has one of the meanings below:
3-chloro, 3-fluoro, 4-fluoro, 3-bromo, 3-cyano, 3,4-difluoro, (3-Cl-4-F), (3-Br-4-F), (3-CN-4-F),
and/or
$(R^3)_m$ has one of the meanings below:
2-fluoro, 3-fluoro, 4-fluoro, 2,5-difluoro, 2,6-difluoro, 3,5-difluoro, 2,3,6-trifluoro, 2,4,6-trifluoro, 2,6-F2-4-Cl, 3-chloro, 4-chloro.

In general, from among the compounds having the above-mentioned meanings for individual groups or combinations of groups $R^1$, $(R^2)_n$ and/or $(R^3)_m$, preference is given to those in which the remaining groups or combinations of groups in the compounds are defined according to the meanings mentioned as preferred.

Furthermore, it has been found that the compounds of the formula (I) to be used according to the invention or the compounds of the formula according to the invention and/or their salts which are (2,3)-threo-configured have better herbicidal properties than the corresponding (2,3)-erythro-configured compounds. Accordingly, (2,3)-threo-configured compounds of the formulae (I), (Ib) and (Ia) and their salts are preferred. This applies accordingly to compositions according to the invention.

Accordingly, preference according to the invention is given to mixtures and compositions in which the molar ratio of a (2,3)-threo-configured compound of the formula (I) to the corresponding (2,3)-erythro-configured compound of the formula (I) is greater than 1, more preferably greater than 2, particularly preferably greater than 3 and especially preferably greater than 4.

Likewise, preference according to the invention is given to mixtures and compositions in which the weight ratio of the total amount of (2,3)-threo-configured compounds of the formulae (I), (Ib) and (Ia) to the total amount of (2,3)-erythro-configured compounds of the formulae (I), (Ib) and (Ia) is greater than 1, more preferably greater than 2, particularly preferably greater than 3 and especially preferably greater than 4.

Surprisingly, it has furthermore been found that optically active threo-configured compounds of the formula (I) and their salts have particularly good herbicidal activities and at the same time advantageous selectivities with respect to some useful plants.

Accordingly, in the context of the present invention preference is given to compounds of the formula (I) and their salts having a (2,3)-threo-configuration, i.e. compounds of the formulae (threo-1-I) and (threo-2-I) below

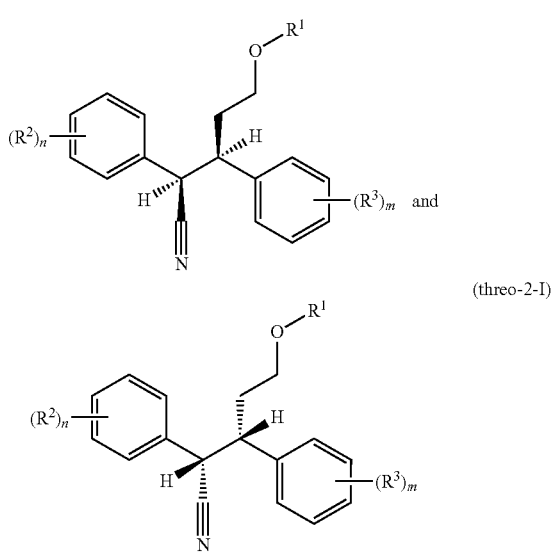

(threo-1-I)

(threo-2-I)

in which
$R^1$, $R^2$, $R^3$, n and m each have the meaning mentioned above, preferably one of the meanings given as being preferred or particularly preferred.

In the context of the present invention preference is given to compounds of the formula (Ia) and their salts having a (2,3)-threo-configuration, i.e. compounds of the formulae (threo-1-Ia) and/or (threo-2-Ia) below

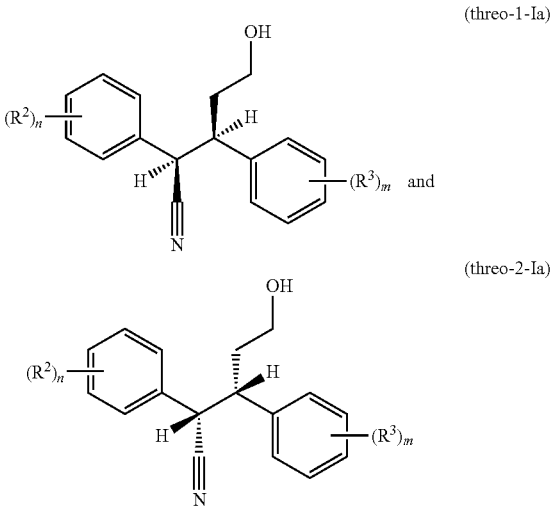

(threo-1-Ia)

(threo-2-Ia)

in which
$R^1$, $R^2$, $R^3$, n and m each have the meaning mentioned above, preferably one of the meanings given as being preferred or particularly preferred.

The stereochemical configuration at the carbon atom in position 2 of the pentanonitrile derivative of the formula (I), (Ib) or (Ia) preferably has a stereochemical purity of from 60 to 100% (S), with preference from 70 to 100% (S), more preferably from 80 to 100% (S), especially preferably from 90 to 100% (S), and the stereochemical configuration at the carbon atom in position 3 of the pentanonitrile derivative preferably has a stereochemical purity of from 60 to 100% (S), with preference from 70 to 100% (S), more preferably from 80 to 100% (S), especially preferably from 90 to 100% (S), in each case based on the total amount of the threo-enantiomers in question.

The stereochemical configuration at the carbon atom in position 2 of the pentanonitrile derivative of the formula (I), (Ib) or (Ia) preferably has a stereochemical purity of from 60 to 100% (R), with preference from 70 to 100% (R), more preferably from 80 to 100% (R), especially preferably from 90 to 100% (R), and the stereochemical configuration at the carbon atom in position 3 of the pentanonitrile derivative preferably has a stereochemical purity of from 60 to 100% (R), with preference from 70 to 100% (R), more preferably from 80 to 100% (R), especially preferably from 90 to 100% (R), in each case based on the total amount of the threo-enantiomers in question.

By virtue of their even better property profile, in particular their even better herbicidal activity, special preference is given to the (2R,3R)-configured pentanonitrile derivatives of the formulae (I), (Ib) and (Ia), preferably in the stereochemical purities stated above. As a consequence, the compounds of the formulae (threo-1-I) and (threo-1-Ia) are particularly preferred in the context of the present invention. The absolute configuration of these (2R,3R)-configured pentanonitrile derivatives was assigned by X-ray structural analysis.

What was said above applies accordingly to mixtures according to the invention and compositions according to the invention.

The compounds of the formula (I) according to the invention can be prepared by various processes.

In the processes described below, in some cases solvents are employed. In this context, "inert solvents" refers in each case to solvents which are inert under the particular reaction conditions, but which do not have to be inert under any reaction conditions. In the processes below, the reactions described can alternatively also be carried out in a microwave reactor.

The compounds according to the invention and the compounds to be used according to the invention can be prepared by methods known per se. Here, the starting material may, for example, be compounds of the formula (E). Compounds of the formula (E) are known from the prior art, for example from WO 2012/126765 A1. The scheme below shows, in an exemplary manner, how the compounds according to the invention or the compounds to be used according to the invention can be prepared.

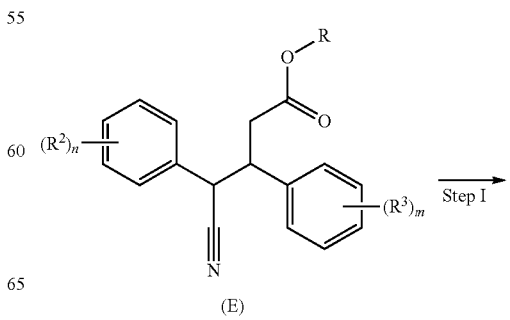

(E)

Step I

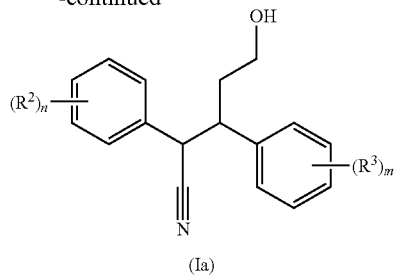

(Ia)

Step II | R¹—X¹

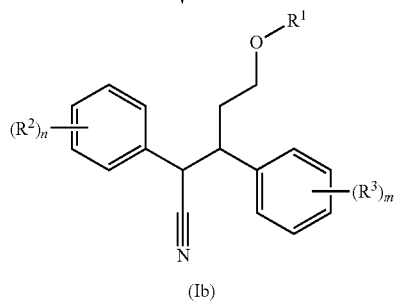

(Ib)

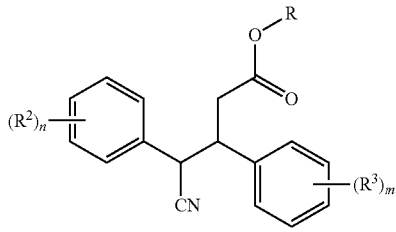

(E)

is converted by reduction into a compound of the formula (Ia)

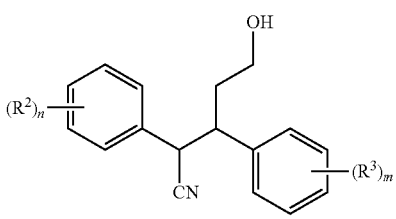

(Ia)

and the compound (Ia) is optionally reacted further to give a compound of the formula (I), provided R¹ does not represent hydrogen, where R represents hydrogen or an organic radical, preferably a radical selected from the group of the radicals defined above for R¹, with preference selected from one of the radicals characterized as being preferred, and R², R³, m and n each have the meaning defined above, and are preferably in each case selected from one of the groups of radicals characterized as being preferred.

The starting materials (E) used for preparing the compounds of the formula (Ia) or (I) are known from the literature cited or can be prepared analogously to the literature cited.

To prepare the compounds (Ia) or (I) according to the invention, it is also possible to use the corresponding diastereomer mixtures in the form of their racemic mixtures.

If stereochemically enriched compounds of the formula (E) mentioned above are used for the process according to the invention, it is possible to obtain the corresponding stereochemically enriched compounds of the formula (Ia) or (I).

Solvents suitable for this purpose are, for example, organic solvents such as:

aliphatic hydrocarbons such as pentane, hexane, cyclohexane or petroleum ether;

aromatic hydrocarbons such as toluene, o-, m- or p-xylene, halogenated hydrocarbons such as methylene chloride, chloroform or chlorobenzene, ethers, such as diethyl ether, diisopropyl ether, tert-butyl methyl ether, dioxane, anisole and tetrahydrofuran (THF), nitriles such as acetonitrile or propionitrile, ketones such as acetone, methyl ethyl ketone, diethyl ketone and tert-butyl methyl ketone, dimethyl sulphoxide, dimethylformamide, dimethylacetamide, sulpholane, and also mixtures of the organic solvents mentioned.

Here, R¹, R², R³, n and m each have the (preferred or particularly preferred) meaning mentioned above, and R represents hydrogen or an organic radical, preferably a radical selected from the group of the radicals defined above for R¹.

With respect to "Step 1" of the above scheme:

Methods for the selective reduction of compounds of the formula (E) to give corresponding compounds of the formula (Ia) are known to the person skilled in the art from the prior art and described, for example, in European Journal of Organic Chemistry 2009, (11), 1806-1811 or in WO 2012/076513 A1. Preferably, the selective reduction in question is carried out using borohydrides, with preference using borohydrides of alkali borohydrides, in particular of lithium borohydride, sodium borohydride or potassium borohydride, and in turn preferably in the presence of a lithium halide, preferably in the presence of lithium chloride. Here, this reduction can be carried out in a protic organic solvent such as, for example, ethanol (see, for example, WO 2011/014383), or an aprotic organic solvent such as, for example, tetrahydrofuran (THF), here preferably with heating under reflux.

With respect to "Step 2" of the above scheme:

The present optional further reaction (nucleophilic substitution) of the primary alcohol (Ia) obtained in "Step 1" with R¹—X¹ (where X¹ represents a leaving group) to give compounds of the formula (Ib) is known in principle to the person skilled in the art and described, for example, in Journal of Organic Chemistry 2011, 76(3), 811-819. Here, the nucleophilic substitution is preferably carried out in the presence of 4-(dimethylamino)pyridine. The reaction can also be carried out, for example, in an aprotic organic solvent such as tetrahydrofuran (THF) or dichloromethane, if appropriate at elevated temperature, for example by heating under reflux.

Accordingly, the present invention also relates to a process for preparing a compound of the formula (I) according to the invention or a compound of the formula (I) to be used according to the invention and/or a salt thereof, characterized in that a compound of the formula (E)

In individual cases, it is also appropriate to use inorganic solvents such as water or mixtures of organic solvents with water.

Suitable conditions and catalysts for the preparation of compounds of the formula (I) in which R1 does not represent H from compounds of the formula (Ia), for example by esterification, are known to the person skilled in the art.

The conversion of compounds of the formula (Ia) into compounds of the formula (I) in which $R^1$ does not represent H can be carried out in the presence of a base, for example a base from the group of the inorganic bases such as the alkali metal and alkaline earth metal hydroxides, for example lithium hydroxide, sodium hydroxide, potassium hydroxide or calcium hydroxide, the alkali metal and alkaline earth metal oxides, for example lithium oxide, sodium oxide, calcium oxide or magnesium oxide, the alkali metal and alkaline earth metal hydrides, for example lithium hydride, sodium hydride, potassium hydride or calcium hydride, the alkali metal amides, for example lithium amide, sodium amide or potassium amide, the alkali metal and alkaline earth metal carbonates, for example lithium carbonate, potassium carbonate or calcium carbonate, the alkali metal bicarbonates, for example sodium bicarbonate, or the organometallic compounds such as, preferably, the alkali metal alkyls, for example methyllithium, butyllithium or phenyllithium, the alkylmagnesium halides, for example methylmagnesium chloride, or the alkali metal and alkaline earth metal alkoxides, for example sodium methoxide, sodium ethoxide, potassium ethoxide, potassium tert-butoxide or dimethoxymagnesium.

The bases used can also be organic bases, for example from the group of the tertiary aliphatic amines, for example trimethylamine, triethylamine, tributylamine, diisopropylethylamine or N-methylpiperidine, or the aromatic tertiary amines, for example pyridine or substituted pyridines such as collidine, lutidine or 4-dimethylaminopyridine, or the bicyclic amines such as 7-methyl-1,5,7-triazabicyclo[4.4.0]-dec-5-ene or 1,8-diazabicyclo[5.4.0]undec-7-ene (DBU).

Preferred bases are, for example, lithium hydroxide, potassium carbonate, potassium tert-butoxide, lithium bis(trimethylsilyl)amide, pyridines, substituted pyridines, 7-methyl-1,5,7-triazabicyclo[4.4.0]-dec-5-ene or DBU.

The amount of base may generally vary within wide limits. For example, it may be expedient to employ the base in catalytic amounts, in substoichiometric amounts, in equimolar amounts or in excess. A preferably liquid organic base may optionally also be used as solvent.

Suitable catalysts for the conversion of compounds of the formula (Ia) into compounds of the formula (I), in which $R^1$ is not H, may also be acidic catalysts, for example from the group of the inorganic acids, for example Broensted acids, such as hydrofluoric acid, hydrochloric acid, hydrobromic acid, sulphuric acid or perchloric acid, or Lewis acids, such as boron trifluoride, aluminium trichloride, iron(III) chloride, tin(IV) chloride, titanium(IV) chloride, scandium(III) triflate or zinc(II) chloride, and also organic acids, for example formic acid, acetic acid, propionic acid, oxalic acid, toluenesulphonic acid, benzenesulphonic acid, camphorsulphonic acid, citric acid or trifluoroacetic acid.

The reaction mixtures obtained are worked up in a customary manner, for example by mixing with water, separating the phases and optionally chromatographic purification of the crude products. Some of the compounds are obtained in the form of colourless or slightly brownish viscous oils which are purified or freed from volatile components under reduced pressure and at moderately elevated temperature.

If the compounds are obtained as solids, the purification can also be carried out by recrystallization or digestion. If individual compounds (I) cannot be obtained in a satisfactory manner by the routes described above, they can be prepared by derivatization of other compounds (I) or (Ia).

Suitable isolation methods, purification methods and methods for separating stereoisomers of compounds of the formula (I) or (Ia) are methods generally known to the person skilled in the art from analogous cases, for example by physical processes such as crystallization, chromatographic methods, in particular column chromatography and HPLC (high pressure liquid chromatography), distillation, optionally under reduced pressure, extraction and other methods, any mixtures that remain can generally be separated by chromatographic separation, for example on chiral solid phases. Suitable for preparative amounts or on an industrial scale are processes such as the crystallization, for example of diastereomeric salts which can be obtained from the diastereomer mixtures using optically active acids and, if appropriate, provided that acidic groups are present, using optically active bases.

Optically active acids which are suitable for optical resolution by crystallization of diastereomeric salts are, for example, camphorsulphonic acid, camphoric acid, bromocamphorsulphonic acid, quinic acid, tartaric acid, dibenzoyltartaric acid and other analogous acids; suitable optically active bases are, for example, quinine, cinchonine, quinidine, brucine, 1-(S)- or 1-(R)-phenylethylamine and other analogous bases.

The crystallizations are then in most cases carried out in aqueous, alcoholic or aqueous-organic solvents, where the diastereomer which is less soluble precipitates first, if appropriate after seeding. One enantiomer of the compound of the formula (I) is then liberated from the precipitated salt, or the other is liberated from the crystallizate, by acidification or using a base.

As an alternative to the optical resolution methods mentioned, enantioselective processes starting with stereochemically pure starting materials are in principle also suitable for preparing the (threo) enantiomers.

The following acids are generally suitable for preparing the acid addition salts of the compounds of the formula (I): hydrohalic acids, such as hydrochloric acid or hydrobromic acid, furthermore phosphoric acid, nitric acid, sulphuric acid, mono- or bifunctional carboxylic acids and hydroxycarboxylic acids, such as acetic acid, maleic acid, succinic acid, fumaric acid, tartaric acid, citric acid, salicylic acid, sorbic acid, or lactic acid, and also sulphonic acids, such as p-toluenesulphonic acid and 1,5-naphthalenedisulphonic acid. The acid addition compounds of the formula (I) can be obtained in a manner known per se by the customary methods for forming salts, for example by dissolving a compound of the formula (I) in a suitable organic solvent, such as, for example, methanol, acetone, methylene chloride or benzene, and adding the acid at temperatures of from 0 to 100° C., and they can be isolated in a known manner, for example by filtration, and, if appropriate, purified by washing with an inert organic solvent.

Base addition salts of the compounds of the formula (I) can be prepared, for example, in polar solvents such as, for example, water, methanol or acetone, at temperatures of from 0 to 100° C. Examples of bases which are suitable for the preparation of such salts are, for example, alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alkoxides and alkaline earth metal alkoxides, for example sodium methoxide or potassium tert-butoxide, or ammonia, ethanolamine or quaternary ammonium hydroxide.

A collection of compounds of the formula (I) can additionally be prepared in a parallel or combinatorial manner, it being possible for this to take place in a manual, partly automated or completely automated manner. In this connection, it is possible to automate the reaction procedure, the work-up or the purification of the products and/or intermediates.

For the parallelized reaction procedure and work-up it is possible to use a range of commercially available instruments, of the kind offered by, for example, the companies Stem Corporation, Woodrolfe Road, Tollesbury, Essex, CM9 8SE, England, or H+P Labortechnik GmbH, Bruckmannring 28, 85764 OberschleiBheim, Germany. For the parallel purification of compounds (I) or of intermediates produced during the preparation, there are available, inter alia, chromatography apparatuses, for example from ISCO, Inc., 4700 Superior Street, Lincoln, Nebr. 68504, USA. The apparatuses listed allow a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Zymark Corporation, Zymark Center, Hopkinton, Mass. 01748, USA.

Besides the methods described, the preparation of compounds of the formula (I) can take place completely or partially by solid-phase-supported methods. For this purpose, individual intermediates or all intermediates in the synthesis or a synthesis adapted for the corresponding procedure are bonded to a synthesis resin. Solid-phase-supported synthesis methods are described extensively in the specialist literature, for example: Barry A. Bunin in "The Combinatorial Index", Academic Press, 1998.

The use of solid-phase-supported synthesis methods permits a number of protocols, which are known from the literature and which for their part may be performed manually or in an automated manner, to be carried out. For example, the so-called "tea bag method" (U.S. Pat. No. 4,631,211) in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation according to the processes described herein produces compounds of the formula (I) in the form of substance collections or libraries. Accordingly, the present invention also provides libraries of compounds of the formula (I) which comprise at least two compounds of the formula (I), and precursors thereof.

The present invention furthermore provides a method for controlling harmful plants and/or for regulating the growth of plants, characterized in that an effective amount
of one or more compounds of the formula (I) and/or salts thereof, as defined above,
of one or more compounds of the formula (Ib) and/or salts thereof, as defined above,
of one or more compounds of the formula (Ia) and/or salts thereof, as defined above, or
of a composition, as defined above,
is applied to the (harmful) plants, seeds of (harmful) plants, the soil in which or on which the (harmful) plants grow or the area under cultivation.

The present invention also provides a method for controlling unwanted plants, preferably in crops of useful plants, characterized in that an effective amount
of one or more compounds of the formula (I) and/or salts thereof, as defined above,
of one or more compounds of the formula (Ib) and/or salts thereof, as defined above,
of one or more compounds of the formula (Ia) and/or salts thereof, as defined above, or
of a composition according to the invention, as defined above,
is applied to unwanted plants (for example harmful plants such as mono- or dicotyledonous weeds or unwanted crop plants), the seed of the unwanted plants (i.e. plant seeds, for example grains, seeds or vegetative propagation organs such as tubers or shoot parts with buds), the soil in which or on which the unwanted plants grow (for example the soil of crop land or non-crop land) or the area under cultivation (i.e. the area on which the unwanted plants will grow).

The present invention furthermore also provides methods for regulating the growth of plants, preferably of useful plants, characterized in that an effective amount
of one or more compounds of the formula (I) and/or salts thereof, as defined above,
of one or more compounds of the formula (Ib) and/or salts thereof, as defined above,
of one or more compounds of the formula (Ia) and/or salts thereof, as defined above, or
of a composition according to the invention, as defined above,
is applied to the plant, the seed of the plant (i.e. plant seed, for example grains, seeds or vegetative propagation organs such as tubers or shoot parts with buds), the soil in which or on which the plants grow (for example the soil of crop land or non-crop land) or the area under cultivation (i.e. the area on which the plants will grow).

In this context, the compounds according to the invention or the compounds to be used according to the invention or the compositions according to the invention can be applied for example by pre-sowing (if appropriate also by incorporation into the soil), pre-emergence and/or post-emergence processes. Specific examples of some representatives of the monocotyledonous and dicotyledonous weed flora which can be controlled by the compounds according to the invention are as follows, though there is no intention to restrict the enumeration to particular species.

In a method according to the invention for controlling harmful plants or for regulating the growth of plants, one or more compounds of the formula (I), (Ia), (Ib) and/or salts thereof are preferably employed for controlling harmful plants or for regulating growth in crops of useful plants or ornamental plants, where in a preferred embodiment the useful plants or ornamental plants are transgenic plants.

The compounds of the formula (I), (Ia), (Ib) according to the invention or the compounds of the formula (I), (Ia), (Ib) to be used according to the invention and/or their salts are suitable for controlling the following genera of monocotyledonous and dicotyledonous harmful plants:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous harmful plants of the genera: *Abutilon, Amaranthus, Ambrosia, Anoda, Anthemis, Aphanes, Artemisia, Atriplex, Bellis, Bidens, Capsella, Carduus, Cassia,*

*Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds according to the invention or the compounds to be used according to the invention are applied to the soil surface before germination of the harmful plants (weed grasses or broad-leaves weeds) (pre-emergence method), either the seedlings of the weed grasses or broad-leaves weeds are prevented completely from emerging or they grow until they have reached the cotyledon stage, but then stop growing and eventually, after three to four weeks have elapsed, die completely.

If the active compounds are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a lasting manner.

Although the compounds to be used according to the invention or the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, are damaged only to an insignificant extent, or not at all, depending on the structure of the respective compound according to the invention and its application rate. For these reasons, the present compounds are very suitable for selective control of unwanted plant growth in plant crops such as agriculturally useful plants or ornamental plants.

In addition, the compounds according to the invention (depending on their particular structure and the application rate deployed) have outstanding growth-regulating properties in crop plants. They intervene in the plant's own metabolism with a regulatory effect, and can thus be used to control in a targeted manner plant constituents and to facilitate harvesting, for example by triggering desiccation and stunted growth. Moreover, they are also suitable for generally controlling and inhibiting unwanted vegetative growth without destroying the plants in the process Inhibiting vegetative growth plays a major role for many monocotyledonous and dicotyledonous crops, since, for example, this can reduce or completely prevent lodging.

By virtue of their herbicidal and plant-growth-regulating properties, the active compounds can also be used for controlling harmful plants in crops of genetically modified plants or plants modified by conventional mutagenesis. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with increased starch content or altered starch quality, or those with a different fatty acid composition of the harvested material.

It is preferred with a view to transgenic crops to use the compounds according to the invention and/or their salts in economically important transgenic crops of useful plants and ornamentals, for example of cereals such as wheat, barley, rye, oats, millet, rice and maize or else crops of sugar beet, cotton, soybean, oilseed rape, potato, tomato, peas and other vegetables.

It is preferred to employ the compounds according to the invention as herbicides in crops of useful plants which are resistant, or have been made resistant by recombinant means, to the phytotoxic effects of the herbicides.

By virtue of their herbicidal and plant-growth-regulatory properties, the active compounds can also be employed for controlling harmful plants in crops of known genetically modified plants or genetically modified plants still to be developed. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with increased starch content or altered starch quality, or those with a different fatty acid composition of the harvested material. Further special properties may be tolerance or resistance to abiotic stress factors, for example heat, cold, drought, salinity and ultraviolet radiation.

Preference is given to the use of the compounds of the formula (I) according to the invention or salts thereof in economically important transgenic crops of useful plants and ornamental plants, for example of cereals such as wheat, barley, rye, oats, triticale, millet, rice, cassava and corn, or else crops of sugar beet, cotton, soybean, oilseed rape, potatoes, tomatoes, peas and other vegetables.

It is preferred to employ the compounds of the formula (I) according to the invention as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

genetic modifications of crop plants for the purpose of modifying the starch synthesized in the plants (for example WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or of the sulphonylurea type (EP-A-0257993, U.S. Pat. No. 5,013,659), transgenic crop plants, for example cotton, with the ability to produce *Bacillus thuringiensis* toxins (Bt toxins) which make the plants resistant to particular pests (EP-A-0142924, EP-A-0193259), transgenic crop plants with a modified fatty acid composition (WO 91/13972),
genetically modified crop plants with novel plant constituents or secondary metabolites, for example novel phytoalexins, which bring about an increased disease resistance (EP-A-309862, EP-A-0464461),
genetically modified plants with reduced photorespiration, which feature higher yields and higher stress tolerance (EP-A-0305398),
transgenic crop plants which produce pharmaceutically or diagnostically important proteins ("molecular pharming"),
transgenic crop plants which are distinguished by higher yields or better quality,
transgenic crop plants which are distinguished by a combination, for example of the abovementioned novel properties ("gene stacking").

A large number of molecular-biological techniques by means of which novel transgenic plants with modified properties can be generated are known to the person skilled in the art. To carry out such recombinant manipulations, nucleic acid molecules which allow mutagenesis or a sequence change by recombination of DNA sequences can be introduced into plasmids. With the aid of standard methods, it it possible, for example, to undertake base exchanges, remove parts of sequences or add natural or synthetic sequences. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227) The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds (I) according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulphonylureas, glyphosate, glufosinate or benzoylisoxazoles and analogous active compounds.

On employment of the active compounds according to the invention in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the formula (I) according to the invention and/or their salts as herbicides for controlling harmful plants in crops of useful plants or ornamentals, optionally in transgenic crop plants.

Preference is given to the use in cereals, here preferably maize, wheat, barley, rye, oats, millet or rice, by the pre- or post-emergence method.

Preference is also given to the use in soya beans by the pre- or post-emergence method.

The use according to the invention for the control of harmful plants or for growth regulation of plants also includes the case in which the active compound of the formula (I) or its salt is not formed from a precursor substance ("prodrug") until after application on the plant, in the plant or in the soil.

The invention also provides the use of one or more compounds of the formula (I) or salts thereof or of a composition according to the invention (as defined below) (in a method) for controlling harmful plants or for regulating the growth of plants which comprises applying an effective amount of one or more compounds of the formula (I) or salts thereof onto the plants (harmful plants, if appropriate together with the useful plants), plant seeds, the soil in which or on which the plants grow or the area under cultivation.

The invention also provides a herbicidal or plant growth-regulating composition, characterized in that the composition (a) comprises one or more compounds of the formula (I) and/or salts thereof as defined above, preferably one or more compounds of the formula (Ib) or (Ia) and/or salts thereof, in each case as defined above,
and
(b) one or more further substances selected from groups (i) and/or (ii):
(i) one or more further agrochemically active substances, preferably selected from the group consisting of insecticides, acaricides, nematicides, further herbicides (i.e. those not corresponding to the formula (I) defined above), fungicides, safeners, fertilizers and/or further growth regulators,
(ii) one or more formulation auxiliaries customary in crop protection.

A herbicidal or plant growth-regulating composition according to the invention comprises preferably one, two, three or more formulation auxiliaries (ii) customary in crop protection selected from the group consisting of surfactants, emulsifiers, dispersants, film-formers, thickeners, inorganic salts, dusting agents, carriers solid at 25° C. and 1013 mbar, preferably absorbant granulated inert materials, wetting agents, antioxidants, stabilizers, buffer substances, antifoam agents, water, organic solvents, preferably organic solvents miscible with water in any ratio at 25° C. and 1013 mbar.

The compounds (I) according to the invention can be used in the form of wettable powders, emulsifiable concentrates, sprayable solutions, dusting products or granules in the customary formulations. The invention therefore also provides herbicidal and plant growth-regulating compositions which comprise compounds of the formula (I) and/or salts thereof.

The compounds of the formula (I) and/or salts thereof can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types and the formulation assistants, such as inert materials, surfactants, solvents and further additives, are known to the person skilled in the art and are described, for example, in: Watkins, "Handbook of Insecticide Dust Diluents and Carriers", 2nd ed., Darland Books, Caldwell N.J., H.v. Olphen, "Introduction to Clay Colloid Chemistry"; 2nd ed., J. Wiley & Sons, N.Y.; C. Marsden, "Solvents Guide"; 2nd ed., Interscience, N. Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie", volume 7, C. Hanser Verlag Munich, 4th ed. 1986.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulphates, alkanesulphonates, alkylbenzenesulphonates, sodium lignosulphonate, sodium 2,2'-dinaphthylmethane-6,6'-disulphonate, sodium dibutylnaphthalenesulphonate or else sodium oleoylmethyltaurinate. To prepare the wettable powders, the herbicidally active compounds are ground finely, for example in customary apparatus such as hammer mills, blower mills and air-jet mills, and simultaneously or subsequently mixed with the formulation assistants.

Emulsifiable concentrates are produced by dissolving the active compound in an organic solvent, for example butanol, cyclohexanone, dimethylformamide, xylene or else relatively high-boiling aromatics or hydrocarbons or mixtures of the organic solvents, with addition of one or more surfactants of the ionic and/or nonionic type (emulsifiers). Emulsifiers used may, for example, be: calcium alkylarylsulphonates such as calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active substance onto adsorptive granular inert material or by applying active substance concentrates to the surface of carriers, such as sand, kaolinites or granular inert material, by means of adhesives, for example polyvinyl alcohol, sodium polyacrylates or mineral oils. Suitable active compounds can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical preparations, preferably herbicidal or plant growth-regulating compositions, of the present invention preferably comprise a total amount of from 0.1 to 99% by weight, preferably 0.5 to 95% by weight, particularly preferably 1 to 90% by weight, especially preferably 2 to 80% by weight, of active compounds of the formula (I) and their salts.

In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partly on whether the active compound is present in liquid or solid form and on which granulation assistants, fillers, etc., are used. In the water-dispersible granules, the content of active compound is, for example, between 1 and 95% by weight, preferably between 10 and 80% by weight.

In addition, the active compound formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described, inter alia, in "Chemistry and Technology of Agrochemical Formulations", ed. D. A. Knowles, Kluwer Academic Publishers (1998).

The compounds of the formula (I) or salts thereof can be employed as such or in the form of their preparations (formulations) combined with other pesticidally active compounds, such as, for example, insecticides, acaricides, nematicides, herbicides, fungicides, safeners, fertilizers and/or growth regulators, for example as finished formulation or as tank mixes. The combination formulations can be prepared on the basis of the abovementioned formulations, while taking account of the physical properties and stabilities of the active compounds to be combined.

Active compounds which can be employed in combination with the compounds of formula (I) to be used according to the invention or the compounds of formula (I) according to the invention in mixture formulations or in a tank mix are, for example, known active compounds based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 16th edition, The British Crop Protection Council and the Royal Soc. of Chemistry, 2012 and literature cited therein. Known herbicides or plant growth regulators which can be combined with the compounds according to the invention are, for example, the following active compounds (the compounds are either designated by the common name according to the International Organization for Standardization (ISO) or by the chemical name, or by the code number) and always comprise all use forms such as acids, salts, esters and isomers such as stereoisomers and optical isomers.

The following compounds may be mentioned as examples of combination partners for the compounds of the formula (I), (Ia) or (Ib) to be used according to the invention or the compounds of the formula (I), (Ia) or (Ib) according to the invention:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, glyphosate-potassium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid, 4-indol-3-ylbutyric acid, iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]
methy}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

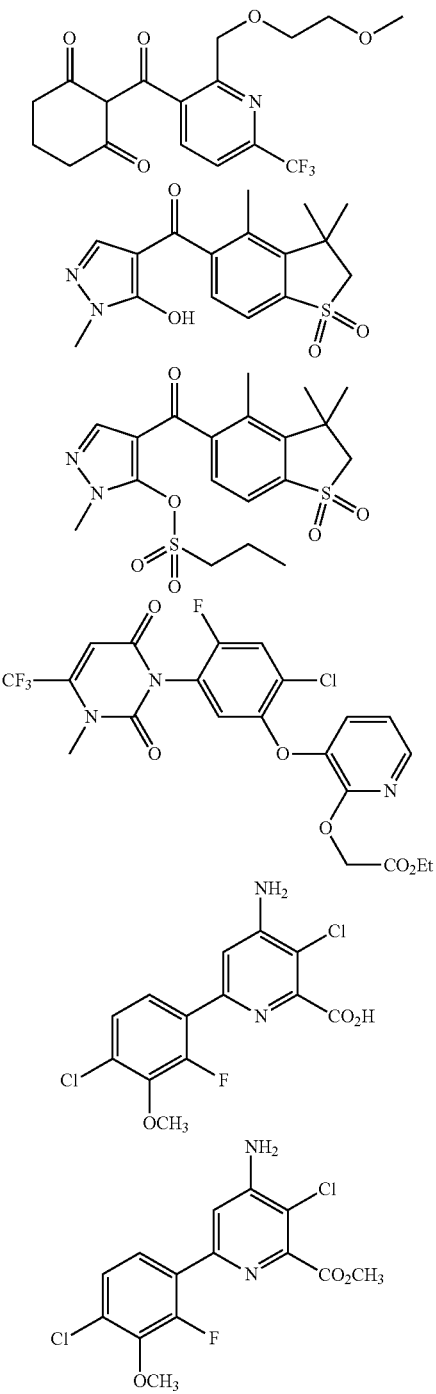

Of particular interest is the selective control of harmful plants in crops of useful plants and ornamentals. Although the compounds (I) according to the invention have already demonstrated very good to adequate selectivity in a large number of crops, in principle, in some crops and in particular also in the case of mixtures with other, less selective herbicides, phytotoxicities on the crop plants may occur. In this connection, combinations of compounds (I) according to the invention are of particular interest which comprise the compounds (I) or their combinations with other herbicides or pesticides and safeners. The safeners, which are used in an antidotically effective amount, reduce the phytotoxic side effects of the herbicides/pesticides employed, for example in economically important crops, such as cereals (wheat, barley, rye, corn, rice, millet), sugarbeet, sugarcane, oilseed rape, cotton and soybeans, preferably cereals. The following groups of compounds are suitable, for example, as safeners for the compounds (I) and their combinations with further pesticides:

A) compounds of the formula (S-I)

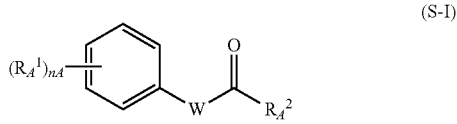

where the symbols and indices have the following meanings:

$n_A$ is a natural number from 0 to 5, preferably from 0 to 3;

$R_A^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group of the partially unsaturated or aromatic five-membered heterocycles having 1 to 3 ring heteroatoms of the N or O type, where at least one nitrogen atom and at most one oxygen atom is present in the ring, preferably a radical from the group of $(W_A^1)$ to $(W_A^4)$,

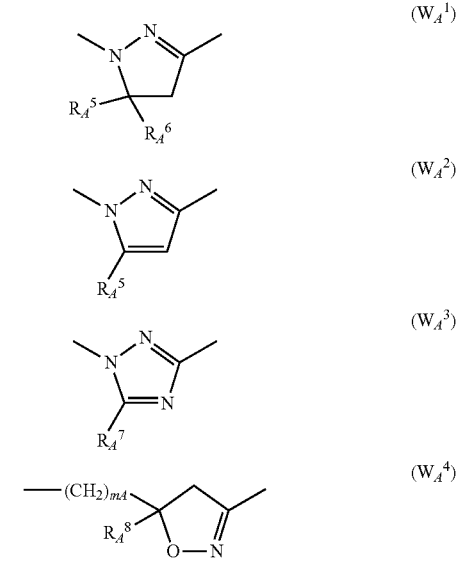

$m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group of O and S, which is joined to the carbonyl group in (S-I) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$;

$R_A^3$ is hydrogen or an unsubstituted or substituted aliphatic hydrocarbyl radical preferably having a total of 1 to 18 carbon atoms;

$R_A^4$ is hydrogen, $(C_1-C_6)$-alkyl, $(C_1-C_6)$-alkoxy or substituted or unsubstituted phenyl;

$R_A^5$ is H, $(C_1-C_8)$-alkyl, $(C_1-C_8)$-haloalkyl, $(C_1-C_4)$-alkoxy $(C_1-C_8)$-alkyl, cyano or $COOR_A^9$ in which $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the type of the dichlorophenylpyrazoline-3-carboxylic acid, preferably compounds such as ethyl 1(2,4-dichlorophenyl)-5-(ethoxycarbonyl)-5-methyl-2-pyrazoline-3-carboxylate (S1-1) ("mefenpyr-diethyl", see Pestic. Man.), and related compounds as described in WO 91/07874;

b) derivatives of dichlorophenylpyrazolecarboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (51-5) and related compounds as described in EP-A-333 131 and EP-A-269 806;

c) compounds of the triazolecarboxylic acid type, preferably compounds such as fenchlorazole(-ethyl), i.e. ethyl 1-(2,4-dichlorophenyl)-5-trichloromethyl-(1H)-1,2,4-triazole-3-carboxylate (S1-6), and related compounds as described in EP-A-174 562 and EP-A-346 620;

d) compounds of the type of the 5-benzyl- or 5-phenyl-2-isoxazoline-3-carboxylic acid or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9) ("isoxadifen-ethyl") or n-propyl 5,5-diphenyl-2-isoxazolinecarboxylate (S1-10) or ethyl 5-(4-fluorophenyl)-5-phenyl-2-isoxazoline-3-carboxylate (S1-11), as described in the patent application WO-A-95/07897.

B) Quinoline derivatives of the formula (S-II)

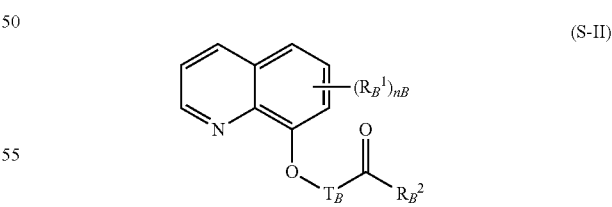

where the symbols and indices have the following meanings:

$R_B^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably from 0 to 3;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group consisting of O and S, which is joined to the carbonyl group in (S-II) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$, especially of the formula $OR_B^3$;

$R_B^3$ is hydrogen or an unsubstituted or substituted aliphatic hydrocarbyl radical preferably having a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a $(C_1$ or $C_2)$-alkanediyl chain which is unsubstituted or substituted by one or two $(C_1-C_4)$-alkyl radicals or by $[(C_1-C_3)$-alkoxy]carbonyl;

preferably:

a) compounds of the 8-quinolinoxyacetic acid type (S2), preferably
1-methylhexyl 5-chloro-8-quinolinoxyacetate (common name "cloquintocet-mexyl" (S2-1) (see Pestic. Man.),
1,3-dimethylbut-1-yl 5-chloro-8-quinolinoxyacetate (S2-2),
4-allyloxybutyl 5-chloro-8-quinolinoxyacetate (S2-3),
1-allyloxyprop-2-yl 5-chloro-8-quinolinoxyacetate (S2-4),
ethyl 5-chloro-8-quinolinoxyacetate (S2-5),
methyl 5-chloro-8-quinolinoxyacetate (S2-6),
allyl 5-chloro-8-quinolinoxyacetate (S2-7),
2-(2-propylideneiminoxy)-1-ethyl 5-chloro-8-quinolinoxyacetate (S2-8), 2-oxoprop-1-yl 5-chloro-8-quinolinoxyacetate (S2-9) and related compounds as described in EP-A-86 750, EP-A-94 349 and EP-A-191 736 or EP-A-0 492 366, and also their hydrates and salts as described in WO-A-2002/034048.

b) compounds of the (5-chloro-8-quinolinoxy)malonic acid type, preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

C) Compounds of the formula (S-III)

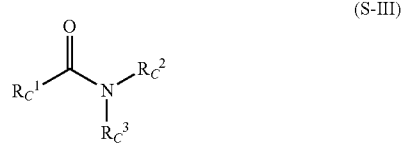

(S-III)

where the symbols and indices have the following meanings:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the dichloroacetamide type which are frequently used as pre-emergence safeners (soil-active safeners), such as, for example, "dichlormid" (see Pestic.Man.) (=N,N-diallyl-2,2-dichloroacetamide), "R-29148" (=3-dichloroacetyl-2,2,5-trimethyl-1,3-oxazolidine from Stauffer), "R-28725" (=3-dichloroacetyl-2,2,-dimethyl-1,3-oxazolidine from Stauffer), "benoxacor" (see Pestic. Man.) (=4-dichloroacetyl-3,4-dihydro-3-methyl-2H-1,4-benzoxazine), "PPG-1292" (=N-allyl-N-[(1,3-dioxolan-2-yl)methyl] dichloroacetamide from PPG Industries), "DKA-24" (=N-allyl-N-[(allylaminocarbonyl)methyl] dichloroacetamide from Sagro-Chem), "AD-67" or "MON 4660" (=3-dichloroacetyl-1-oxa-3-azaspiro[4,5]decane from Nitrokemia or Monsanto), "TI-35" (=1-dichloroacetylazepane from TRI-Chemical RT)

"diclonon" (dicyclonon) or "BAS145138" or "LAB145138" (=3-dichloroacetyl-2,5,5-trimethyl-1,3-diazabicyclo[4.3.0]nonane from BASF) and "furilazole" or "MON 13900" (see Pestic. Man.) (=(RS)-3-dichloroacetyl-5-(2-furyl)-2,2-dimethyloxazolidine).

D) N-Acylsulphonamides of the formula (S-IV) and their salts

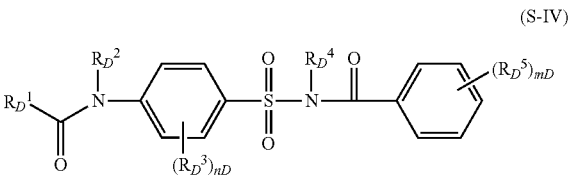

(S-IV)

in which $R_D^1$ is hydrogen, a hydrocarbon radical, a hydrocarbonoxy radical, a hydrocarbonthio radical or a heterocyclyl radical which is preferably attached via a carbon atom, where each of the 4 last-mentioned radicals is unsubstituted or substituted by one or more identical or different radicals from the group consisting of halogen, cyano, nitro, amino, hydroxyl, carboxyl, formyl, carboxamide, sulphonamide and radicals of the formula $-Z^a-R^a$, where each hydrocarbon moiety has preferably 1 to 20 carbon atoms and a carbon-containing radical $R_D^1$ including substituents has preferably 1 to 30 carbon atoms;

$R_D^2$ is hydrogen or $(C_1-C_4)$-alkyl, preferably hydrogen, or $R_D^1$ and $R_D^2$ together with the group of the formula $-CO-N-$ are the radical of a 3- to 8-membered saturated or unsaturated ring;

$R_D^3$ are identical or different and are halogen, cyano, nitro, amino, hydroxyl, carboxyl, formyl, $CONH_2$, $SO_2NH_2$ or a radical of the formula $-Z^b-R^b$;

$R_D^4$ is hydrogen or $(C_1-C_4)$-alkyl, preferably H;

$R_D^5$ are identical or different and are halogen, cyano, nitro, amino, hydroxyl, carboxyl, CHO, $CONH_2$, $SO_2NH_2$ or a radical of the formula $-Z^c-R^c$;

$R^a$ is a hydrocarbon radical or a heterocyclyl radical, where each of the two last-mentioned radicals is unsubstituted or substituted by one or more identical or different radicals from the group consisting of halogen, cyano, nitro, amino, hydroxyl, mono- and di-$[(C_1-C_4)$-alkyl]amino, or an alkyl radical in which a plurality, preferably 2 or 3, of non-adjacent $CH_2$ groups are in each case replaced by an oxygen atom;

$R^b,R^c$ are identical or different and are a hydrocarbon radical or a heterocyclyl radical, where each of the two last-mentioned radicals is unsubstituted or substituted by one or more identical or different radicals from the group consisting of halogen, cyano, nitro, amino, hydroxyl, phosphoryl, halo-$(C_1$-$C_4)$-alkoxy, mono- and di-$[(C_1$-$C_4)$-alkyl]amino, or an alkyl radical in which a plurality, preferably 2 or 3, of non-adjacent $CH_2$ groups are in each case replaced by an oxygen atom;

$Z^a$ is a divalent group of the formula —O—, —S—, —CO—, —CS—, —CO—O—, —CO—S—, —O—CO—, —S—CO—, —SO—, —SO$_2$—, —NR*—, —CO—NR*—, —NR*—CO—, —SO$_2$—NR*— or —NR*—SO$_2$—, where the bond indicated on the right-hand side of the divalent group in question is the bond to the radical $R^a$ and where the R* in the 5 last-mentioned radicals independently of one another are each H, $(C_1$-$C_4)$-alkyl or halo-$(C_1$-$C_4)$-alkyl;

$Z^b,Z^c$ are independently of one another a direct bond or a divalent group of the formula —O—, —S—, —CO—, —CS—, —CO—O—, —CO—S—, —O—CO—, —S—CO—, —SO—, —SO$_2$—, —NR*—, —SO$_2$—NR*—, —NR*—SO$_2$—, —CO—NR*— or —NR*—CO—, where the bond indicated at the right-hand side of the divalent group in question is the bond to the radical $R^b$ or $R^c$ and where the R* in the 5 last-mentioned radicals independently of one another are each H, $(C_1$-$C_4)$-alkyl or halo-$(C_1$-$C_4)$-alkyl;

$n_D$ is an integer from 0 to 4, preferably 0, 1 or 2, particularly preferably 0 or 1, and $m_D$ is an integer from 0 to 5, preferably 0, 1, 2 or 3, in particular 0, 1 or 2;

E) acylsulphamoylbenzamides of the general formula (S-V), if appropriate also in salt form,

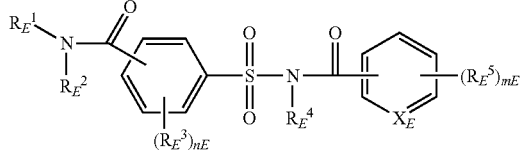

(S-V)

in which $X_E$ is CH or N;

$R_E^1$ is hydrogen, heterocyclyl or a hydrocarbon radical, where the two last-mentioned radicals are optionally substituted by one or more identical or different radicals from the group consisting of halogen, cyano, nitro, amino, hydroxyl, carboxyl, CHO, CONH$_2$, SO$_2$NH$_2$ and $Z^a$—$R^a$;

$R_E^2$ is hydrogen, hydroxyl, $(C_1$-$C_6)$-alkyl, $(C_2$-$C_6)$-alkenyl, $(C_2$-$C_6)$-alkynyl, $(C_1$-$C_6)$-alkoxy, $(C_2$-$C_6)$-alkenyloxy, where the five last-mentioned radicals are optionally substituted by one or more identical or different radicals from the group consisting of halogen, hydroxyl, $(C_1$-$C_4)$-alkyl, $(C_1$-$C_4)$-alkoxy and $(C_1$-$C_4)$-alkylthio, or $R_E^1$ and $R_E^2$ together with the nitrogen atom that carries them are a 3- to 8-membered saturated or unsaturated ring;

$R_E^3$ is halogen, cyano, nitro, amino, hydroxyl, carboxyl, CHO, CONH$_2$, SO$_2$NH$_2$ or $Z^b$—$R^b$;

$R_E^4$ is hydrogen, $(C_1$-$C_4)$-alkyl, $(C_2$-$C_4)$-alkenyl or $(C_2$-$C_4)$-alkynyl;

$R_E^5$ is halogen, cyano, nitro, amino, hydroxyl, carboxyl, phosphoryl, CHO, CONH$_2$, SO$_2$NH$_2$ or $Z^c$—$R^c$;

$R^a$ is a $(C_2$-$C_{20})$-alkyl radical whose carbon chain is interrupted once or more than once by oxygen atoms, is heterocyclyl or a hydrocarbon radical, where the two last-mentioned radicals are optionally substituted by one or more identical or different radicals from the group consisting of halogen, cyano, nitro, amino, hydroxyl, mono- and di-$[(C_1$-$C_4)$-alkyl]amino;

$R^b$, $R^C$ are identical or different and are a $(C_2$-$C_{20})$-alkyl radical whose carbon chain is interrupted once or more than once by oxygen atoms, are heterocyclyl or a hydrocarbon radical, where the two last-mentioned radicals are optionally substituted by one or more identical or different radicals from the group consisting of halogen, cyano, nitro, amino, hydroxyl, phosphoryl, $(C_1$-$C_4)$-haloalkoxy, mono- and di-$[(C_1$-$C_4)$-alkyl]amino;

$Z^a$ is a divalent unit from the group consisting of O, S, CO, CS, C(O)O, C(O)S, SO, SO$_2$, NR$^d$, C(O)NR$^d$ and SO$_2$NR$^d$;

$Z^b$, $Z^c$ are identical or different and are a direct bond or divalent unit from the group consisting of O, S, CO, CS, C(O)O, C(O)S, SO, SO$_2$, NR$^d$, SO$_2$NR$^d$ and C(O)NR$^d$;

$R^d$ is hydrogen, $(C_1$-$C_4)$-alkyl or $(C_1$-$C_4)$-haloalkyl;

$n_E$ is an integer from 0 to 4, and $m_E$ if X is CH, is an integer from 0 to 5, and, if X is N, is an integer from 0 to 4;

from among these, preference is given to compounds (also in the form of their salts) of the type of the acylsulphamoylbenzamides, for example of the formula (S-VI) below, which are known, for example, from WO 99/16744,

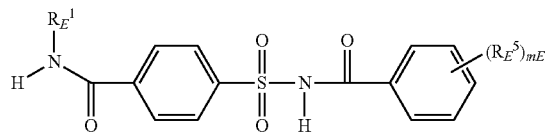

(S-VI)

for example those in which $R_E^1$=cyclopropyl and $R_E^5$=2-OMe ("cyprosulphamide", S3-1), $R_E^1$=cyclopropyl and $R_E^5$=5-Cl-2-OMe (S3-2), $R_E^1$=ethyl and $R_E^5$=2-OMe (S3-3), $R_E^1$=isopropyl and $R_E^5$=5-Cl-2-OMe (S3-4) and $R_E^1$=isopropyl and $R_E^5$=2-OMe (S3-5);

F) compounds of the type of the N-acylsulphamoylphenylureas of the formula (S-VII), which are known, for example, from EP-A-365484

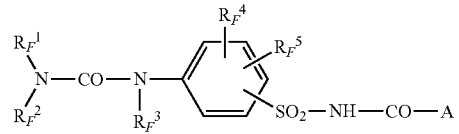

(S-VII)

in which

A is a radical from the group consisting of

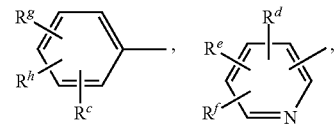

-continued

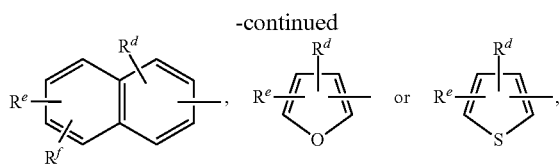

$R_F^1$ and $R_F^2$ independently of one another are hydrogen, $(C_1-C_8)$-alkyl, $(C_3-C_8)$-cycloalkyl, $(C_3-C_6)$-alkenyl, $(C_3-C_6)$-alkynyl,

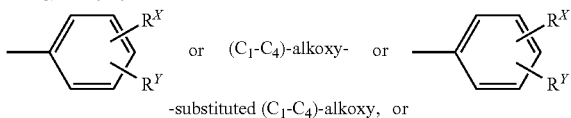

-substituted $(C_1-C_4)$-alkoxy, or $R_F^1$ and $R_F^2$ together are a $(C_4-C_6)$-alkylene bridge or a $(C_4-C_6)$-alkylene bridge interrupted by oxygen, sulphur, SO, $SO_2$, NH or $-N(C_1-C_4$-alkyl)-,
$R_F^3$ is hydrogen or $(C_1-C_4)$-alkyl,
$R_F^4$ and $R_F^5$ independently of one another are hydrogen, halogen, cyano, nitro, trifluoromethyl, $C_1-C_4$-alkyl, $C_1-C_4$-alkoxy, $C_1-C_4$-alkylthio, $C_1-C_4$-alkylsulphinyl, $C_1-C_4$-alkylsulphonyl, $-COOR^j$, $-CONR^kR^m$, $-COW$, $-SO_2NR^kR^m$ or $-OSO_2-C_1-C_4$-alkyl, or W and $R^b$ together are a $(C_3-C_4)$-alkylene bridge which may be substituted by halogen or $C_1-C_4$-alkyl, or a $(C_3-C_4)$-alkenylene bridge which may be substituted by halogen or $(C_1-C_4)$-alkyl, or a $C_4$-alkadienylene bridge which may be substituted by halogen or $(C_1-C_4)$-alkyl, and
$R^g$ and $R^h$ independently of one another are hydrogen, halogen, $C_1-C_4$-alkyl, trifluoromethyl, methoxy, methylthio or $-COOR^j$, where
$R^c$ is hydrogen, halogen, $(C_1-C_4)$-alkyl or methoxy,
$R^d$ is hydrogen, halogen, nitro, $(C_1-C_4)$-alkyl, $(C_1-C_4)$-alkoxy, $(C_1-C_4)$-alkylthio, $(C_1-C_4)$-alkylsulphinyl, $(C_1-C_4)$-alkylsulphonyl, $-COOR^j$ or $-CONR^kR^m$,
$R^e$ is hydrogen, halogen, $C_1-C_4$-alkyl, $-COOR^j$, trifluoromethyl or methoxy, or $R^d$ and $R^e$ together are a $(C_3-C_4)$-alkylene bridge,
$R^f$ is hydrogen, halogen or $(C_1-C_4)$-alkyl,
$R^X$ and $R^Y$ independently of one another are hydrogen, halogen, $(C_1-C_4)$-alkyl, $(C_1-C_4)$-alkoxy, $(C_1-C_4)$-alkylthio, $-COOR^4$, trifluoromethyl, nitro or cyano,
$R^j$, $R^k$ and $R^m$ independently of one another are hydrogen or $(C_1-C_4)$-alkyl,
$R^k$ and $R^m$ together are a $(C_4-C_6)$-alkylene bridge and a $(C_4-C_6)$-alkylene bridge interrupted by oxygen, NH or $-N(C_1-C_4$-alkyl)-, and
$R^n$ is $(C_1-C_4)$-alkyl, phenyl or phenyl substituted by halogen, $(C_1-C_4)$-alkyl, methoxy, nitro or trifluoromethyl,
from among these, preference is given to:
1-[4-(N-2-methoxybenzoylsulphamoyl)phenyl]-3-methylurea,
1-[4-(N-2-methoxybenzoylsulphamoyl)phenyl]-3,3-dimethylurea,
1-[4-(N-4,5-dimethylbenzoylsulphamoyl)phenyl]-3-methylurea,
1-[4-(N-naphthoylsulphamoyl)phenyl]-3,3-dimethylurea, including the stereoisomers and agriculturally customary salts,
G) active compounds from the class of the hydroxyaromatics and aromatic-aliphatic carboxylic acid derivatives, for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 1,2-dihydro-2-oxo-6-trifluoromethylpyridine-3-carboxamide, 2-hydroxycinnamic acid, 2,4-dichlorocinnamic acid, as described in WO 2004/084631, WO 2005/015994, WO 2006/007981, WO 2005/016001;

H) active compounds from the class of the 1,2-dihydroquinoxalin-2-ones, for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulphonylaminoethyl)-3-(2-thienyl)-1,2-dihydroquinoxalin-2-one, as described in WO 2005/112630, I) active compounds which, in addition to a herbicidal action against harmful plants also have safener action on crop plants such as rice, such as, for example, "dimepiperate" or "MY-93" (see Pestic. Man.) (=S-1-methyl-1-phenylethyl piperidine-1-thiocarboxylate), which is known as safener for rice against damage caused by the herbicide molinate, "daimuron" or "SK 23" (see Pestic. Man.) (=1-(1-methyl-1-phenylethyl)-3-p-tolylurea), which is known as safener for rice against imazosulfuron herbicide damage, "cumyluron"="JC-940" (3-(2-chlorophenylmethyl)-1-(1-methyl-1-phenylethyl)urea, see JP-A-60087254), which is known as a safener for rice against damage by some herbicides, "methoxyphenone" or "NK 049" (=3,3'-dimethyl-4-methoxybenzophenone), which is known as safener for rice against damage by some herbicides, "CSB" (1-bromo-4-(chloromethylsulphonyl)benzene) (CAS Reg. No. 54091-06-4 from Kumiai), which is known as safener for rice against damage by some herbicides, K) compounds of the formula (S-IX), as described in WO-A-1998/38856, (S-IX)

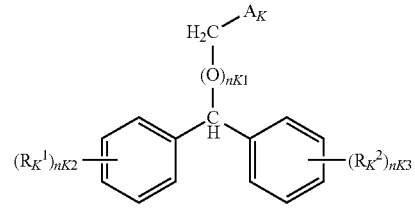

where the symbols and indices have the following meanings:
$R_K^1$, $R_K^2$ independently of one another are halogen, $(C_1-C_4)$-alkyl, $(C_1-C_4)$-alkoxy, $(C_1-C_4)$-haloalkyl, $(C_1-C_4)$-alkylamino, di$(C_1-C_4)$-alkylamino, nitro;
$A_K$ is $COOR_K^3$ or $COOR_K^4$
$R_K^3$, $R_K^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl and alkylammonium,
$n_K^1$ is 0 or 1 and
$n_K^2$, $n_K^3$ independently of one another are 0, 1 or 2;
preferably:
methyl (diphenylmethoxy)acetate (CAS reg no: 41858-19-9),
L) compounds of the formula (S-X) as described in WO A-98/27049

(S-X)

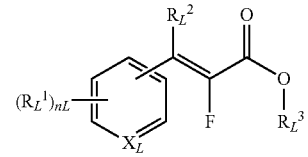

where the symbols and indices have the following meanings:

$X_L$ is CH or N,
$n_L$ if X=N, is an integer from 0 to 4 and
in the case that X=CH, an integer from 0 to 5,
$R_L^1$ halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulphonyl, $(C_1-C_4)$-alkoxycarbonyl, optionally substituted phenyl, optionally substituted phenoxy,
$R_L^2$ is hydrogen or $(C_1-C_4)$-alkyl
$R_L^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more, preferably up to three identical or different radicals from the group consisting of halogen and alkoxy; or salts thereof.
M) active compounds from the class of the 3-(5-tetrazolylcarbonyl)-2-quinolones, for example
1,2-dihydro-4-hydroxy-1-ethyl-3-(5-tetrazolylcarbonyl)-2-quinolone (CAS Reg. No. 219479-18-2), 1,2-dihydro-4-hydroxy-1-methyl-3-(5-tetrazolylcarbonyl)-2-quinolone (CAS Reg. No.: 95855-00-8), as described in WO-A-1999000020,
N) compounds of the formula (S-XI) or (S-XII)
as described in WO-A-2007023719 and WO-A-2007023764

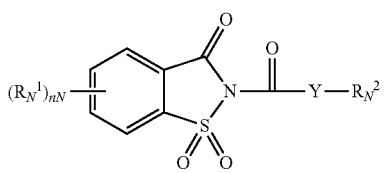

(S-XI)

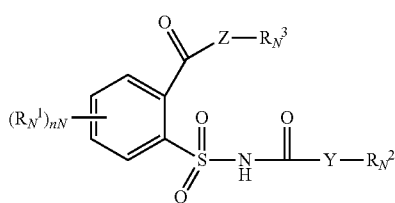

(S-XII)

in which
$R_N^1$ is halogen, $(C_1-C_4)$-alkyl, methoxy, nitro, cyano, $CF_3$, $OCF_3$,
Y, Z independently of one another are O or S,
$n_N$ is an integer from 0 to 4,
$R_N^2$ is $(C_1-C_{16})$-alkyl, $(C_2-C_6)$-alkenyl, $(C_3-C_6)$-cycloalkyl, aryl; benzyl, halobenzyl,
$R_N^3$ is hydrogen, $(C_1-C_6)$-alkyl;
O) one or more compounds from the group consisting of:
1,8-naphthalic anhydride,
O,O-diethyl S-2-ethylthioethyl phosphorodithioate (disulfoton),
4-chlorophenyl methylcarbamate (mephenate),
O,O-diethyl O-phenyl phosphorothioate (dietholate),
4-carboxy-3,4-dihydro-2H-1-benzopyran-4-acetic acid (CL-304415, CAS Reg. No.: 31541-57-8),
2-propenyl 1-oxa-4-azaspiro[4.5]decane-4-carbodithioate (MG-838, CAS Reg. No.: 133993-74-5),
methyl [(3-oxo-1H-2-benzothiopyran-4(3H)-ylidene)methoxy]acetate (from WO-A-98/13361; CAS Reg. No.: 205121-04-6),
cyanomethoxyimino(phenyl)acetonitrile (cyometrinil)
1,3-dioxolan-2-ylmethoxyimino(phenyl)acetonitrile (oxabetrinil),
4'-chloro-2,2,2-trifluoroacetophenone 0-1,3-dioxolan-2-ylmethyloxime (fluxofenim),
4,6-dichloro-2-phenylpyrimidine (fenclorim),
benzyl 2-chloro-4-trifluoromethyl-1,3-thiazole-5-carboxylate (flurazole),
2-dichloromethyl-2-methyl-1,3-dioxolane (MG-191),
including the stereoisomers, and the salts customary in agriculture.

The weight ratios of herbicide (mixture) to safener depend generally on the herbicide application rate and the efficacy of the safener in question and may vary within wide limits, for example in the range from 200:1 to 1:200, preferably 100:1 to 1:100, in particular 20:1 to 1:20. Analogously to the compounds (I) or mixtures thereof, the safeners can be formulated with further herbicides/pesticides and be provided and employed as a finished formulation or tank mix with the herbicides.

For application, the herbicide or herbicide/safener formulations present in commercial form are, if appropriate, diluted in a customary manner, for example in the case of wettable powders, emulsifiable concentrates, dispersions and water-dispersible granules with water. Preparations in the form of dusts, granules for soil application or granules for sowing and sprayable solutions are usually not diluted further with other inert substances prior to application.

The application rate of the compounds of the formula (I) and/or their salts is affected to a certain extent by external conditions such as temperature, humidity, etc. Here, the application rate may vary within wide limits. For the application as a herbicide for controlling harmful plants, the total amount of compounds of the formula (I) and their salts is preferably in the range from 0.001 to 10.0 kg/ha, with preference in the range from 0.005 to 5 kg/ha, more preferably in the range from 0.01 to 1.5 kg/ha, in particular in the range from 0.05 to 1 kg/ha. This applies both to application by the pre-emergence method and the post-emergence method, the pre-emergence treatment being preferred by virtue of the significantly higher activity.

When the compounds of the formula (I) and/or their salts are used as plant growth regulator, for example as culm stabilizer for crop plants like those mentioned above, preferably cereal plants, such as wheat, barley, rye, triticale, millet, rice or maize, the total application rate is preferably in the range of from 0.001 to 2 kg/ha, preferably in the range of from 0.005 to 1 kg/ha, in particular in the range of from 10 to 500 g/ha, very particularly in the range from 20 to 250 g/ha. This applies both to the pre-emergence and the post-emergence application.

The application as culm stabilizer may take place at various stages of the growth of the plants. Preferred is, for example, the application after the tillering phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests.

The symbols ">" and "<" mean "greater than" and "smaller than", respectively. The symbol "≥" means "greater than or equal to", the symbol "≤" means "smaller than or equal to".

If, in the context of the description and the examples, the designations "R" and "S" are stated for the absolute configuration at a centre of chirality of the stereoisomers of the formulae (I), (Ia) and (Ib), this follows the RS nomenclature of the Cahn-Ingold-Prelog rules.

Abbreviations and designations used:
Ex.=Example number
H=hydrogen (atom)
Me=methyl Et=ethyl
n-Pr=n-propyl
i-Pr=isopropyl
n-Bu=n-butyl
i-Bu=isobutyl
F, Cl, Br, I=fluorine, chlorine, bromine and iodine, respectively, in accordance with the conventional chemical atom symbols
MeO or OMe=methoxy
CN=cyano
$NO_2$=nitro The position of a substituent at the phenyl ring, for example in position 2, is stated as a prefix to the symbol or the abbreviation of the radical, for example
2-Cl=2-chloro
2-Me=2-methyl Numerations of the substituent positions for di- or trisubstituted substitution patterns are analogously stated as a prefix, for example
3,5-$Me_2$=3,5-dimethyl (e.g. as substitution at the phenyl ring)
2,3-$Cl_2$=2,3-dichloro (e.g. as substitution at the phenyl ring)
3,4-$F_2$=3,4-difluoro (e.g. as substitution at the phenyl ring)

Other abbreviations are to be understood analogously to the examples stated above.
"$(R^2)_n$="H" unsubstituted cycle (n=0)
"$(R^3)_m$="H" unsubstituted cycle (m=0)

In addition, the customary chemical symbols and formulae apply, such as, for example, $CH_2$ for methylene or $CF_3$ for trifluoromethyl or OH for hydroxyl. Correspondingly, composite meanings are defined as composed of the abbreviations mentioned.

In an exemplary manner, some synthesis examples of compounds of the formula (I) are described below. In the examples, the amounts (including the percentages) refer to the weight, unless stated otherwise.

SYNTHESIS EXAMPLES

1a) Preparation of methyl 4-cyano-3-(2,6-difluorophenyl)-4-phenylbutanoate

Under protective gas (argon), 192 mg (1.70 mmol) of potassium tert-butoxide were added to 1.692 g (8.53 mmol) of methyl 3-(2,6-difluorophenyl)acrylate and 1.0 g (8.53 mmol) of phenylacetonitrile in 15.0 ml of toluene, and the mixture was stirred at 100° C. for 48 h. After removal of the solvent under reduced pressure, the residue was taken up in ethyl acetate and washed twice with in each case 50 ml of water. The combined organic phases were dried over sodium sulphate and the solvent was removed under reduced pressure. Chromatography of the residue on silica gel (ethyl acetate/heptane=15:85) gave 1.501 g (56% of theory) of the diastereomeric methyl 4-cyano-3-(2,6-difluorophenyl)-4-phenylbutanoate (erythro:threo=29:71, comparison of the triplets in the $^1$H-NMR in $CDCl_3$ at 6.92 and 6.73 ppm).

1b) Preparation of 3-(2,6-difluorophenyl)-5-hydroxy-2-phenylpentanonitrile

Under protective gas (argon), 1.5 g (4.75 mmol) of methyl 4-cyano-3-(2,6-difluorophenyl)-4-phenylbutanoate in 30 ml THF were added to 0.257 g (4.75 mmol) of potassium borohydride and 0.202 g (4.75 mmol) of lithium chloride in 20 ml of THF, and the mixture was stirred at 70° C. for 5 h. After cooling to 0° C., the mixture was acidified with hydrochloric acid. The residue obtained was then taken up in ethyl acetate and washed twice with in each case 50 ml of water. The combined organic phases were dried over sodium sulphate and the solvent was removed under reduced pressure. Chromatography of the residue on silica gel (ethyl acetate/heptane=15:85) gave 0.900 g (65% of theory) of the diastereomeric 3-(2,6-difluorophenyl)-5-hydroxy-2-phenylpentanonitrile (erythro:threo=44:56, comparison of the triplets in the $^1$H-NMR in $CDCl_3$ at 6.94 and 6.71 ppm).

1c) Preparation of (2R,3R)-3-(2,6-difluorophenyl)-5-hydroxy-2-phenylpentanonitrile Preparative chromatography [(80 ml/min n-heptane/2-propanol (80:20)] of 100 mg of the diastereomer mixture obtained according to a) above (dissolved in 4.0 ml of methanol) on a chiral solid phase [Chiralpak IC, 20 (250× 50) mm column] gave 19 mg of (2R,3R)-3-(2,6-difluorophenyl)-5-hydroxy-2-phenylpentanonitrile which eluted as the last but one of the four stereoisomers (retention time: 10.3 min) The absolute configuration was then assigned by X-ray structural analysis.

1b) Preparation of 4-cyano-3-(2,6-difluorophenyl)-4-phenylbutyl acetate

Under protective gas (Ar), 78 mg (1.00 mmol) of acetyl chloride were added to 144 mg (0.50 mmol) of 3-(2,6-difluorophenyl)-5-hydroxy-2-phenylpentanonitrile, 7 mg (0.05 mmol) of 4-(dimethylamino)pyridine and 100 mg (1.00 mmol) of triethylamine in 10 ml of dichloromethane, and the mixture was stirred at 25° C. for 3 h. The residue was taken up in ethyl acetate and washed twice with in each case 50 ml of water. The combined organic phases were then dried over sodium sulphate and the solvent was removed under reduced pressure. Chromatography of the residue on silica gel (ethyl acetate/heptane=15:85) gave 127 mg (78% of theory) of the diastereomeric 4-cyano-3-(2,6-difluorophenyl)-4-phenylbutyl acetate (erythro:threo=48:52, comparison of the triplets in the $^1$H-NMR in $CDCl_3$ at 6.71 and 6.94 ppm).

1c) Preparation of (2R,3R)-4-cyano-3-(2,6-difluorophenyl)-4-phenylbutyl acetate Under protective gas (Ar), 109 mg (1.39 mmol) of acetyl chloride were added to 200 mg (0.69 mmol) of (2R,3R)-3-(2,6-difluorophenyl)-5-hydroxy-2-phenylpentanonitrile, 9 mg (0.07 mmol) of 4-(dimethylamino)pyridine and 141 mg (1.39 mmol) of triethylamine in 10 ml of dichloromethane, and the mixture was stirred at 25° C. for 3 h. The residue was taken up in ethyl acetate and washed twice with in each case 50 ml of water. The combined organic phases were dried over sodium sulphate and the solvent was removed under reduced pressure. Chromatography of the residue on silica gel (ethyl acetate/heptane=15:85) gave 169 mg (74% of theory) of (2R,3R)-4-cyano-3-(2,6-difluorophenyl)-4-phenylbutyl acetate.

Definition and Description of Preferred Compounds According to the Invention—Analytical and Physical Data Information regarding the examples given in Tables 2 to 2f below:

For reference purposes, specific numbers (=Example Numbers) have been assigned to the corresponding individual compounds in Tables 2 to 2f below, where the Example Number in question is composed of the number of the chemical formula "(Formula Number)" assigned to the respective table followed by a row number "(Row Number)" which refers to the same number as stated in the row of the first column of Table 1. A compound or the chemical structure of Example No. "(formula number)(row number)" is thus defined unambiguously by the formula above the respective table by the formula number and row number of Table 1, which is to be illustrated using the following examples:

The example of No. "Iba1" from Table 2 is the compound of the formula (Ib) in which $R^1$=H (=hydrogen) [=formula (Iba)] and $(R^2)_n$=H (=hydrogen) and $(R^3)_m$=2,6-$F_2$, defined according to entry number 1 of Table 1.

The example of No. "Ibd1080" from Table 2 is the compound of the formula (Ib) in which $R^1$=butanoyl [=formula (Ibd)] and $(R^2)_n$=3,4-$Cl_2$ and $(R^3)_m$=4-OMe, defined according to entry number 1080 of Table 1.

This applies correspondingly to the assignment of racemic or optically active threo stereoisomers or erythro stereoisomers. For example, for reference purposes, specific numbers (=Example Numbers) have been assigned to the compounds of Table 2a, where the number "threo-Iba(row number)" refers to the racemic mixture of the threo enantiomers having the chemical structure of the formulae (threo-1-Iba) and (threo-2-Iba), each of which has the structural combination of groups $(R^2)_n$ and $(R^3)_m$ according to the row number of Table 1.

Table 2: Compounds of the formulae (Ib), (Iba), (Ibb), (Ibc), (Ibd), (Ibe), (Ibf), (Ibg) (Ibh), (Ibi), (Ibj), (Ibk), (Ibl), (Ibm), (Ibn), (Ibo), (Ibp), (Ibq), (Ibr) (Ibs), (Ibt), (Ibu), (Ibv), (Ibw), (Ibx), (Iby), (Ibz), (Ibaa), (Ibab), (Ibac), (Ibad), (Ibae), (Ibaf), (Ibag) and (Ibah) where $(R^2)_n$ and $(R^3)_m$ are each as defined in Table 1.

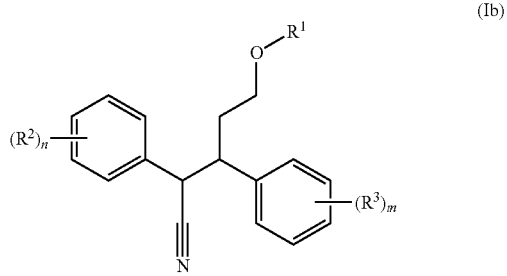

(Ib)

Definitions of preferred compounds of the formula (Ib) are shown in Table U1 below.

TABLE U1

| Formula | Radical $R^1$ in Formula (Ib) |
|---|---|
| (Iba) | H (hydrogen) |
| (Ibb) | acetyl |
| (Ibc) | propanoyl |
| (Ibd) | butanoyl |
| (Ibe) | 2-methylpropanoyl (= isopropanoyl) |
| (Ibf) | 2,2-difluoroacetyl |
| (Ibg) | 2,2,2-trifluoroacetyl |
| (Ibh) | C(O)OMe |
| (Ibi) | cyclopropanecarbonyl |
| (Ibj) | 1-methylcyclopropanecarbonyl |
| (Ibk) | acryl |
| (Ibl) | prop-2-ynoyl |
| (Ibm) | but-2-ynoyl |

TABLE U1-continued

| Formula | Radical $R^1$ in Formula (Ib) |
|---|---|
| (Ibn) | 2-methylacryl |
| (Ibo) | benzoyl |
| (Ibp) | 4chlorobenzoyl |
| (Ibq) | 3-chlorobenzoyl |
| (Ibr) | 2-chlorobenzoyl |
| (Ibs) | 4-fluorobenzoyl |
| (Ibt) | 3-fluorobenzoyl |
| (Ibu) | 2-fluorobenzoyl |
| (Ibv) | 2,2-dimethylpropanoyl (= pivaloyl) |
| (Ibw) | 3,3-dimethylbutanoyl |
| (Ibx) | pentanoyl |
| (Iby) | hexanoyl |
| (Ibz) | 2-nitrobenzoyl |
| (Ibaa) | 2-fluoroacetyl |
| (Ibab) | 2-chloroacetyl |
| (Ibac) | 2-bromoacetyl |
| (Ibad) | 2,2-dichloroacetyl |
| (Ibae) | 2-methoxyacetyl |
| (Ibaf) | 2,6-difluorobenzoyl |
| (Ibag) | C(O)C(O)OMe |
| (Ibah) | C(O)CH$_2$C(O)OMe |

Erythro/Threo Mixtures of the Formulae (Iba) to (Ibah):

Examples of compounds of the formulae (Iba) to (Ibah) are the compounds of the respective formulae (Iba) to (Ibah), in each case in the form of a racemic erythro/threo mixture (ratio 70:30 to 30:70), where the structural combination of the groups $(R^2)_n$ and $(R^3)_m$ is defined according to a row number of Table 1.

The numeration is carried out according to "(formula) (row number)" without any brackets, for example Iba200=compound of the formula (Iba) having the structural combination of row 200 of Table 1.

For Tables 2a, 2b and 2c Below:

Threo, threo-1 and threo-2 compounds of the compounds of the formulae (Ib), (Iba), (Ibb), (Ibc), (Ibd), (Ibe), (Ibf), (Ibg) (Ibh), (Ibi), (Ibj), (Ibk), (Ibl), (Ibm), (Ibn), (Ibo), (Ibp), (Ibq), (Ibr) (Ibs), (Ibt), (Ibu), (Ibv), (Ibw), (Ibx), (Iby), (Ibz), (Ibaa), (Ibab), (Ibac), (Ibad), (Ibae), (Ibaf), (Ibag) and (Ibah) where $(R^2)_n$ and $(R^3)_m$ are each as defined in Table 1.

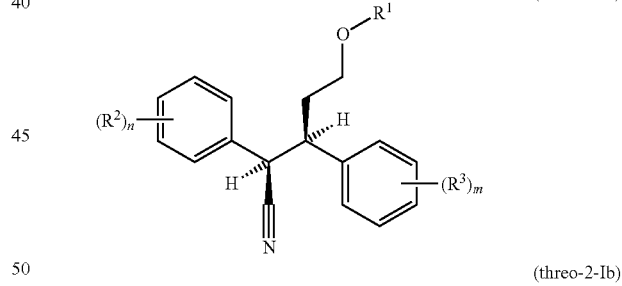

(threo-1-Ib)

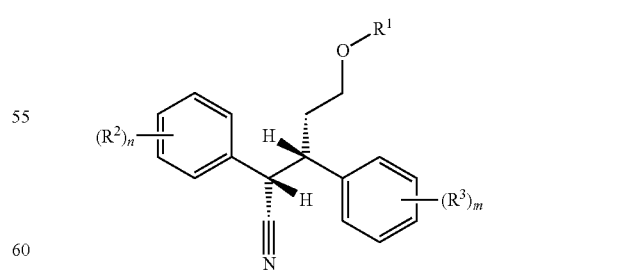

(threo-2-Ib)

(threo-Ib)=(threo-1-Ib)+(threo-2-Ib)(50:50)=(rac.)

Definitions of preferred compounds of the formulae (threo-Ib), (threo-1-Ib) and (threo-2-Ib) are shown in Table U2 below.

TABLE U2

| Formula | Radical R$^1$ in Formula (threo-Ib) |
|---|---|
| (threo-Iba) | H (hydrogen) |
| (threo-1-Iba) | H (hydrogen) |
| (threo-2-Iba) | H (hydrogen) |
| (threo-Ibb) | acetyl |
| (threo-1-Ibb) | acetyl |
| (threo-2-Ibb) | acetyl |
| (threo-Ibc) | propanoyl |
| (threo-1-Ibc) | propanoyl |
| (threo-2-Ibc) | propanoyl |
| (threo-Ibd) | butanoyl |
| (threo-1-Ibd) | butanoyl |
| (threo-2-Ibd) | butanoyl |
| (threo-Ibe) | 2-methylpropanoyl (= isopropanoyl) |
| (threo-1-Ibe) | 2-methylpropanoyl (= isopropanoyl) |
| (threo-2-Ibe) | 2-methylpropanoyl (= isopropanoyl) |
| (threo-Ibf) | 2,2-difluoroacetyl |
| (threo-1-Ibf) | 2,2-difluoroacetyl |
| (threo-2-Ibf) | 2,2-difluoroacetyl |
| (threo-Ibg) | 2,2,2-trifluoroacetyl |
| (threo-1-Ibg) | 2,2,2-trifluoroacetyl |
| (threo-2-Ibg) | 2,2,2-trifluoroacetyl |
| (threo-Ibh) | C(O)OMe |
| (threo-1-Ibh) | C(O)OMe |
| (threo-2-Ibh) | C(O)OMe |
| (threo-Ibi) | cyclopropanecarbonyl |
| (threo-1-Ibi) | cyclopropanecarbonyl |
| (threo-2-Ibi) | cyclopropanecarbonyl |
| (threo-Ibj) | 1-methylcyclopropanecarbonyl |
| (threo-1-Ibj) | 1-methylcyclopropanecarbonyl |
| (threo-2-Ibj) | 1-methylcyclopropanecarbonyl |
| (threo-Ibk) | acryl |
| (threo-1-Ibk) | acryl |
| (threo-2-Ibk) | acryl |
| (threo-Ibl) | prop-2-ynoyl |
| (threo-1-Ibl) | prop-2-ynoyl |
| (threo-2-Ibl) | prop-2-ynoyl |
| (threo-Ibm) | but-2-ynoyl |
| (threo-1-Ibm) | but-2-ynoyl |
| (threo-2-Ibm) | but-2-ynoyl |
| (threo-Ibn) | 2-methylacryl |
| (threo-1-Ibn) | 2-methylacryl |
| (threo-2-Ibn) | 2-methylacryl |
| (threo-Ibo) | benzoyl |
| (threo-1-Ibo) | benzoyl |
| (threo-2-Ibo) | benzoyl |
| (threo-Ibp) | 4-chlorobenzoyl |
| (threo-1-Ibp) | 4-chlorobenzoyl |
| (threo-2-Ibp) | 4-chlorobenzoyl |
| (threo-Ibq) | 3-chlorobenzoyl |
| (threo-1-Ibq) | 3-chlorobenzoyl |
| (threo-2-Ibq) | 3-chlorobenzoyl |
| (threo-Ibr) | 2-chlorobenzoyl |
| (threo-1-Ibr) | 2-chlorobenzoyl |
| (threo-2-Ibr) | 2-chlorobenzoyl |
| (threo-Ibs) | 4-fluorobenzoyl |
| (threo-1-Ibs) | 4-fluorobenzoyl |
| (threo-2-Ibs) | 4-fluorobenzoyl |
| (threo-Ibt) | 3-fluorobenzoyl |
| (threo-1-Ibt) | 3-fluorobenzoyl |
| (threo-2-Ibt) | 3-fluorobenzoyl |
| (threo-Ibu) | 2-fluorobenzoyl |
| (threo-1-Ibu) | 2-fluorobenzoyl |
| (threo-2-Ibu) | 2-fluorobenzoyl |
| (threo-Ibv) | 2,2-dimethylpropanoyl (= pivaloyl) |
| (threo-1-Ibv) | 2,2-dimethylpropanoyl (= pivaloyl) |
| (threo-2-Ibv) | 2,2-dimethylpropanoyl (= pivaloyl) |
| (threo-Ibw) | 3,3-dimethylbutanoyl |
| (threo-1-Ibw) | 3,3-dimethylbutanoyl |
| (threo-2-Ibw) | 3,3-dimethylbutanoyl |
| (threo-Ibx) | pentanoyl |
| (threo-1-Ibx) | pentanoyl |
| (threo-2-Ibx) | pentanoyl |
| (threo-Iby) | hexanoyl |
| (threo-1-Iby) | hexanoyl |
| (threo-2-Iby) | hexanoyl |
| (threo-Ibz) | 2-nitrobenzoyl |
| (threo-1-Ibz) | 2-nitrobenzoyl |
| (threo-2-Ibz) | 2-nitrobenzoyl |
| (threo-Ibaa) | 2-fluoroacetyl |
| (threo-1-Ibaa) | 2-fluoroacetyl |
| (threo-2-Ibaa) | 2-fluoroacetyl |
| (threo-Ibab) | 2-chloroacetyl |
| (threo-1-Ibab) | 2-chloroacetyl |
| (threo-2-Ibab) | 2-chloroacetyl |
| (threo-Ibac) | 2-bromoacetyl |
| (threo-1-Ibac) | 2-bromoacetyl |
| (threo-2-Ibac) | 2-bromoacetyl |
| (threo-Ibad) | 2,2-dichloroacetyl |
| (threo-1-Ibad) | 2,2-dichloroacetyl |
| (threo-2-Ibad) | 2,2-dichloroacetyl |
| (threo-Ibae) | 2-methoxyacetyl |
| (threo-1-Ibae) | 2-methoxyacetyl |
| (threo-2-Ibae) | 2-methoxyacetyl |
| (threo-Ibaf) | 2,6-difluorobenzoyl |
| (threo-1-Ibaf) | 2,6-difluorobenzoyl |
| (threo-2-Ibaf) | 2,6-difluorobenzoyl |
| (threo-Ibag) | C(O)C(O)OMe |
| (threo-1-Ibag) | C(O)C(O)OMe |
| (threo-2-Ibag) | C(O)C(O)OMe |
| (threo-Ibah) | C(O)CH$_2$C(O)OMe |
| (threo-1-Ibah) | C(O)CH$_2$C(O)OMe |
| (threo-2-Ibah) | C(O)CH$_2$C(O)OMe |

Table 2a: (Threo Racemates)

Examples of the compounds of the formulae (threo-Iba) to (threo-Ibah) (see Table U2) are the compounds of the formulae in question in the form of the racemic mixture of the threo isomers where the structural combination of groups (R$^2$)$_n$ and (R$^3$)$_m$ is defined according to a row number of Table 1.

The numeration is carried out according to "(formula)(row number)" without any brackets, for example threo-Iba200=compound of the formula (threo-Iba) having the structural combination of row 200 of Table 1.

Table 2b: (Optically Active Threo-2 Enantiomers)

Examples of the compounds of the formulae (threo-2-Iba) to (threo-2-Ibah) (see Table U2) are the optically active threo-2 compounds of the formulae in question in enriched form [=(2S,3S)-form having more than 80% ee] where the structural combination of groups (R$^2$)$_n$ and (R$^3$)$_m$ is defined according to a row number of Table 1.

Compounds are numbered "(formula)(row number)", without any brackets. For example, No. threo-2-Iba789 refers to the compound of the formula (threo-2-Iba) in which (R$^2$)$_n$=4-chloro and (R$^3$)$_m$=3-Cl, 5-F.

Table 2c: (Optically Active Threo-1 Enantiomers)

Examples of the compounds of the formulae (threo-1-Iba) to (threo-1-Ibah) (see Table U2) are the optically active threo-1 compounds of the formulae in question in enriched form [=(2R,3R)-form having more than 80% ee] where the structural combination of groups (R$^2$)$_n$ and (R$^3$)$_m$ is defined according to a row number of Table 1.

Compounds are numbered "(formula)(row number)", without any brackets. For example, No. threo-1-Ibb5 refers to the compound of the formula (threo-1-Ibb) in which (R$^2$)$_n$=3-chloro and (R$^3$)$_m$=2,6-F$_2$.

For Tables 2d, 2e and 2f Below:

Erythro, erythro-1 and erythro-2 compounds of the compounds of the formulae (Ib), (Iba), (Ibb), (Ibc), (Ibd), (the), (Ibf), (Ibg) (Ibh), (Ibi), (Ibj), (Ibk), (Ibl), (Ibm), (Ibn), (Ibo), (Ibp), (Ibq), (Ibr) (Ibs), (Ibt), (Ibu), (Ibv), (Ibw), (Ibx), (Iby), (Ibz), (Ibaa), (Ibab), (Ibac), (Ibad), (Ibae), (Ibaf), (Ibag) and (Ibah) where (R$^2$)$_n$ and (R$^3$)$_m$ are each as defined in Table 1.

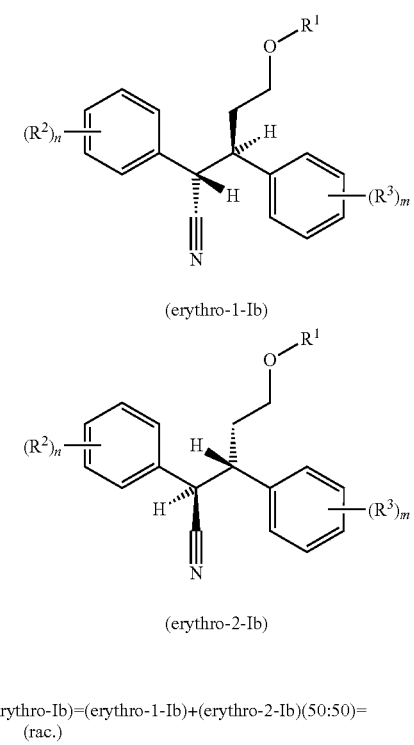

(erythro-1-Ib)

(erythro-2-Ib)

(erythro-Ib)=(erythro-1-Ib)+(erythro-2-Ib)(50:50)= (rac.)

Definitions of preferred compounds of the formulae (erythro-Ib), (erythro-1-Ib) and (erythro-2-Ib) are shown in Table U3 below.

TABLE U3

| Formula | Radical $R^1$ in Formula(erythro-Ib) |
|---|---|
| (erythro-Iba) | H (hydrogen) |
| (erythro-1-Iba) | H (hydrogen) |
| (erythro-2-Iba) | H (hydrogen) |
| (erythro-Ibb) | acetyl |
| (erythro-1-Ibb) | acetyl |
| (erythro-2-Ibb) | acetyl |
| (erythro-Ibc) | propanoyl |
| (erythro-1-Ibc) | propanoyl |
| (erythro-2-Ibc) | propanoyl |
| (erythro-Ibd) | butanoyl |
| (erythro-1-Ibd) | butanoyl |
| (erythro-2-Ibd) | butanoyl |
| (erythro-Ibe) | 2-methylpropanoyl (= isopropanoyl) |
| (erythro-1-Ibe) | 2-methylpropanoyl (= isopropanoyl) |
| (erythro-2-Ibe) | 2-methylpropanoyl (= isopropanoyl) |
| (erythro-Ibf) | 2,2-difluoroacetyl |
| (erythro-1-Ibf) | 2,2-difluoroacetyl |
| (erythro-2-Ibf) | 2,2-difluoroacetyl |
| (erythro-Ibg) | 2,2,2-trifluoroacetyl |
| (erythro-1-Ibg) | 2,2,2-trifluoroacetyl |
| (erythro-2-Ibg) | 2,2,2-trifluoroacetyl |
| (erythro-Ibh) | C(O)OMe |
| (erythro-1-Ibh) | C(O)OMe |
| (erythro-2-Ibh) | C(O)OMe |
| (erythro-Ibi) | cyclopropanecarbonyl |
| (erythro-1-Ibi) | cyclopropanecarbonyl |
| (erythro-2-Ibi) | cyclopropanecarbonyl |
| (erythro-Ibj) | 1-methylcyclopropanecarbonyl |
| (erythro-1-Ibj) | 1-methylcyclopropanecarbonyl |
| (erythro-2-Ibj) | 1-methylcyclopropanecarbonyl |
| (erythro-Ibk) | acryl |
| (erythro-1-Ibk) | acryl |
| (erythro-2-Ibk) | acryl |
| (erythro-Ibl) | prop-2-ynoyl |
| (erythro-1-Ibl) | prop-2-ynoyl |
| (erythro-2-Ibl) | prop-2-ynoyl |
| (erythro-Ibm) | but-2-ynoyl |

TABLE U3-continued

| Formula | Radical $R^1$ in Formula(erythro-Ib) |
|---|---|
| (erythro-1-Ibm) | but-2-ynoyl |
| (erythro-2-Ibm) | but-2-ynoyl |
| (erythro-Ibn) | 2-methylacryl |
| (erythro-1-Ibn) | 2-methylacryl |
| (erythro-2-Ibn) | 2-methylacryl |
| (erythro-Ibo) | benzoyl |
| (erythro-1-Ibo) | benzoyl |
| (erythro-2-Ibo) | benzoyl |
| (erythro-Ibp) | 4-chlorobenzoyl |
| (erythro-1-Ibp) | 4-chlorobenzoyl |
| (erythro-2-Ibp) | 4-chlorobenzoyl |
| (erythro-Ibq) | 3-chlorobenzoyl |
| (erythro-1-Ibq) | 3-chlorobenzoyl |
| (erythro-2-Ibq) | 3-chlorobenzoyl |
| (erythro-Ibr) | 2-chlorobenzoyl |
| (erythro-1-Ibr) | 2-chlorobenzoyl |
| (erythro-2-Ibr) | 2-chlorobenzoyl |
| (erythro-Ibs) | 4-fluorobenzoyl |
| (erythro-1-Ibs) | 4-fluorobenzoyl |
| (erythro-2-Ibs) | 4-fluorobenzoyl |
| (erythro-Ibt) | 3-fluorobenzoyl |
| (erythro-1-Ibt) | 3-fluorobenzoyl |
| (erythro-2-Ibt) | 3-fluorobenzoyl |
| (erythro-Ibu) | 2-fluorobenzoyl |
| (erythro-1-Ibu) | 2-fluorobenzoyl |
| (erythro-2-Ibu) | 2-fluorobenzoyl |
| (erythro-Ibv) | 2,2-dimethylpropanoyl (= pivaloyl) |
| (erythro-1-Ibv) | 2,2-dimethylpropanoyl (= pivaloyl) |
| (erythro-2-Ibv) | 2,2-dimethylpropanoyl (= pivaloyl) |
| (erythro-Ibw) | 3,3-dimethylbutanoyl |
| (erythro-1-Ibw) | 3,3-dimethylbutanoyl |
| (erythro-2-Ibw) | 3,3-dimethylbutanoyl |
| (erythro-Ibx) | pentanoyl |
| (erythro-1-Ibx) | pentanoyl |
| (erythro-2-Ibx) | pentanoyl |
| (erythro-Iby) | hexanoyl |
| (erythro-1-Iby) | hexanoyl |
| (erythro-2-Iby) | hexanoyl |
| (erythro-Ibz) | 2-nitrobenzoyl |
| (erythro-1-Ibz) | 2-nitrobenzoyl |
| (erythro-2-Ibz) | 2-nitrobenzoyl |
| (erythro-Ibaa) | 2-fluoroacetyl |
| (erythro-1-Ibaa) | 2-fluoroacetyl |
| (erythro-2-Ibaa) | 2-fluoroacetyl |
| (erythro-Ibab) | 2-chloroacetyl |
| (erythro-1-Ibab) | 2-chloroacetyl |
| (erythro-2-Ibab) | 2-chloroacetyl |
| (erythro-Ibac) | 2-bromoacetyl |
| (erythro-1-Ibac) | 2-bromoacetyl |
| (erythro-2-Ibac) | 2-bromoacetyl |
| (erythro-Ibad) | 2,2-dichloroacetyl |
| (erythro-1-Ibad) | 2,2-dichloroacetyl |
| (erythro-2-Ibad) | 2,2-dichloroacetyl |
| (erythro-Ibae) | 2-methoxyacetyl |
| (erythro-1-Ibae) | 2-methoxyacetyl |
| (erythro-2-Ibae) | 2-methoxyacetyl |
| (erythro-Ibaf) | 2,6-difluorobenzoyl |
| (erythro-1-Ibaf) | 2,6-difluorobenzoyl |
| (erythro-2-Ibaf) | 2,6-difluorobenzoyl |
| (erythro-Ibag) | C(O)C(O)OMe |
| (erythro-1-Ibag) | C(O)C(O)OMe |
| (erythro-2-Ibag) | C(O)C(O)OMe |
| (erythro-Ibah) | C(O)CH$_2$C(O)OMe |
| (erythro-1-Ibah) | C(O)CH$_2$C(O)OMe |
| (erythro-2-Ibah) | C(O)CH$_2$C(O)OMe |

Table 2d: (Erythro-Racemates)

Examples of the compounds of the formulae (erythro-Iba) to (erythro-Ibah) (see Table U3) are the compounds of the formulae in question in the form of the racemic mixture of the erythro isomers where the structural combination of groups $(R^2)_n$ and $(R^3)_m$ is defined according to a row number of Table 1.

The numeration is carried out according to "(formula) (row number)" without any brackets, for example erythro- Iba200=compound of the formula (erythro-Iba) having the structural combination of row 200 of Table 1.

Table 2e: (Optically Active Erythro-2 Enantiomers)

Examples of the compounds of the formulae (erythro-2-Iba) to (erythro-2-Ibah) (see Table U3) are the optically active erythro-2 compounds of the formulae in question in enriched form [=(2R,3S)-form having more than 80% ee] where the structural combination of groups $(R^2)_n$ and $(R^3)_m$ is defined according to a row number of Table 1.

Compounds are numbered "(formula)(row number)", without any brackets. For example, No. erythro-2-Iba789 refers to the compound of the formula (erythro-2-Iba) in which $(R^2)_n$=4-chloro and $(R^3)_m$=3-Cl, 5-F.

Table 2f: (Optically Active Erythro-1 Enantiomers)

Examples of the compounds of the formulae (erythro-1-Iba) to (erythro-1-Ibah) (see Table U3) are the optically active erythro-1 compounds of the formulae in question in enriched form [=(2S,3R)-form having more than 80% ee] where the structural combination of groups $(R^2)_n$ and $(R^3)_m$ is defined according to a row number of Table 1.

Compounds are numbered "(formula)(row number)", without any brackets. For example, No. erythro-1-Ibb5 refers to the compound of the formula (erythro-1-Ibb) in which $(R^2)_n$=3-chloro and $(R^3)_m$=2,6-F$_2$.

Physical Data for Compounds of Tables 2a-2f:

Test Methods:
1) NMR=$^1$H-NMR data (400 MHz, CDCl$_3$); characteristic chemical shifts [in ppm] are indicated for the example in question,
2) MS=mass spectrum, measured using a quadrupole instrument; electrospray ionization (+−), mass range 100-1000; molecular peak M or [M+H]+ or [M−1]+ or [M−2]+ or [M+1]+ are indicated for the example in question,
3) HPLC=High Performance Liquid Chromatography, column: Zorbax Eclipse, 50×3.0, C18 1.8 µm, mobile phase: water+0.06% formic acid/acrylonitrile+0.06% formic acid, gradient: 90:10, after 2 min 5:95; detector: DAD (210-400 nm); retention time (Rt) indicated for the example in question,
4) chiral HPLC=HPLC on a chiral column, column: Chiralpak IC, 250×4.6 mm, 5 µm DAIC 83325, detector wavelength: 210 nm; column temperature 25° C.,
   mobile phase a: (n-heptane:2-propanol), (60:40), Chromasolv, flow rate: 1.0 ml/min
   mobile phase b: (n-heptane:2-propanol), (70:30), Chromasolv, flow rate: 1.0 ml/min
   mobile phase c: (n-heptane:2-propanol), (80:20), Chromasolv, flow rate: 1.0 ml/min
   mobile phase d: (n-heptane:2-propanol), (90:10), Chromasolv, flow rate: 0.6 ml/min NMR data of compounds of Table 1, where in the compound in question R$^1$=H (accordingly, these compounds correspond to formula (Ia)):

$^1$H-NMR data (CDCl$_3$)-chemical shift of selected characteristic signals in ppm:

Ex. Iba1: erythro-Iba1: 7.34 (m, 6H), 6.95 (t, 2H), 4.23 (d, 1H), 3.81 (m, 1H), 3.49 (m, 1H), 3.33 (m, 1H), 1.98 (m, 1H), 1.78 (m, 1H), 1.15 (bs, 1H)
threo-Iba1: 7.17 (m, 5H), 7.06 (m, 1H), 6.71 (t, 2H), 4.19 (d, 1H), 3.87 (m, 1H), 3.79 (m, 1H), 3.48 (m, 1H), 2.53 (m, 1H), 2.28 (m, 1H), 1.32 (bs, 1H)

Ex. Iba2: Selected Peaks:
erythro-Iba2: 4.64 (d, 1H)
threo-Iba2: 4.53 (d, 1H)

Ex. Iba3: Selected peaks:
erythro-Iba3: 4.24 (d, 1H)
threo-Iba3: 4.19 (d, 1H)

Ex. Iba5: erythro-Iba5: 7.32 (m, 5H), 6.95 (t, 2H), 4.22 (d, 1H), 3.80 (m, 1H), 3.51 (m, 1H), 3.33 (m, 1H), 2.01 (m, 1H), 1.78 (m, 1H), 1.18 (bs, 1H)
threo-Iba5: 7.12 (m, 5H), 6.75 (t, 2H), 4.18 (d, 1H), 3.87 (m, 1H), 3.69 (m, 1H), 3.47 (m, 1H), 2.49 (m, 1H), 2.37 (m, 1H), 1.48 (bs, 1H)

Ex. Iba6: Selected peaks:
erythro-Iba6: 6.94 (t, 2H)
threo-Iba6: 6.74 (t, 2H)

Ex. Iba7: Selected peaks:
erythro-Iba7: 6.94 (t, 2H)
threo-Iba7: 6.75 (t, 2H)

Ex. Iba10: Selected peaks:
erythro-Iba10: 6.94 (t, 2H)
threo-Iba10: 6.76 (t, 2H)

Ex. Iba13: Selected peaks:
erythro-Iba13: 6.94 (t, 2H)
threo-Iba13: 6.72 (t, 2H)

Ex. Iba15: Selected peaks:
erythro-Iba15: 6.95 (t, 2H)
threo-Iba15: 6.74 (t, 2H)

Ex. Iba19: erythro-Iba19: 7.22 (m, 4H), 6.94 (t, 2H), 4.22 (d, 1H), 3.79 (m, 1H), 3.54 (m, 1H), 3.46 (m, 1H), 2.03 (m, 1H), 1.78 (m, 1H), 1.27 (bs, 1H)
threo-Iba19: 7.13 (m, 1H), 7.01 (m, 2H), 6.92 (m, 1H), 6.77 (t, 2H), 4.17 (d, 1H), 3.86 (m, 1H), 3.71 (m, 1H), 3.44 (m, 1H), 2.49 (m, 1H), 2.26 (m, 1H), 1.39 (bs, 1H)

Ex. Iba22: Selected peaks:
erythro-Iba22: 6.92 (t, 2H)
threo-Iba22: 6.77 (t, 2H)

Ex. Iba24: erythro-Iba24: 7.62 (m, 2H), 7.32 (m, 2H), 6.97 (t, 2H), 4.32 (d, 1H), 3.82 (m, 1H), 3.61 (m, 1H), 3.41 (m, 1H), 2.01 (m, 1H), 1.82 (m, 1H)
threo-Iba24: 7.49 (m, 5H), 7.08 (m, 2H), 6.79 (t, 2H), 4.23 (d, 1H), 3.88 (m, 1H), 3.72 (m, 1H), 3.44 (m, 1H), 2.50 (m, 1H), 2.27 (m, 1H)

Ex. Iba25: erythro-Iba25: 7.58 (m, 1H), 7.30 (m, 2H), 7.17 (t, 1H), 6.97 (t, 2H), 4.21 (d, 1H), 3.78 (m, 1H), 3.52 (m, 1H), 3.34 (m, 1H), 2.02 (m, 1H), 1.78 (m, 1H), 1.21 (bs, 1H)
threo-Iba25: 7.61 (m, 1H), 7.1 (m, 3H), 6.67 (t, 2H), 4.17 (d, 1H), 3.82 (m, 1H), 3.71 (m, 1H), 3.44 (m, 1H), 2.48 (m, 1H), 2.27 (m, 1H), 1.29 (bs, 1H)

Ex. Iba26: erythro-Iba26: 7.44 (m, 1H), 7.28 (m, 2H), 7.18 (t, 1H), 6.94 (t, 2H), 4.22 (d, 1H), 3.78 (m, 1H), 3.53 (m, 1H), 3.36 (m, 1H), 2.03 (m, 1H), 1.78 (m, 1H), 1.22 (bs, 1H)
threo-Iba26: 7.21 (m, 1H), 7.13 (m, 1H), 6.98 (t, 1H), 6.92 (m, 1H), 6.77 (t, 2H), 4.16 (d, 1H), 3.86 (m, 1H), 3.71 (m, 1H), 3.44 (m, 1H), 2.49 (m, 1H), 2.27 (m, 1H), 1.33 (bs, 1H)

Ex. Iba27: Selected peaks:
erythro-Iba27: 4.23 (d, 1H)
threo-Iba27: 4.17 (d, 1H)

Ex. Iba28: Selected peaks:
erythro-Iba28: 4.19 (d, 1H)
threo-Iba28: 4.10 (d, 1H)

Ex. Iba30: erythro-Iba30: 7.31 (m, 1H), 7.12 (m, 1H), 6.97 (m, 5H), 4.22 (d, 1H), 3.68 (m, 2H), 3.45 (m, 1H), 2.10 (m, 2H), 1.38 (bs, 1H)
threo-Iba30: 7.25 (m, 1H), 6.98 (m, 6H), 4.10 (d, 1H), 3.63 (m, 2H), 3.39 (m, 1H), 2.26 (m, 1H), 2.14 (m, 1H), 1.35 (bs, 1H)

Ex. Iba31: Selected peaks:
erythro-Iba31: 4.21 (d, 1H)
threo-Iba31: 4.08 (d, 1H)

Ex. Iba32: Selected peaks:
  erythro-Iba32: 4.20 (d, 1H)
  threo-Iba32: 4.08 (d, 1H)
Ex. Iba33: Selected peaks:
  erythro-Iba33: 4.21 (d, 1H)
  threo-Iba33: 4.08 (d, 1H)
Ex. Iba34: Selected peaks:
  erythro-Iba34: 4.19 (d, 1H)
  threo-Iba34: 4.07 (d, 1H)
Ex. Iba35: Selected peaks:
  erythro-Iba35: 4.21 (d, 1H)
  threo-Iba35: 4.15 (d, 1H)
Ex. Iba37: Selected peaks:
  erythro-Iba37: 4.35 (d, 1H)
  threo-Iba37: 4.15 (d, 1H)
Ex. Iba40: Selected peaks:
  erythro-Iba40: 4.57 (d, 1H)
  threo-Iba40: 4.36 (d, 1H)
Ex. Iba42: Selected peaks:
  erythro-Iba42: 4.61 (d, 1H)
  threo-Iba42: 4.42 (d, 1H)
Ex. Iba46: erythro-Iba46: 7.01 (m, 6H), 4.23 (d, 1H), 3.69 (m, 2H), 3.48 (m, 1H), 2.04 (m, 2H), 1.38 (bs, 1H)
  threo-Iba46: 6.96 (m, 6H), 4.07 (d, 1H), 3.63 (m, 2H), 3.38 (m, 1H), 2.27 (m, 1H), 2.12 (m, 1H), 1.26 (bs, 1H)
Ex. Iba50: Selected peaks:
  erythro-Iba50: 4.24 (d, 1H)
  threo-Iba50: 4.09 (d, 1H)
Ex. Iba51: erythro-Iba51: 7.41 (m, 2H), 7.15 (m, 2H), 6.94 (m, 2H), 4.38 (d, 1H), 3.74 (m, 2H), 3.53 (m, 1H), 2.08 (m, 2H), 1.26 (t, 1H)
  threo-Iba51: 7.48 (m, 2H), 7.18 (t, 1H), 6.93 (m, 3H), 4.13 (d, 1H), 3.64 (m, 2H), 3.39 (m, 1H), 2.28 (m, 1H), 2.17 (m, 1H), 1.26 (bs, 1H)
Ex. Iba52: erythro-Iba52: 7.37 (m, 1H), 7.03 (m, 5H), 4.22 (d, 1H), 3.37 (m, 2H), 3.48 (m, 1H), 2.03 (m, 2H), 1.40 (bs, 1H)
  threo-Iba52: 7.44 (m, 1H), 7.18 (m, 1H), 6.97 (m, 4H), 4.12 (d, 1H), 3.64 (m, 2H), 3.39 (m, 1H), 2.26 (m, 1H), 2.13 (m, 1H), 1.28 (bs, 1H)
Ex. Iba53: erythro-Iba53: 7.21 (m, 1H), 7.03 (m, 5H), 4.22 (d, 1H), 3.67 (m, 2H), 3.48 (m, 1H), 2.03 (m, 2H), 1.40 (bs, 1H)
  threo-Iba53: 7.31 (m, 1H), 6.95 (m, 5H), 4.07 (d, 1H), 3.62 (m, 2H), 3.40 (m, 1H), 2.26 (m, 1H), 2.12 (m, 1H), 1.40 (bs, 1H)
Ex. Iba54: Selected peaks:
  erythro-Iba54: 4.22 (d, 1H)
  threo-Iba54: 4.07 (d, 1H)
Ex. Iba55: Selected peaks:
  erythro-Iba55: 4.21 (d, 1H)
  threo-Iba55: 4.18 (d, 1H)
Ex. Iba57: erythro-Iba57: 7.37 (m, 1H), 7.10 (m, 2H), 6.89 (m, 1H), 4.23 (d, 1H), 3.82 (m, 1H), 3.53 (m, 1H), 3.34 (m, 1H), 2.00 (m, 1H), 1.81 (m, 1H), 1.33 (bs, 1H)
  threo-Iba57: 7.12 (m, 1H), 6.94 (m, 4H), 6.71 (m, 1H), 4.18 (d, 1H), 3.91 (m, 1H), 3.72 (m, 1H), 3.46 (m, 1H), 2.51 (m, 1H), 2.26 (m, 1H), 1.41 (bs, 1H)
Ex. Iba59: erythro-Iba59: 7.32 (m, 4H), 7.13 (m, 1H), 6.89 (m, 1H), 4.21 (d, 1H), 3.82 (m, 1H), 3.54 (m, 1H), 3.35 (m, 1H), 2.00 (m, 1H), 1.79 (m, 1H), 1.21 (bs, 1H)
  threo-Iba59: 7.18 (m, 3H), 7.09 (m, 1H), 6.97 (m, 1H), 6.72 (m, 1H), 4.16 (d, 1H), 3.91 (m, 1H), 3.72 (m, 1H), 3.48 (m, 1H), 2.51 (m, 1H), 2.28 (m, 1H), 1.38 (bs, 1H)
Ex. Iba60: Selected peaks:
  erythro-Iba60: 4.22 (d, 1H)
  threo-Iba60: 4.17 (d, 1H)
Ex. Iba61: Selected peaks:
  erythro-Iba61: 4.19 (d, 1H)
  threo-Iba61: 4.15 (d, 1H)
Ex. Iba64: Selected peaks:
  erythro-Iba64: 4.23 (d, 1H)
  threo-Iba64: 4.32 (d, 1H)
Ex. Iba67: Selected peaks:
  erythro-Iba67: 4.16 (d, 1H)
  threo-Iba67: 4.14 (d, 1H)
Ex. Iba70: Selected peaks:
  erythro-Iba70: 4.60 (d, 1H)
  threo-Iba70: 4.48 (d, 1H)
Ex. Iba73: Selected peaks:
  erythro-Iba73: 4.23 (d, 1H)
  threo-Iba73: 4.15 (d, 1H)
Ex. Iba76: Selected peaks:
  erythro-Iba76: 4.24 (d, 1H)
  threo-Iba76: 4.18 (d, 1H)
Ex. Iba77: Selected peaks:
  erythro-Iba77: 4.23 (d, 1H)
  threo-Iba77: 4.18 (d, 1H)
Ex. Iba78: Selected peaks:
  erythro-Iba78: 4.33 (d, 1H)
  threo-Iba78: 4.22 (d, 1H)
Ex. Iba79: erythro-Iba79: 7.58 (m, 1H), 7.32 (m, 1H), 7.16 (m, 2H), 6.90 (m, 1H), 4.22 (d, 1H), 3.79 (m, 1H), 3.56 (m, 1H), 3.36 (m, 1H), 2.00 (m, 1H), 1.80 (m, 1H), 1.30 (bs, 1H)
  threo-Iba79: 7.39 (m, 1H), 7.12 (m, 1H), 6.99 (m, 2H), 6.74 (m, 1H), 4.15 (d, 1H), 3.88 (m, 1H), 3.72 (m, 1H), 3.45 (m, 1H), 2.50 (m, 1H), 2.26 (m, 1H), 1.42 (bs, 1H)
Ex. Iba80: erythro-Iba80: 7.43 (m, 1H), 7.18 (m, 3H), 6.90 (m, 1H), 4.21 (d, 1H), 3.81 (m, 1H), 3.55 (m, 1H), 3.35 (m, 1H), 2.00 (m, 1H), 1.81 (m, 1H), 1.33 (bs, 1H)
  threo-Iba80: 7.24 (m, 1H), 7.02 (m, 3H), 6.72 (m, 1H), 4.15 (d, 1H), 3.88 (m, 1H), 3.72 (m, 1H), 3.44 (m, 1H), 2.51 (m, 1H), 2.25 (m, 1H), 1.46 (bs, 1H)
Ex. Iba81: Selected peaks:
  erythro-Iba81: 6.89 (t, 1H)
  threo-Iba81: 6.76 (t, 1H)
Ex. Iba84: Selected peaks:
  erythro-Iba84: 4.17 (d, 1H)
  threo-Iba84: 4.14 (d, 1H)
Ex. Iba85: Selected peaks:
  erythro-Iba85: 6.72 (t, 1H)
  threo-Iba85: 6.52 (t, 1H)
Ex. Iba86: Selected peaks:
  erythro-Iba86: 4.17 (d, 1H)
  threo-Iba86: 4.11 (d, 1H)
Ex. Iba87: Selected peaks:
  erythro-Iba87: 6.73 (t, 2H)
  threo-Iba87: 6.52 (t, 2H)
Ex. Iba88: Selected peaks:
  erythro-Iba88: 6.72 (t, 2H)
  threo-Iba88: 6.54 (t, 2H)
Ex. Iba94: Selected peaks:
  erythro-Iba94: 4.13 (d, 1H)
  threo-Iba94: 4.09 (d, 1H)
Ex. Iba96: Selected peaks:
  erythro-Iba96: 4.61 (d, 1H)
  threo-Iba96: 4.51 (d, 1H)
Ex. Iba97: Selected peaks:
  erythro-Iba97: 4.55 (d, 1H)
  threo-Iba97: 4.44 (d, 1H)
Ex. Iba100: Selected peaks:
  erythro-Iba100: 4.18 (d, 1H)
  threo-Iba100: 4.11 (d, 1H)

Ex. Iba106: Selected peaks:
  erythro-Iba106: 4.17 (d, 1H)
  threo-Iba106: 4.11 (d, 1H)
Ex. Iba107: Selected peaks:
  erythro-Iba107: 4.18 (d, 1H)
  threo-Iba107: 4.11 (d, 1H)
Ex. Iba108: Selected peaks:
  erythro-Iba108: 4.17 (d, 1H)
  threo-Iba108: 4.14 (d, 1H)
Ex. Iba111: Selected peaks:
  erythro-Iba111: 4.20 (d, 1H)
  threo-Iba111: 4.14 (d, 1H)
Ex. Iba113: Selected peaks:
  erythro-Iba113: 4.17 (d, 1H)
  threo-Iba113: 4.12 (d, 1H)
Ex. Iba127: Selected peaks:
  erythro-Iba127: 4.18 (d, 1H)
  threo-Iba127: 4.13 (d, 1H)
Ex. Iba134: Selected peaks:
  erythro-Iba134: 4.18 (d, 1H)
  threo-Iba134: 4.12 (d, 1H)
Ex. Iba136: Selected peaks:
  erythro-Iba136: 4.15 (d, 1H)
  threo-Iba136: 3.96 (d, 1H)
Ex. Iba138: erythro-Iba138: 7.31 (m, 2H), 7.01 (m, 1H), 6.89 (m, 1H), 6.70 (m, 2H), 4.17 (d, 1H), 3.70 (m, 1H), 3.49 (m, 1H), 3.31 (m, 1H), 2.08 (m, 1H), 1.37 (bs, 1H)
  threo-Iba138: 7.31 (m, 2H), 6.98 (m, 2H), 6.71 (m, 3H), 3.98 (d, 1H), 3.64 (m, 1H), 3.33 (m, 2H), 2.25 (m, 1H), 2.04 (m, 1H), 1.28 (bs, 1H)
Ex. Iba140: Selected peaks:
  erythro-Iba140: 4.14 (d, 1H)
  threo-Iba140: 3.97 (d, 1H)
Ex. Iba154: erythro-Iba154: 7.19 (m, 1H), 7.19 (t, 1H), 6.98 (m, 1H), 6.73 (m, 1H), 6.64 (m, 2H), 4.15 (d, 1H), 3.72 (m, 1H), 3.48 (m, 1H), 3.28 (m, 1H), 2.06 (m, 2H), 1.34 (bs, 1H)
  threo-Iba154: 7.25 (m, 2H), 7.05 (m, 2H), 6.70 (m, 2H), 3.96 (d, 1H), 3.66 (m, 1H), 3.33 (m, 2H), 2.25 (m, 1H), 2.02 (m, 1H), 1.33 (bs, 1H)
Ex. Iba160: Selected peaks:
  erythro-Iba160: 4.36 (d, 1H)
  threo-Iba160: 4.06 (d, 1H)
Ex. Iba161: Selected peaks:
  erythro-Iba161: 4.36 (d, 1H)
  threo-Iba161: 4.6 (d, 1H)
Ex. Iba163: Selected peaks:
  erythro-Iba163: 4.22 (d, 1H)
  threo-Iba163: 4.10 (d, 1H)
Ex. Iba165: Selected peaks:
  erythro-Iba165: 4.22 (d, 1H)
  threo-Iba165: 4.11 (d, 1H)
Ex. Iba166: Selected peaks:
  erythro-Iba166: 4.24 (d, 1H)
  threo-Iba166: 4.09 (d, 1H)
Ex. Iba167: Selected peaks:
  erythro-Iba167: 4.22 (d, 1H)
  threo-Iba167: 4.08 (d, 1H)
Ex. Iba181: erythro-Iba181: 7.14 (m, 4H), 7.00 (m, 1H), 6.98 (m, 1H), 4.25 (d, 1H), 3.71 (m, 2H), 3.48 (m, 1H), 2.06 (m, 2H), 1.36 (bs, 1H)
  threo-Iba181: 7.00 (m, 6H), 4.08 (d, 1H), 3.66 (m, 2H), 3.48 (m, 1H), 2.29 (m, 1H), 2.16 (m, 1H), 1.26 (bs, 1H)
Ex. Iba184: Selected peaks:
  erythro-Iba184: 4.26 (d, 1H)
  threo-Iba184: 4.10 (d, 1H)
Ex. Iba188: Selected peaks:
  erythro-Iba188: 4.24 (d, 1H)
  threo-Iba188: 4.07 (d, 1H)
Ex. Iba189: Selected peaks:
  erythro-Iba189: 4.24 (d, 1H)
  threo-Iba189: 4.08 (d, 1H)
Ex. Iba192: Selected peaks:
  erythro-Iba192: 4.17 (d, 1H)
  threo-Iba192: 3.97 (d, 1H)
Ex. Iba221: Selected peaks:
  erythro-Iba221: 4.20 (d, 1H), 1.26 (bs, 1H)
  threo-Iba221: 4.10 (d, 1H), 1.19 (bs, 1H)
Ex. Iba235: Selected peaks:
  erythro-Iba235: 4.22 (d, 1H)
  threo-Iba235: 4.09 (d, 1H)
Ex. Iba241: Selected peaks:
  erythro-Iba241: 4.22 (d, 1H)
  threo-Iba241: 4.08 (d, 1H)
Ex. Iba242: Selected peaks:
  erythro-Iba242: 4.21 (d, 1H)
  threo-Iba242: 4.08 (d, 1H)
Ex. Iba262: Selected peaks:
  erythro-Iba262: 4.50 (d, 1H)
  threo-Iba262: 4.26 (d, 1H)
Ex. Iba268: Selected peaks:
  erythro-Iba268: 4.21 (d, 1H)
  threo-Iba268: 4.11 (d, 1H)
Ex. Iba269: Selected peaks:
  erythro-Iba269: 4.22 (d, 1H)
  threo-Iba269: 4.11 (d, 1H)
Ex. Iba275: Selected peaks:
  erythro-Iba275: 4.13 (d, 1H)
  threo-Iba275: 3.97 (d, 1H)
Ex. Iba289: Selected peaks:
  erythro-Iba289: 4.16 (d, 1H)
  threo-Iba289: 3.71 (d, 1H)
Ex. Iba327: Selected peaks:
  erythro-Iba327: 4.15 (d, 1H)
  threo-Iba327: 3.97 (d, 1H)
Ex. Iba352: Selected peaks:
  erythro-Iba352: 4.31 (d, 1H)
  threo-Iba352: 4.07 (d, 1H)
Ex. Iba354: erythro-Iba354: 7.29 (m, 3H), 7.00 (m, 3H), 6.84 (m, 2H), 4.16 (d, 1H), 3.69 (m, 1H), 3.48 (m, 1H), 3.30 (m, 1H), 2.09 (m, 2H), 1.26 (bs, 1H)
  threo-Iba354: 7.28 (m, 3H), 6.98 (m, 5H), 3.98 (d, 1H), 3.61 (m, 1H), 3.31 (m, 2H), 2.23 (m, 1H), 2.07 (m, 1H), 1.23 (bs, 1H)
Ex. Iba370: erythro-Iba370: 7.29 (m, 3H), 7.00 (m, 3H), 6.84 (m, 2H), 4.16 (d, 1H), 3.69 (m, 1H), 3.48 (m, 1H), 3.30 (m, 1H), 2.09 (m, 2H), 1.26 (bs, 1H)
  threo-Iba370: 7.28 (m, 3H), 6.98 (m, 5H), 3.98 (d, 1H), 3.61 (m, 1H), 3.31 (m, 2H), 2.23 (m, 1H), 2.07 (m, 1H), 1.23 (bs, 1H)
Ex. Iba376: Selected peaks:
  erythro-Iba376: 4.15 (d, 1H)
  threo-Iba376: 3.94 (d, 1H)
Ex. Iba424: Selected peaks:
  erythro-Iba424: 4.27 (d, 1H)
  threo-Iba424: 4.14 (d, 1H)
Ex. Iba431: Selected peaks:
  erythro-Iba431: 4.24 (d, 1H)
  threo-Iba431: 4.06 (d, 1H)
Ex. Iba516: Selected peaks:
  erythro-Iba516: 4.22 (d, 1H)
  threo-Iba516: 4.09 (d, 1H)

Ex. Iba532: Selected peaks:
  erythro-Iba532: 4.22 (d, 1H)
  threo-Iba532: 4.05 (d, 1H)
Ex. Iba538: Selected peaks:
  erythro-Iba538: 4.22 (d, 1H)
  threo-Iba538: 4.05 (d, 1H)
Ex. Iba539: Selected peaks:
  erythro-Iba539: 4.22 (d, 1H)
  threo-Iba539: 4.05 (d, 1H)
Ex. Iba937: erythro-Iba937: 7.27 (m, 3H), 7.06 (m, 3H), 6.83 (m, 2H), 4.15 (d, 1H), 3.69 (m, 1H), 3.50 (m, 1H), 3.25 (m, 1H), 2.11 (m, 2H), 1.31 (bs, 1H)
  threo-Iba937: 7.28 (m, 3H), 6.98 (m, 5H), 3.96 (d, 1H), 3.61 (m, 1H), 3.39 (m, 1H), 3.26 (m, 1H), 2.28 (m, 1H), 2.11 (m, 1H), 1.23 (bs, 1H)
Ex. Iba1056: Selected peaks:
  erythro-Iba1056: 4.12 (d, 1H)
  threo-Iba1056: 3.96 (d, 1H)
Ex. Iba1058: Selected peaks:
  erythro-Iba1058: 4.08 (d, 1H)
  threo-Iba1058: 3.94 (d, 1H)
Ex. Iba1072: Selected peaks:
  erythro-Iba1072: 4.10 (d, 1H)
  threo-Iba1072: 3.92 (d, 1H)
Ex. Iba1085: Selected peaks:
  erythro-Iba1085: 4.09 (d, 1H)
  threo-Iba1085: 3.92 (d, 1H)
Ex. Iba1099: erythro-Iba1099: 7.12 (m, 1H), 6.96 (m, 1H), 6.85 (m, 1H), 6.74 (m, 2H), 4.17 (d, 1H), 3.73 (m, 1H), 3.47 (m, 1H), 3.26 (m, 1H), 2.06 (m, 2H), 1.37 (bs, 1H)
NMR data of compounds of Tables U1, U2 and U3:
$^1$H-NMR data (CDCl$_3$)-chemical shift of selected characteristic signals in ppm:
Ex. Ibb1: Selected peaks:
  erythro-Ibb1: 6.94 (t, 2H), 1.90 (s, 3H)
  threo-Ibb1: 6.71 (t, 2H), 1.97 (s, 3H)
Ex. Ibb19: erythro-Ibb19: 7.23 (m, 3H), 7.16 (m, 1H), 6.94 (t, 2H), 4.18 (d, 1H), 3.92 (m, 1H), 3.72
  threo-Ibb19: 7.15 (m, 1H), 7.00 (m, 2H), 6.91 (m, 1H), 6.76 (t, 2H), 4.14 (d, 1H), 4.06 (m, 1H), 3.82 (m, 2H), 2.59 (m, 1H), 2.35 (m, 1H), 1.97 (s, 3H)
Ex. Ibc19: erythro-Ibc19: 7.23 (m, 3H), 7.16 (m, 1H), 6.94 (t, 2H), 4.18 (d, 1H), 3.92 (m, 1H), 3.72 (m, 2H), 2.20 (q, 2H), 2.11 (m, 1H), 1.83 (m, 1H), 1.06 (t, 3H)
  threo-Ibc19: 7.15 (m, 1H), 7.00 (m, 2H), 6.91 (m, 1H), 6.76 (t, 2H), 4.14 (d, 1H), 4.06 (m, 1H), 3.82 (m, 2H), 2.59 (m, 1H), 2.36 (m, 1H), 2.23 (q, 2H), 1.08 (t, 3H)
Ex. Ibe19: erythro-Ibe19: 7.23 (m, 3H), 7.16 (m, 1H), 6.94 (t, 2H), 4.18 (d, 1H), 3.92 (m, 1H), 3.72 (m, 2H), 2.43 (quint, 1H), 2.11 (m, 1H), 1.83 (m, 1H), 1.08 (d, 6H)
  threo-Ibe19: 7.15 (m, 1H), 7.00 (m, 2H), 6.91 (m, 1H), 6.76 (t, 2H), 4.14 (d, 1H), 4.06 (m, 1H), 3.82 (m, 2H), 2.59 (m, 1H), 2.36 (m, 1H), 2.43 (quint, 1H), 1.2 (d, 6H)
Ex. Ibl19: erythro-Ibl19: 7.23 (m, 3H), 7.16 (m, 1H), 6.94 (t, 2H), 4.18 (d, 1H), 3.92 (m, 1H), 3.72 (m, 2H), 2.18 (t, 2H), 2.11 (m, 1H), 1.83 (m, 1H), 1.51 (m, 2H), 1.31 (m, 2H), 0.88 (d, 3H)
  threo-Ibl19: 7.15 (m, 1H), 7.00 (m, 2H), 6.91 (m, 1H), 6.76 (t, 2H), 4.14 (d, 1H), 4.06 (m, 1H), 3.82 (m, 2H), 2.59 (m, 1H), 2.36 (m, 1H), 2.18 (t, 2H), 1.51 (m, 2H), 1.31 (m, 2H), 0.90 (d, 3H)
Ex. Ibv19: erythro-Ibv19: 7.23 (m, 3H), 7.16 (m, 1H), 6.94 (t, 2H), 4.18 (d, 1H), 3.98 (m, 1H), 3.70 (m, 2H), 2.09 (m, 1H), 1.84 (m, 1H), 1.11 (s, 9H)
  threo-Ibv19: 7.15 (m, 1H), 7.00 (m, 2H), 6.91 (m, 1H), 6.76 (t, 2H), 4.14 (d, 1H), 4.15 (m, 1H), 3.79 (m, 2H), 2.59 (m, 1H), 2.35 (m, 1H), 1.16 (s, 9H)
Ex. Ibx19: Selected peaks:
  erythro-Ibx19: 6.92 (t, 2H)
  threo-Ibx19: 6.75 (t, 2H)
Ex. Ibh25: Selected peaks:
  erythro-Ibh25: 6.95 (t, 2H), 4.18 (d, 1H), 3.71 (s, 1H)
  threo-Ibh25: 6.78 (t, 2H), 4.14 (d, 1H), 3.74 (s, 1H)
Ex. Ibm25: Selected peaks:
  erythro-Ibm25: 6.95 (t, 2H), 4.18 (d, 1H), 0.90 (t, 3H)
  threo-Ibm25: 6.78 (t, 2H), 4.13 (d, 1H), 0.90 (t, 3H)
Ex. Ibw25: Selected peaks:
  erythro-Ibw25: 6.96 (t, 2H), 2.08 (s, 1H)
  threo-Ibw25: 6.76 (t, 2H), 2.14 (s, 1H)
Ex. Iby25: Selected peaks:
  erythro-Iby25: 6.95 (t, 2H)
  threo-Iby25: 6.76 (t, 2H)
Ex. Ibh26: Selected peaks:
  erythro-Ibh26: 6.95 (t, 2H), 3.71 (s, 3H)
  threo-Ibh26: 6.78 (t, 2H), 3.74 (s, 3H)
Ex. Ibm26: Selected peaks:
  erythro-Ibm26: 6.94 (t, 2H), 0.90 (t, 3H)
  threo-Ibm26: 6.76 (t, 2H), 0.90 (t, 3H)
Ex. Ibw26: Selected peaks:
  erythro-Ibw26: 6.98 (t, 2H), 2.08 (s, 2H)
  threo-Ibw26: 6.76 (t, 2H), 2.14 (s, 2H)
Ex. Iby26: Selected peaks:
  erythro-Iby26: 6.97 (t, 2H)
  threo-Iby26: 6.76 (t, 2H)
Ex. Ibb30: Selected peaks:
  erythro-Ibb30: 4.16 (d, 1H), 1.96 (s, 3H)
  threo-Ibb30: 4.06 (d, 1H), 1.99 (s, 3H)
Ex. Ibe30: Selected peaks:
  erythro-Ibe30: 4.18 (d, 1H), 1.12 (d, 1H)
  threo-Ibe30: 4.10 (d, 1H), 1.21 (d, 1H)
Ex. Ibb46: Selected peaks:
  erythro-Ibb46: 4.17 (d, 1H), 2.00 (s, 3H)
  threo-Ibb46: 4.02 (d, 1H), 1.97 (s, 3H)
Ex. Ibe46: Selected peaks:
  erythro-Ibe46: 4.18 (d, 1H), 1.13 (s, 6H)
  threo-Ibe46: 4.02 (d, 1H), 1.10 (s, 6H)
Ex. Ibv46: Selected peaks:
  erythro-Ibv46: 4.18 (d, 1H), 1.17 (s, 9H)
  threo-Ibv46: 4.10 (d, 1H), 1.13 (s, 9H)
Ex. Ibb52: Selected peaks:
  erythro-Ibb52: 4.15 (d, 1H), 2.00 (s, 3H)
  threo-Ibb52: 4.01 (d, 1H), 1.97 (s, 3H)
Ex. Ibe52: Selected peaks:
  erythro-Ibe52: 4.17 (d, 1H), 1.13 (s, 6H)
  threo-Ibe52: 4.02 (d, 1H), 1.10 (s, 6H)
Ex. Ibh52: Selected peaks:
  erythro-Ibh52: 4.16 (d, 1H), 3.76 (s, 3H)
  threo-Ibh52: 4.04 (d, 1H), 3.74 (s, 3H)
Ex. Ibm52: Selected peaks:
  erythro-Ibm52: 4.17 (d, 1H), 0.93 (t, 3H)
  threo-Ibm52: 4.01 (d, 1H), 0.93 (t, 3H)
Ex. Ibv52: Selected peaks:
  erythro-Ibv52: 4.18 (d, 1H), 1.17 (s, 9H)
  threo-Ibv52: 4.10 (d, 1H), 1.13 (s, 9H)
Ex. Iby52: Selected peaks:
  erythro-Iby52: 4.17 (d, 1H)
  threo-Iby52: 4.01 (d, 1H)
Ex. Ibh53: Selected peaks:
  erythro-Ibh53: 4.16 (d, 1H), 3.76 (s, 3H)
  threo-Ibh53: 4.04 (d, 1H), 3.74 (s, 3H)

Ex. Ibl53: Selected peaks:
  erythro-Ibl53: 4.17 (d, 1H), 0.91 (t, 3H)
  threo-Ibl53: 4.02 (d, 1H), 0.90 (t, 3H)
Ex. Ibm53: Selected peaks:
  erythro-Ibm53: 4.17 (d, 1H), 0.91 (t, 3H)
  threo-Ibm53: 4.01 (d, 1H), 0.91 (t, 3H)
Ex. Ibw53: Selected peaks:
  erythro-Ibw53: 4.18 (d, 1H), 1.00 (s, 9H)
  threo-Ibw53: 4.01 (d, 1H), 0.98 (s, 9H)
Ex. Ibx53: Selected peaks:
  erythro-Ibx53: 4.16 (d, 1H)
  threo-Ibx53: 4.02 (d, 1H)
Ex. Iby53: Selected peaks:
  erythro-Iby53: 4.17 (d, 1H)
  threo-Iby53: 4.02 (d, 1H)
Ex. Ibb73: Selected peaks:
  erythro-Ibb73: 4.19 (d, 1H), 1.94 (s, 3H)
  threo-Ibb73: 4.14 (d, 1H), 1.99 (s, 3H)
Ex. Ibb79: Selected peaks:
  erythro-Ibb79: 4.17 (d, 1H), 1.95 (s, 3H)
  threo-Ibb79: 4.14 (d, 1H), 1.99 (s, 3H)
Ex. Ibab190: Selected peaks:
  erythro-Ibab190: 3.94 (s, 2H)
  threo-Ibab190: 3.99 (s, 2H)
Ex. Ibb289: Selected peaks:
  erythro-Ibb289: 4.12 (d, 1H)
  threo-Ibb289: 3.91 (d, 1H)
Ex. Ibh289: Selected peaks:
  erythro-Ibh289: 4.10 (d, 1H), 3.76 (s, 3H)
  threo-Ibh289: 3.92 (d, 1H), 3.74 (s, 3H)

NMR data of optically active erythro-1 enantiomers of compounds according to the invention of Table 1, where in the compound in question $R^1$=H (accordingly, these compounds correspond to formula (Ia)):

$^1$H-NMR data (CDCl$_3$)-chemical shift of selected characteristic signals in ppm:

Ex. Iba1: erythro-1-Iba1: 7.34 (m, 6H), 6.95 (t, 2H), 4.23 (d, 1H), 3.81 (m, 1H), 3.49 (m, 1H), 3.33 (m, 1H), 1.98 (m, 1H), 1.78 (m, 1H), 1.15 (bs, 1H)
Ex. Iba5: erythro-1-Iba5: 7.32 (m, 5H), 6.95 (t, 2H), 4.22 (d, 1H), 3.80 (m, 1H), 3.51 (m, 1H), 3.33 (m, 1H), 2.01 (m, 1H), 1.78 (m, 1H), 1.18 (bs, 1H)
Ex. Iba19: erythro-1-Iba19: 7.22 (m, 4H), 6.94 (t, 2H), 4.22 (d, 1H), 3.79 (m, 1H), 3.54 (m, 1H), 3.46 (m, 1H), 2.03 (m, 1H), 1.78 (m, 1H), 1.27 (bs, 1H)
Ex. Iba24: erythro-1-Iba24: 7.62 (m, 2H), 7.32 (m, 2H), 6.97 (t, 2H), 4.32 (d, 1H), 3.82 (m, 1H), 3.61 (m, 1H), 3.41 (m, 1H), 2.01 (m, 1H), 1.82 (m, 1H)
Ex. Iba25: erythro-1-Iba25: 7.58 (m, 1H), 7.30 (m, 2H), 7.17 (m, 1H), 6.97 (t, 2H), 4.21 (d, 1H), 3.78 (m, 1H), 3.52 (m, 1H), 3.34 (m, 1H), 2.02 (m, 1H), 1.78 (m, 1H), 1.21 (bs, 1H)
Ex. Iba26: erythro-1-Iba26: 7.44 (m, 1H), 7.28 (m, 2H), 7.18 (m, 1H), 6.94 (t, 2H), 4.22 (d, 1H), 3.78 (m, 1H), 3.53 (m, 1H), 3.36 (m, 1H), 2.03 (m, 1H), 1.78 (m, 1H), 1.22 (bs, 1H)
Ex. Iba28: erythro-1-Iba28: 7.26 (m, 3H), 7.09 (m, 3H), 6.94 (m, 2H), 4.19 (d, 1H), 3.65 (m, 2H), 3.43 (m, 1H), 2.00 (m, 2H), 1.26 (bs, 1H)
Ex. Iba30: erythro-1-Iba30: 7.31 (m, 1H), 7.12 (m, 1H), 6.97 (m, 5H), 4.22 (d, 1H), 3.68 (m, 2H), 3.45 (m, 1H), 2.10 (m, 2H), 1.38 (bs, 1H)
Ex. Iba46: erythro-1-Iba46: 7.01 (m, 6H), 4.23 (d, 1H), 3.69 (m, 2H), 3.48 (m, 1H), 2.04 (m, 2H), 1.38 (bs, 1H)
Ex. Iba51: erythro-1-Iba51: 7.41 (m, 2H), 7.15 (m, 2H), 6.94 (m, 2H), 4.38 (d, 1H), 3.74 (m, 1H), 3.53 (m, 1H), 2.08 (m, 2H), 1.26 (bs, 1H)
Ex. Iba52: erythro-1-Iba52: 7.37 (m, 1H), 7.03 (m, 5H), 4.22 (d, 1H), 3.37 (m, 2H), 3.48 (m, 1H), 2.03 (m, 2H), 1.40 (bs, 1H)
Ex. Iba53: erythro-1-Iba53: 7.21 (m, 1H), 7.03 (m, 5H), 4.22 (d, 1H), 3.67 (m, 2H), 3.48 (m, 1H), 2.03 (m, 2H), 1.40 (bs, 1H)
Ex. Iba57: erythro-1-Iba57: 7.37 (m, 1H), 7.10 (m, 2H), 6.89 (m, 1H), 4.23 (d, 1H), 3.82 (m, 1H), 3.53 (m, 1H), 3.34 (m, 1H), 2.00 (m, 1H), 1.81 (m, 1H), 1.33 (bs, 1H)
Ex. Iba59: erythro-1-Iba59: 7.32 (m, 4H), 7.13 (m, 1H), 6.89 (m, 1H), 4.21 (d, 1H), 3.82 (m, 1H), 3.54 (m, 1H), 3.35 (m, 1H), 2.00 (m, 1H), 1.79 (m, 1H), 1.21 (bs, 1H)
Ex. Iba64: Selected peaks: erythro-1-Iba64: 4.23 (d, 1H)
Ex. Iba80: erythro-1-Iba80: 7.43 (m, 1H), 7.18 (m, 3H), 6.90 (m, 1H), 4.21 (d, 1H), 3.81 (m, 1H), 3.55 (m, 1H), 3.35 (m, 1H), 2.00 (m, 1H), 1.81 (m, 1H), 1.33 (bs, 1H)
Ex. Iba106: Selected peaks: erythro-1-Iba106: 4.17 (d, 1H)
Ex. Iba134: Selected peaks: erythro-1-Iba134: 4.18 (d, 1H)
Ex. Iba138: erythro-1-Iba138: 7.31 (m, 2H), 7.01 (m, 1H), 6.89 (m, 1H), 6.70 (m, 2H), 4.17 (d, 1H), 3.70 (m, 1H), 3.49 (m, 1H), 3.31 (m, 1H), 2.08 (m, 1H), 1.37 (bs, 1H)
Ex. Iba140: Selected peaks: erythro-1-Iba140: 4.14 (d, 1H)
Ex. Iba154: erythro-1-Iba154: 7.19 (m, 1H), 7.19 (t, 1H), 6.98 (m, 1H), 6.73 (m, 1H), 6.64 (m, 2H), 4.15 (d, 1H), 3.72 (m, 1H), 3.48 (m, 1H), 3.28 (m, 1H), 2.06 (m, 2H), 1.34 (bs, 1H)
Ex. Iba181: erythro-1-Iba181: 7.14 (m, 4H), 7.00 (m, 1H), 6.98 (m, 1H), 4.25 (d, 1H), 3.71 (m, 2H), 3.48 (m, 1H), 2.06 (m, 2H), 1.36 (bs, 1H)
Ex. Iba221: Selected peaks: erythro-1-Iba221: 4.20 (d, 1H), 1.26 (bs, 1H)
Ex. Iba235: Selected peaks: erythro-1-Iba235: 4.22 (d, 1H)
Ex. Iba242: Selected peaks: erythro-1-Iba242: 4.21 (d, 1H)
Ex. Iba275: Selected peaks: erythro-1-Iba275: 4.13 (d, 1H)
Ex. Iba289: Selected peaks: erythro-1-Iba289: 4.16 (d, 1H)
Ex. Iba327: Selected peaks: erythro-1-Iba327: 4.15 (d, 1H)
Ex. Iba354: erythro-1-Iba354: 7.29 (m, 3H), 7.00 (m, 3H), 6.84 (m, 2H), 4.16 (d, 1H), 3.69 (m, 1H), 3.48 (m, 1H), 3.30 (m, 1H), 2.09 (m, 2H), 1.26 (bs, 1H)
Ex. Iba370: erythro-1-Iba370: 7.29 (m, 3H), 7.00 (m, 3H), 6.84 (m, 2H), 4.16 (d, 1H), 3.69 (m, 1H), 3.48 (m, 1H), 3.30 (m, 1H), 2.09 (m, 2H), 1.26 (bs, 1H)
Ex. Iba376: Selected peaks: erythro-1-Iba376: 4.15 (d, 1H)
Ex. Iba532: Selected peaks: erythro-1-Iba532: 4.22 (d, 1H)
Ex. Iba937: erythro-1-Iba937: 7.27 (m, 3H), 7.06 (m, 3H), 6.83 (m, 2H), 4.15 (d, 1H), 3.69 (m, 1H), 3.50 (m, 1H), 3.25 (m, 1H), 2.11 (m, 2H), 1.31 (bs, 1H)

NMR data of optically active erythro-2 enantiomers of compounds according to the invention of Table 1, where in the compound in question $R^1$=H (accordingly, these compounds correspond to formula (Ia)):

$^1$H-NMR data (CDCl$_3$)-chemical shift of selected characteristic signals in ppm:

Ex. Iba1: erythro-2-Iba1: 7.34 (m, 6H), 6.95 (t, 2H), 4.23 (d, 1H), 3.81 (m, 1H), 3.49 (m, 1H), 3.33 (m, 1H), 1.98 (m, 1H), 1.78 (m, 1H), 1.15 (bs, 1H)
Ex. Iba3: Selected peaks: erythro-2-Iba3: 4.24 (d, 1H)
Ex. Iba5: erythro-2-Iba5: 7.32 (m, 5H), 6.95 (t, 2H), 4.22 (d, 1H), 3.80 (m, 1H), 3.51 (m, 1H), 3.33 (m, 1H), 2.01 (m, 1H), 1.78 (m, 1H), 1.18 (bs, 1H)
Ex. Iba19: erythro-2-Iba19: 7.22 (m, 4H), 6.94 (t, 2H), 4.22 (d, 1H), 3.79 (m, 1H), 3.54 (m, 1H), 3.46 (m, 1H), 2.03 (m, 1H), 1.78 (m, 1H), 1.27 (bs, 1H)
Ex. Iba24: erythro-2-Iba24: 7.62 (m, 2H), 7.32 (m, 2H), 6.97 (t, 2H), 4.32 (d, 1H), 3.82 (m, 1H), 3.61 (m, 1H), 3.41 (m, 1H), 2.01 (m, 1H), 1.82 (m, 1H)

Ex. Iba25: erythro-2-Iba25: 7.58 (m, 1H), 7.30 (m, 2H), 7.17 (m, 1H), 6.97 (t, 2H), 4.21 (d, 1H), 3.78 (m, 1H), 3.52 (m, 1H), 3.34 (m, 1H), 2.02 (m, 1H), 1.78 (m, 1H), 1.21 (bs, 1H)

Ex. Iba26: erythro-2-Iba26: 7.44 (m, 1H), 7.28 (m, 2H), 7.18 (m, 1H), 6.94 (t, 2H), 4.22 (d, 1H), 3.78 (m, 1H), 3.53 (m, 1H), 3.36 (m, 1H), 2.03 (m, 1H), 1.78 (m, 1H), 1.22 (bs, 1H)

Ex. Iba28: erythro-2-Iba28: 7.26 (m, 3H), 7.09 (m, 3H), 6.94 (m, 2H), 4.19 (d, 1H), 3.65 (m, 2H), 3.43 (m, 1H), 2.00 (m, 2H), 1.26 (bs, 1H)

Ex. Iba30: erythro-2-Iba30: 7.31 (m, 1H), 7.12 (m, 1H), 6.97 (m, 5H), 4.22 (d, 1H), 3.68 (m, 2H), 3.45 (m, 1H), 2.10 (m, 2H), 1.38 (bs, 1H)

Ex. Iba46: erythro-2-Iba46: 7.01 (m, 6H), 4.23 (d, 1H), 3.69 (m, 2H), 3.48 (m, 1H), 2.04 (m, 2H), 1.38 (bs, 1H)

Ex. Iba51: erythro-2-Iba51: 7.41 (m, 2H), 7.15 (m, 2H), 6.94 (m, 2H), 4.38 (d, 1H), 3.74 (m, 2H), 3.53 (m, 1H), 2.08 (m, 2H), 1.26 (bs, 1H)

Ex. Iba52: erythro-2-Iba52: 7.37 (m, 1H), 7.03 (m, 5H), 4.22 (d, 1H), 3.37 (m, 2H), 3.48 (m, 1H), 2.03 (m, 2H), 1.40 (bs, 1H)

Ex. Iba53: erythro-2-Iba53: 7.21 (m, 1H), 7.03 (m, 5H), 4.22 (d, 1H), 3.67 (m, 2H), 3.48 (m, 1H), 2.03 (m, 2H), 1.40 (bs, 1H)

Ex. Iba57: erythro-2-Iba57: 7.37 (m, 1H), 7.10 (m, 2H), 6.89 (m, 1H), 4.23 (d, 1H), 3.82 (m, 1H), 3.53 (m, 1H), 3.34 (m, 1H), 2.00 (m, 1H), 1.81 (m, 1H), 1.33 (bs, 1H)

Ex. Iba59: erythro-2-Iba59: 7.32 (m, 4H), 7.13 (m, 1H), 6.89 (m, 1H), 4.21 (d, 1H), 3.82 (m, 1H), 3.54 (m, 1H), 3.35 (m, 1H), 2.00 (m, 1H), 1.79 (m, 1H), 1.21 (bs, 1H)

Ex. Iba64: Selected peaks: erythro-2-Iba64: 4.23 (d, 1H)

Ex. Iba80: erythro-2-Iba80: 7.43 (m, 1H), 7.18 (m, 3H), 6.90 (m, 1H), 4.21 (d, 1H), 3.81 (m, 1H), 3.55 (m, 1H), 3.35 (m, 1H), 2.00 (m, 1H), 1.81 (m, 1H), 1.33 (bs, 1H)

Ex. Iba111: erythro-2-Iba111: 7.39 (m, 1H), 7.09 (m, 5H), 4.20 (d, 1H), 3.75 (m, 1H), 3.54 (m, 1H), 3.34 (m, 1H), 1.97 (m, 1H), 1.79 (m, 1H), 1.31 (bs, 1H)

Ex. Iba138: erythro-2-Iba138: 7.31 (m, 2H), 7.01 (m, 1H), 6.89 (m, 1H), 6.70 (m, 2H), 4.17 (d, 1H), 3.70 (m, 1H), 3.49 (m, 1H), 3.31 (m, 1H), 2.08 (m, 1H), 1.37 (bs, 1H)

Ex. Iba140: Selected peaks: erythro-2-Iba140: 4.14 (d, 1H)

Ex. Iba154: erythro-2-Iba154: 7.19 (m, 1H), 7.19 (t, 1H), 6.98 (m, 1H), 6.73 (m, 1H), 6.64 (m, 2H), 4.15 (d, 1H), 3.72 (m, 1H), 3.48 (m, 1H), 3.28 (m, 1H), 2.06 (m, 2H), 1.34 (bs, 1H)

Ex. Iba181: erythro-2-Iba181: 7.14 (m, 4H), 7.00 (m, 1H), 6.98 (m, 1H), 4.25 (d, 1H), 3.71 (m, 2H), 3.48 (m, 1H), 2.06 (m, 2H), 1.36 (bs, 1H)

Ex. Iba221: Selected peaks: erythro-2-Iba221: 4.20 (d, 1H), 1.26 (bs, 1H)

Ex. Iba235: Selected peaks: erythro-2-Iba235: 4.22 (d, 1H)

Ex. Iba242: Selected peaks: erythro-2-Iba242: 4.21 (d, 1H)

Ex. Iba275: Selected peaks: erythro-2-Iba275: 4.13 (d, 1H)

Ex. Iba289: Selected peaks: erythro-2-Iba289: 4.16 (d, 1H)

Ex. Iba327: Selected peaks: erythro-2-Iba327: 4.15 (d, 1H)

Ex. Iba354: erythro-2-Iba354: 7.29 (m, 3H), 7.00 (m, 3H), 6.84 (m, 2H), 4.16 (d, 1H), 3.69 (m, 1H), 3.48 (m, 1H), 3.30 (m, 1H), 2.09 (m, 2H), 1.26 (bs, 1H)

Ex. Iba370: erythro-2-Iba370: 7.29 (m, 3H), 7.00 (m, 3H), 6.84 (m, 2H), 4.16 (d, 1H), 3.69 (m, 1H), 3.48 (m, 1H), 3.30 (m, 1H), 2.09 (m, 2H), 1.26 (bs, 1H)

Ex. Iba376: Selected peaks: erythro-2-Iba376: 4.15 (d, 1H)

Ex. Iba532: Selected peaks: erythro-2-Iba532: 4.22 (d, 1H)

Ex. Iba937: erythro-2-Iba937: 7.27 (m, 3H), 7.06 (m, 3H), 6.83 (m, 2H), 4.15 (d, 1H), 3.69 (m, 1H), 3.50 (m, 1H), 3.25 (m, 1H), 2.11 (m, 2H), 1.31 (bs, 1H)

NMR data of optically active threo-1 enantiomers of compounds according to the invention of Table 1, where in the compound in question $R^1$=H (accordingly, these compounds correspond to formula (Ia)):

$^1$H-NMR data (CDCl$_3$)-chemical shift of selected characteristic signals in ppm:

Ex. Iba1: threo-1-Iba1: 7.17 (m, 5H), 7.06 (m, 1H), 6.71 (t, 2H), 4.19 (d, 1H), 3.87 (m, 1H), 3.79 (m, 1H), 3.48 (m, 1H), 2.53 (m, 1H), 2.28 (m, 1H), 1.32 (bs, 1H)

Ex. Iba3: threo-1-Iba3: 7.14 (m, 2H), 6.97 (m, 1H), 6.91 (m, 2H), 6.74 (t, 2H), 4.20 (d, 1H), 3.87 (m, 1H), 3.69 (m, 1H), 3.46 (m, 1H), 2.50 (m, 1H), 2.28 (m, 1H), 1.37 (bs, 1H)

Ex. Iba5: threo-1-Iba5: 7.12 (m, 5H), 6.75 (t, 2H), 4.18 (d, 1H), 3.87 (m, 1H), 3.69 (m, 1H), 3.47 (m, 1H), 2.49 (m, 1H), 2.37 (m, 1H), 1.48 (bs, 1H)

Ex. Iba10: threo-1-Iba10: 4.12 (d, 1H)

Ex. Iba19: threo-1-Iba19: 7.13 (m, 1H), 7.01 (m, 2H), 6.92 (m, 1H), 6.77 (t, 2H), 4.17 (d, 1H), 3.86 (m, 1H), 3.71 (m, 1H), 3.44 (m, 1H), 2.49 (m, 1H), 2.26 (m, 1H), 1.33 (bs, 1H)

Ex. Iba24: threo-1-Iba24: 7.49 (m, 5H), 7.08 (m, 2H), 6.79 (t, 2H), 4.23 (d, 1H), 3.88 (m, 1H), 3.72 (m, 1H), 3.44 (m, 1H), 2.50 (m, 1H), 2.27 (m, 1H)

Ex. Iba25: threo-1-Iba25: 7.61 (m, 1H), 7.1 (m, 3H), 6.77 (t, 2H), 4.17 (d, 1H), 3.82 (m, 1H), 3.71 (m, 1H), 3.44 (m, 1H), 2.48 (m, 1H), 2.27 (m, 1H), 1.29 (bs, 1H)

Ex. Iba26: threo-1-Iba26: 7.21 (m, 1H), 7.13 (m, 1H), 6.98 (m, 1H), 6.92 (m, 1H), 6.77 (t, 2H), 4.16 (d, 1H), 3.86 (m, 1H), 3.71 (m, 1H), 3.44 (m, 1H), 2.49 (m, 1H), 2.27 (m, 1H), 1.33 (bs, 1H)

Ex. Iba28: threo-1-Iba28: 7.28 (m, 5H), 6.92 (m, 3H), 4.10 (d, 1H), 3.63 (m, 2H), 3.38 (m, 1H), 2.20 (m, 2H), 1.29 (bs, 1H)

Ex. Iba30: threo-1-Iba30: 7.25 (m, 1H), 6.98 (m, 6H), 4.10 (d, 1H), 3.63 (m, 2H), 3.39 (m, 1H), 2.26 (m, 1H), 2.14 (m, 1H), 1.35 (bs, 1H)

Ex. Iba32: threo-1-Iba32: 7.24 (m, 3H), 7.14 (m, 1H), 6.94 (m, 3H), 4.08 (d, 1H), 3.64 (m, 2H), 3.38 (m, 1H), 2.19 (m, 2H), 1.35 (bs, 1H)

Ex. Iba37: threo-1-Iba37: 4.11 (d, 1H)

Ex. Iba46: threo-1-Iba46: 6.96 (m, 6H), 4.07 (d, 1H), 3.63 (m, 2H), 3.38 (m, 1H), 2.27 (m, 1H), 2.12 (m, 1H), 1.26 (bs, 1H)

Ex. Iba51: threo-1-Iba51: 7.48 (m, 2H), 7.18 (t, 1H), 6.93 (m, 3H), 4.13 (d, 1H), 3.64 (m, 2H), 3.39 (m, 1H), 2.28 (m, 1H), 2.17 (m, 1H), 1.26 (bs, 1H)

Ex. Iba52: threo-1-Iba52: 7.44 (m, 1H), 7.18 (m, 1H), 6.97 (m, 4H), 4.12 (d, 1H), 3.64 (m, 2H), 3.39 (m, 1H), 2.26 (m, 1H), 2.13 (m, 1H), 1.28 (bs, 1H)

Ex. Iba53: threo-1-Iba53: 7.31 (m, 1H), 6.95 (m, 5H), 4.07 (d, 1H), 3.62 (m, 2H), 3.40 (m, 1H), 2.26 (m, 1H), 2.12 (m, 1H), 1.40 (bs, 1H)

Ex. Iba55: threo-1-Iba55: 7.21 (m, 5H), 7.11 (m, 1H), 6.67 (m, 1H), 4.18 (d, 1H), 3.90 (m, 1H), 3.70 (m, 1H), 3.46 (m, 1H), 2.52 (m, 1H), 2.28 (m, 1H), 1.43 (bs, 1H)

Ex. Iba57: threo-1-Iba57: 7.12 (m, 1H), 6.94 (m, 4H), 6.71 (m, 1H), 4.18 (d, 1H), 3.91 (m, 1H), 3.72 (m, 1H), 3.46 (m, 1H), 2.51 (m, 1H), 2.26 (m, 1H), 1.41 (bs, 1H)

Ex. Iba59: threo-1-Iba59: 7.18 (m, 3H), 7.09 (m, 1H), 6.97 (m, 1H), 6.72 (m, 1H), 4.16 (d, 1H), 3.91 (m, 1H), 3.72 (m, 1H), 3.48 (m, 1H), 2.51 (m, 1H), 2.28 (m, 1H), 1.38 (bs, 1H)

Ex. Iba64: Selected peaks: threo-1-Iba64: 4.32 (d, 1H)

Ex. Iba73: threo-1-Iba73: 6.98 (m, 4H), 6.73 (m, 1H), 4.17 (d, 1H), 3.89 (m, 1H), 3.73 (m, 1H), 3.45 (m, 1H), 2.50 (m, 1H), 2.25 (m, 1H), 1.39 (bs, 1H)

Ex. Iba79: threo-1-Iba79: 7.39 (m, 1H), 7.12 (m, 1H), 6.99 (m, 2H), 6.74 (m, 1H), 4.15 (d, 1H), 3.88 (m, 1H), 3.72 (m, 1H), 3.45 (m, 1H), 2.50 (m, 1H), 2.26 (m, 1H), 1.42 (bs, 1H)

Ex. Iba80: threo-1-Iba80: 7.24 (m, 1H), 7.02 (m, 3H), 6.72 (m, 1H), 4.15 (d, 1H), 3.88 (m, 1H), 3.72 (m, 1H), 3.44 (m, 1H), 2.51 (m, 1H), 2.25 (m, 1H), 1.46 (bs, 1H)

Ex. Iba84: threo-1-Iba84: 7.22 (m, 1H), 6.94 (m, 3H), 6.53 (m, 2H), 4.14 (d, 1H), 3.83 (m, 1H), 3.70 (m, 1H), 3.45 (m, 1H), 2.47 (m, 1H), 2.24 (m, 1H), 1.39 (bs, 1H)

Ex. Iba86: threo-1-Iba86: 7.19 (m, 3H), 7.06 (m, 1H), 6.54 (m, 2H), 4.11 (d, 1H), 3.83 (m, 1H), 3.70 (m, 1H), 3.45 (m, 1H), 2.47 (m, 1H), 2.24 (m, 1H), 1.36 (bs, 1H)

Ex. Iba100: threo-1-Iba100: 7.03 (m, 2H), 6.90 (m, 1H), 6.55 (m, 2H), 4.11 (d, 1H), 3.81 (m, 1H), 3.71 (m, 1H), 3.44 (m, 1H), 2.47 (m, 1H), 2.23 (m, 1H), 1.40 (bs, 1H)

Ex. Iba107: threo-1-Iba107: 7.24 (m, 1H), 7.03 (m, 2H), 6.56 (m, 2H), 4.11 (d, 1H), 3.81 (m, 1H), 3.71 (m, 1H), 3.45 (m, 1H), 2.47 (m, 1H), 2.23 (m, 1H), 1.34 (bs, 1H)

Ex. Iba111: threo-1-Iba111: 7.22 (m, 1H), 6.95 (m, 3H), 6.80 (m, 2H), 4.14 (d, 1H), 3.86 (m, 1H), 3.71 (m, 1H), 3.45 (m, 1H), 2.48 (m, 1H), 2.23 (m, 1H), 1.34 (bs, 1H)

Ex. Iba113: threo-1-Iba113: 7.19 (m, 3H), 7.05 (m, 1H), 6.81 (m, 2H), 4.12 (d, 1H), 3.84 (m, 1H), 3.71 (m, 1H), 3.44 (m, 1H), 2.47 (m, 1H), 2.23 (m, 1H), 1.41 (bs, 1H)

Ex. Iba127: threo-1-Iba127: 7.04 (m, 2H), 6.90 (m, 1H), 6.82 (m, 2H), 4.12 (d, 1H), 3.83 (m, 1H), 3.71 (m, 1H), 3.44 (m, 1H), 2.46 (m, 1H), 2.23 (m, 1H), 1.37 (bs, 1H)

Ex. Iba134: threo-1-Iba134: 7.25 (m, 1H), 7.03 (m, 2H), 6.83 (m, 2H), 4.12 (d, 1H), 3.84 (m, 1H), 3.72 (m, 1H), 3.44 (m, 1H), 2.47 (m, 1H), 2.22 (m, 1H), 1.43 (bs, 1H)

Ex. Iba138: threo-1-Iba138: 7.31 (m, 2H), 6.98 (m, 2H), 6.71 (m, 3H), 3.98 (d, 1H), 3.64 (m, 1H), 3.33 (m, 2H), 2.25 (m, 1H), 2.04 (m, 1H), 1.28 (bs, 1H)

Ex. Iba140: Selected peaks: threo-1-Iba140: 3.97 (d, 1H)

Ex. Iba154: threo-1-Iba154: 7.25 (m, 2H), 7.05 (m, 2H), 6.70 (m, 2H), 3.96 (d, 1H), 3.66 (m, 1H), 3.33 (m, 2H), 2.25 (m, 1H), 2.02 (m, 1H), 1.33 (bs, 1H)

Ex. Iba160: threo-1-Iba160: 7.40 (m, 2H), 7.07 (m, 2H), 6.69 (m, 2H), 3.96 (d, 1H), 3.66 (m, 1H), 3.32 (m, 2H), 2.24 (m, 1H), 2.02 (m, 1H), 1.26 (bs, 1H)

Ex. Iba161: threo-1-Iba161: 7.25 (m, 1H), 7.05 (m, 2H), 6.69 (m, 3H), 3.96 (d, 1H), 3.67 (m, 1H), 3.33 (m, 2H), 2.24 (m, 1H), 2.01 (m, 1H), 1.26 (bs, 1H)

Ex. Iba165: threo-1-Iba165: 7.27 (m, 1H), 7.02 (m, 6H), 4.11 (d, 1H), 3.66 (m, 2H), 3.37 (m, 1H), 2.21 (m, 2H), 1.33 (bs, 1H)

Ex. Iba181: threo-1-Iba181: 7.00 (m, 6H), 4.08 (d, 1H), 3.66 (m, 2H), 3.48 (m, 1H), 2.29 (m, 1H), 2.16 (m, 1H), 1.26 (bs, 1H)

Ex. Iba187: threo-1-Iba187: 7.45 (m, 1H), 7.09 (m, 4H), 6.92 (m, 1H), 4.08 (d, 1H), 3.65 (m, 2H), 3.38 (m, 1H), 2.22 (m, 1H), 1.38 (bs, 1H)

Ex. Iba188: threo-1-Iba188: 7.28 (m, 1H), 7.06 (m, 4H), 6.92 (m, 1H), 4.07 (d, 1H), 3.66 (m, 2H), 3.38 (m, 1H), 2.22 (m, 1H), 1.38 (bs, 1H)

Ex. Iba192: threo-1-Iba192: 7.28 (m, 1H), 6.99 (m, 6H), 3.97 (d, 1H), 3.63 (m, 1H), 3.33 (m, 2H), 2.24 (m, 1H), 2.02 (m, 1H), 1.23 (bs, 1H)

Ex. Iba208: threo-1-Iba208: 7.48 (m, 6H), 3.95 (d, 1H), 3.65 (m, 1H), 3.33 (m, 2H), 2.24 (m, 1H), 2.00 (m, 1H), 1.29 (bs, 1H)

Ex. Iba214: threo-1-Iba214: 7.26 (m, 1H), 7.10 (m, 2H), 6.96 (m, 1H), 6.84 (m, 1H), 3.95 (d, 1H), 3.65 (m, 1H), 3.33 (m, 2H), 2.22 (m, 1H), 2.00 (m, 1H), 1.28 (bs, 1H)

Ex. Iba215: threo-1-Iba215: 7.38 (m, 1H), 7.08 (m, 3H), 6.96 (m, 1H), 6.84 (m, 1H), 3.95 (d, 1H), 3.65 (m, 1H), 3.33 (m, 2H), 2.23 (m, 1H), 2.00 (m, 1H), 1.33 (bs, 1H)

Ex. Iba221: Selected peaks: threo-1-Iba221: 4.10 (d, 1H), 1.19 (bs, 1H)

Ex. Iba235: threo-1-Iba235: 7.42 (m, 1H), 7.24 (m, 2H), 7.08 (m, 4H), 4.08 (d, 1H), 3.61 (m, 2H), 3.38 (m, 1H), 2.23 (m, 2H), 1.33 (bs, 1H)

Ex. Iba241: threo-1-Iba241: 7.42 (m, 1H), 7.24 (m, 1H), 7.08 (m, 5H), 4.08 (d, 1H), 3.61 (m, 2H), 3.38 (m, 1H), 2.21 (m, 2H), 1.34 (bs, 1H)

Ex. Iba242: threo-1-Iba242: 7.15 (m, 7H), 4.08 (d, 1H), 3.63 (m, 2H), 3.39 (m, 1H), 2.23 (m, 2H), 1.38 (bs, 1H)

Ex. Iba275: Selected peaks: threo-1-Iba275: 3.97 (d, 1H)

Ex. Iba289: Selected peaks: threo-1-Iba289: 3.71 (d, 1H)

Ex. Iba327: Selected peaks: threo-1-Iba327: 3.97 (d, 1H)

Ex. Iba354: threo-1-Iba354: 7.28 (m, 3H), 6.98 (m, 5H), 3.98 (d, 1H), 3.61 (m, 1H), 3.31 (m, 2H), 2.23 (m, 1H), 2.07 (m, 1H), 1.23 (bs, 1H)

Ex. Iba370: threo-1-Iba370: 7.28 (m, 3H), 6.98 (m, 5H), 3.98 (d, 1H), 3.61 (m, 1H), 3.31 (m, 2H), 2.23 (m, 1H), 2.07 (m, 1H), 1.23 (bs, 1H)

Ex. Iba376: Selected peaks: threo-1-Iba376: 3.94 (d, 1H)

Ex. Iba532: Selected peaks: threo-1-Iba532: 4.05 (d, 1H)

Ex. Iba539: threo-1-Iba539: 7.28 (m, 1H), 7.09 (m, 3H), 6.80 (m, 2H), 4.05 (d, 1H), 4.62 (m, 2H), 3.37 (m, 1H), 2.20 (m, 2H), 1.27 (bs, 1H)

Ex. Iba937: threo-1-Iba937: 7.28 (m, 3H), 6.98 (m, 5H), 3.96 (d, 1H), 3.61 (m, 1H), 3.39 (m, 1H), 3.26 (m, 1H), 2.28 (m, 1H), 2.11 (m, 1H), 1.23 (bs, 1H)

Ex. Iba1085: threo-1-Iba1085: 7.26 (m, 2H), 7.04 (m, 1H), 6.79 (m, 2H), 3.95 (d, 1H), 3.65 (m, 1H), 3.33 (m, 2H), 2.21 (m, 1H), 1.97 (m, 1H), 1.31 (bs, 1H)

Ex. Iba1099: threo-1-Iba1099: 7.08 (m, 2H), 6.89 (m, 1H), 6.77 (m, 2H), 3.98 (d, 1H), 3.65 (m, 1H), 3.32 (m, 1H), 3.26 (m, 1H), 2.23 (m, 1H), 1.96 (m, 1H), 1.32 (bs, 1H)

Ex. Iba1106: threo-1-Iba1106: 7.27 (m, 1H), 7.07 (m, 2H), 6.78 (m, 2H), 3.96 (d, 1H), 3.67 (m, 1H), 3.32 (m, 2H), 2.21 (m, 1H), 1.96 (m, 1H), 1.33 (bs, 1H)

NMR data of optically active threo-2 enantiomers of compounds according to the invention of Table 1, where in the compound in question $R^1$=H (accordingly, these compounds correspond to formula (Ia)):

$^1$H-NMR data (CDCl$_3$)-chemical shift of selected characteristic signals in ppm:

Ex. Iba1: threo-2-Iba1: 7.17 (m, 5H), 7.06 (m, 1H), 6.71 (t, 2H), 4.19 (d, 1H), 3.87 (m, 1H), 3.79 (m, 1H), 3.48 (m, 1H), 2.53 (m, 1H), 2.28 (m, 1H), 1.32 (bs, 1H)

Ex. Iba5: threo-2-Iba5: 7.12 (m, 5H), 6.75 (t, 2H), 4.18 (d, 1H), 3.87 (m, 1H), 3.69 (m, 1H), 3.47 (m, 1H), 2.49 (m, 1H), 2.37 (m, 1H), 1.48 (bs, 1H)

Ex. Iba19: threo-2-Iba19: 7.13 (m, 1H), 7.01 (m, 2H), 6.92 (m, 1H), 6.77 (t, 2H), 4.17 (d, 1H), 3.86 (m, 1H), 3.71 (m, 1H), 3.44 (m, 1H), 2.49 (m, 1H), 2.26 (m, 1H), 1.39 (bs, 1H)

Ex. Iba24: threo-2-Iba24: 7.49 (m, 5H), 7.08 (m, 2H), 6.79 (t, 2H), 4.23 (d, 1H), 3.88 (m, 1H), 3.72 (m, 1H), 3.44 (m, 1H), 2.50 (m, 1H), 2.27 (m, 1H)

Ex. Iba25: threo-2-Iba25: 7.61 (m, 1H), 7.1 (m, 3H), 6.67 (t, 2H), 4.17 (d, 1H), 3.82 (m, 1H), 3.71 (m, 1H), 3.44 (m, 1H), 2.48 (m, 1H), 2.27 (m, 1H), 1.29 (bs, 1H)

Ex. Iba26: threo-2-Iba26: 7.21 (m, 1H), 7.13 (m, 1H), 6.98 (m, 1H), 6.92 (m, 1H), 6.77 (t, 2H), 4.16 (d, 1H), 3.86 (m, 1H), 3.71 (m, 1H), 3.44 (m, 1H), 2.49 (m, 1H), 2.27 (m, 1H), 1.33 (bs, 1H)

Ex. Iba30: threo-2-Iba30: 7.25 (m, 1H), 6.98 (m, 6H), 4.10 (d, 1H), 3.63 (m, 2H), 3.39 (m, 1H), 2.26 (m, 1H), 2.14 (m, 1H), 1.35 (bs, 1H)

Ex. Iba46: threo-2-Iba46: 6.96 (m, 6H), 4.07 (d, 1H), 3.63 (m, 2H), 3.38 (m, 1H), 2.27 (m, 1H), 2.12 (m, 1H), 1.26 (bs, 1H)

Ex. Iba51: threo-2-Iba51: 7.48 (m, 2H), 7.18 (t, 1H), 6.93 (m, 3H), 4.13 (d, 1H), 3.64 (m, 2H), 3.39 (m, 1H), 2.28 (m, 1H), 2.17 (m, 1H), 1.26 (bs, 1H)

Ex. Iba52: threo-2-Iba52: 7.44 (m, 1H), 7.18 (m, 1H), 6.97 (m, 4H), 4.12 (d, 1H), 3.64 (m, 2H), 3.39 (m, 1H), 2.26 (m, 1H), 2.13 (m, 1H), 1.28 (bs, 1H)

Ex. Iba53: threo-2-Iba53: 7.31 (m, 1H), 6.95 (m, 5H), 4.07 (d, 1H), 3.62 (m, 2H), 3.40 (m, 1H), 2.26 (m, 1H), 2.12 (m, 1H), 1.40 (bs, 1H)

Ex. Iba57: threo-2-Iba57: 7.12 (m, 1H), 6.94 (m, 4H), 6.71 (m, 1H), 4.18 (d, 1H), 3.91 (m, 1H), 3.72 (m, 1H), 3.46 (m, 1H), 2.51 (m, 1H), 2.26 (m, 1H), 1.41 (bs, 1H)

Ex. Iba59: threo-2-Iba59: 7.18 (m, 3H), 7.09 (m, 1H), 6.97 (m, 1H), 6.72 (m, 1H), 4.16 (d, 1H), 3.91 (m, 1H), 3.72 (m, 1H), 3.48 (m, 1H), 2.51 (m, 1H), 2.28 (m, 1H), 1.38 (bs, 1H)

Ex. Iba64: Selected peaks: threo-2-Iba64: 4.32 (d, 1H)

Ex. Iba73: threo-2-Iba73: 6.98 (m, 4H), 6.73 (m, 1H), 4.17 (d, 1H), 3.89 (m, 1H), 3.73 (m, 1H), 3.45 (m, 1H), 2.50 (m, 1H), 2.25 (m, 1H), 1.39 (bs, 1H)

Ex. Iba80: threo-2-Iba80: 7.24 (m, 1H), 7.02 (m, 3H), 6.72 (m, 1H), 4.15 (d, 1H), 3.88 (m, 1H), 3.72 (m, 1H), 3.44 (m, 1H), 2.51 (m, 1H), 2.25 (m, 1H), 1.46 (bs, 1H)

Ex. Iba127: threo-2-Iba127: 7.04 (m, 2H), 6.90 (m, 1H), 6.82 (m, 2H), 4.12 (d, 1H), 3.83 (m, 1H), 3.71 (m, 1H), 3.44 (m, 1H), 2.46 (m, 1H), 2.23 (m, 1H), 1.37 (bs, 1H)

Ex. Iba138: threo-2-Iba138: 7.31 (m, 2H), 6.98 (m, 2H), 6.71 (m, 3H), 3.98 (d, 1H), 3.64 (m, 1H), 3.33 (m, 2H), 2.25 (m, 1H), 2.04 (m, 1H), 1.28 (bs, 1H)

Ex. Iba140: Selected peaks: threo-2-Iba140: 3.97 (d, 1H)

Ex. Iba154: threo-2-Iba154: 7.25 (m, 2H), 7.05 (m, 2H), 6.70 (m, 2H), 3.96 (d, 1H), 3.66 (m, 1H), 3.33 (m, 2H), 2.25 (m, 1H), 2.02 (m, 1H), 1.33 (bs, 1H)

Ex. Iba181: threo-2-Iba181: 7.00 (m, 6H), 4.08 (d, 1H), 3.66 (m, 2H), 3.48 (m, 1H), 2.29 (m, 1H), 2.16 (m, 1H), 1.26 (bs, 1H)

Ex. Iba221: Selected peaks: threo-2-Iba221: 4.10 (d, 1H), 1.19 (bs, 1H)

Ex. Iba235: Selected peaks: threo-2-Iba235: 4.08 (d, 1H)

Ex. Iba241: threo-2-Iba241: 7.42 (m, 1H), 7.24 (m, 1H), 7.08 (m, 5H), 4.08 (d, 1H), 3.61 (m, 2H), 3.38 (m, 1H), 2.21 (m, 2H), 1.34 (bs, 1H)

Ex. Iba242: Selected peaks: threo-2-Iba242: 4.08 (d, 1H)

Ex. Iba275: Selected peaks: threo-2-Iba275: 3.97 (d, 1H)

Ex. Iba289: Selected peaks: threo-2-Iba289: 3.71 (d, 1H)

Ex. Iba327: Selected peaks: threo-2-Iba327: 3.97 (d, 1H)

Ex. Iba354: threo-2-Iba354: 7.28 (m, 3H), 6.98 (m, 5H), 3.98 (d, 1H), 3.61 (m, 1H), 3.31 (m, 2H), 2.23 (m, 1H), 2.07 (m, 1H), 1.23 (bs, 1H)

Ex. Iba370: threo-2-Iba370: 7.28 (m, 3H), 6.98 (m, 5H), 3.98 (d, 1H), 3.61 (m, 1H), 3.31 (m, 2H), 2.23 (m, 1H), 2.07 (m, 1H), 1.23 (bs, 1H)

Ex. Iba376: Selected peaks: threo-2-Iba376: 3.94 (d, 1H)

Ex. Iba532: Selected peaks: threo-2-Iba532: 4.05 (d, 1H)

Ex. Iba937: threo-2-Iba937: 7.28 (m, 3H), 6.98 (m, 5H), 3.96 (d, 1H), 3.61 (m, 1H), 3.39 (m, 1H), 3.26 (m, 1H), 2.28 (m, 1H), 2.11 (m, 1H), 1.23 (bs, 1H)

Ex. Iba1085: threo-2-Iba1085: 7.26 (m, 2H), 7.04 (m, 1H), 6.79 (m, 2H), 3.95 (d, 1H), 3.65 (m, 1H), 3.33 (m, 2H), 2.21 (m, 1H), 1.97 (m, 1H), 1.31 (bs, 1H)

Ex. Iba1099: threo-2-Iba1099: 7.08 (m, 2H), 6.89 (m, 1H), 6.77 (m, 2H), 3.98 (d, 1H), 3.65 (m, 1H), 3.32 (m, 1H), 3.26 (m, 1H), 2.23 (m, 1H), 1.96 (m, 1H), 1.32 (bs, 1H)

The retention time (Rt) given in the Rt table below for the enantiomer of the formula (I) in question is given in minutes (min), where the letter a, b, c or d given after the forward slash after the retention time refers to the conditions stated above for HPLC on a chiral column and the respective mobile phase stated above, i.e. mobile phase a, mobile phase b, mobile phase c or mobile phase d.

Rt Table: Rt in min, where $R^1$ is in each case hydrogen

| No. | $(R^2)_n$ | $(R^3)_m$ | Erythro-1 | Erythro-2 | Threo-1 | Threo-2 |
|---|---|---|---|---|---|---|
| Iba1 | H | 2,6-$F_2$ | 7.476/c | 8.054/c | 10.392/c | 13.798/c |
| Iba3 | 3-F | 2,6-$F_2$ | 6.507/c | 7.361/c | 8.617/c | 11.606/c |
| Iba6 | 3-Cl | 2,6-$F_2$ | 19.817/d | 24.384/d | 30.260/d | 41.660/d |
| Iba19 | 3,4-$F_2$ | 2,6-$F_2$ | 16.500/d | 16.500/d | 21.145/d | 28.346/d |
| Iba24 | 3-CN, 4-F | 2,6-$F_2$ | 5.776/a | 5.776/a | 6.983/a | 10.502/a |
| Iba26 | 3-Cl, 4-F | 2,6-$F_2$ | 6.086/c | 6.823/c | 8.083/c | 10.503/c |
| Iba28 | H | 2,5-$F_2$ | 6.297/c | 7.251/c | 11.084/c | 14.822/c |
| Iba30 | 3-F | 2,5-$F_2$ | 5.460/c | 6.275/c | 9.294/c | 12.691/c |
| Iba32 | 3-Cl | 2,5-$F_2$ | 15.567/d | 19.423/d | 33.717/d | 46.942/d |
| Iba46 | 3,4-$F_2$ | 2,5-$F_2$ | 12.918/d | 14.505d | 27.961/d | 27.235/d |
| Iba51 | 3-CN, 4-F | 2,5-$F_2$ | 11.887/a | 12.481/a | 18.760/a | 25.953/a |
| Iba52 | 3-Br, 4-F | 2,5-$F_2$ | 13.686/d | 15.902/d | 31.289/d | 39.488/d |
| Iba53 | 3-Cl, 4-F | 2,5-$F_2$ | 4.813/c | 5.270/c | 8.201/c | 10.137/c |
| Iba55 | H | 2,3,6-$F_3$ | 23.055/d | 25.088/d | 32.028/d | 46.823/d |
| Iba57 | 3-F | 2,3,6-$F_3$ | 6.200/c | 6.397/c | 7.573/c | 10.118/c |
| Iba59 | 3-Cl | 2,3,6-$F_3$ | 6.117/c | 6.399/c | 7.730/c | 10.016/c |
| Iba73 | 3,4-$F_2$ | 2,3,6-$F_3$ | 11.118/d | 18.107/d | 23.703/d | 35.888/d |
| Iba79 | 3-Br, 4-F | 2,3,6-$F_3$ | 5.868/c | 6.153/c | 7.544/c | 9.723/c |
| Iba80 | 3-Cl, 4-F | 2,3,6-$F_3$ | 18.046/d | 19.021/d | 24.630/d | 36.073/d |
| Iba84 | 3-F | 2,4,6-$F_3$ | 9.595/d | 12.235/d | 14.472/d | 21.439/d |
| Iba86 | 3-Cl | 2,4,6-$F_3$ | 9.562/d | 12.348/d | 15.207/d | 21.224/d |
| Iba100 | 3,4-$F_2$ | 2,4,6-$F_3$ | 9.224/d | 10.526/d | 13.187/d | 19.133/d |
| Iba106 | 3-Br, 4-F | 2,4,6-$F_3$ | 9.650/d | 11.955/d | 14.874/d | 20.462/d |
| Iba107 | 3-Cl, 4-F | 2,4,6-$F_3$ | 9.063/d | 11.065/d | 13.694/d | 19.109/d |
| Iba111 | 3-F | 2,6-$F_2$, 4-Cl | 9.925/d | 12.409/d | 14.469/d | 21.258/d |
| Iba113 | 3-Cl | 2,6-$F_2$, 4-Cl | 9.674/d | 12.190/d | 14.844/d | 20.403/d |
| Iba127 | 3,4-$F_2$ | 2,6-$F_2$, 4-Cl | 14.868/d | 16.295/d | 20.601/d | 29.289/d |

Rt Table: Rt in min, where R¹ is in each case hydrogen

| No. | $(R^2)_n$ | $(R^3)_m$ | Erythro-1 | Erythro-2 | Threo-1 | Threo-2 |
|---|---|---|---|---|---|---|
| Iba134 | 3-Cl, 4-F | 2,6-F$_2$, 4-Cl | 9.341/d | 11.216/d | 13.820/d | 19.074/d |
| Iba138 | 3-F | 3,5-F$_2$ | 13.289/d | 15.016/d | 24.010/d | 41.543/d |
| Iba154 | 3,4-F$_2$ | 3,5-F$_2$ | 11.888/d | 11.888/d | 21.854/d | 34.009/d |
| Iba160 | 3-Br, 4-F | 3,5-F$_2$ | 12.623/d | 12.623/d | 23.102/d | 34.922/d |
| Iba161 | 3-Cl, 4-F | 3,5-F$_2$ | 11.941/d | 11.941/d | 21.716/d | 33.373/d |
| Iba165 | 3-F | 2,3-F$_2$ | 6.907/c | 6.907/c | 9.238/c | 16.639/c |
| Iba181 | 3,4-F$_2$ | 2,3-F$_2$ | 5.068/c | 5.068/c | 7.206/c | 11.296/c |
| Iba187 | 3-Br, 4-F | 2,3-F$_2$ | 5.299/c | 5.299/c | 7.772/c | 12.775/c |
| Iba188 | 3-Cl, 4-F | 2,3-F$_2$ | 5.171/c | 5.171/c | 7.516/c | 12.248/c |
| Iba192 | 3-F | 3,4-F$_2$ | 4.947/c | 5.376/c | 7.481/c | 11.262/c |
| Iba208 | 3,4-F$_2$ | 3,4-F$_2$ | 12.120/d | 12.120/d | 23.669/d | 35.140/d |
| Iba214 | 3-Br, 4-F | 3,4-F$_2$ | 12.844/d | 12.844/d | 24.815/d | 36.469/d |
| Iba215 | 3-Cl, 4-F | 3,4-F$_2$ | 4.635/c | 4.635/c | 6.795/c | 9.101/c |
| Iba235 | 3,4-F$_2$ | 2-F | 5.445/c | 5.628/c | 8.234/c | 12.384/c |
| Iba241 | 3-Br, 4-F | 2-F | 5.652/c | 6.031/c | 9.020/c | 13.684/c |
| Iba242 | 3-Cl, 4-F | 2-F | 5.494/c | 5.817/c | 8.489/c | 12.741/c |
| Iba354 | 3-F | 4-Cl | 5.415/c | 5.932/c | 15.034/d | 17.607/d |
| Iba937 | 3,4-F$_2$ | H | 7.476/c | 7.476/c | 13.864/c | 21.153/c |
| Iba1085 | 3-Cl | 3,4,5-F$_3$ | 6.909/d | 7.598/d | 12.110/d | 20.648/d |
| Iba1099 | 3,4-F$_2$ | 3,4,5-F$_3$ | 6.130/d | 6.630/d | 10.715/d | 16.107/d |
| Iba1106 | 3-Cl, 4-F | 3,4,5-F$_3$ | 9.910/d | 9.910/d | 16.983/d | 25.080/d |

NMR data of an optically active erythro-1 enantiomer according to the invention, where in this compound R¹ is not H (this compound corresponds to formula (erythro-1-Ib)):
Ex. Ibg26: Selected peaks: erythro-1-Ibg26: 6.96 (t, 2H)

NMR data of optically active erythro-2 enantiomers according to the invention, where in the compound in question R¹ is not H (these compounds correspond to formula (erythro-2-Ib)):
Ex. Ibh19: Selected peaks: erythro-2-Ibh19: 6.95 (t, 2H)
Ex. Ibv19: Selected peaks: erythro-2-Ibv19: 6.95 (t, 2H), 1.12 (s, 9H)
Ex. Ibah19: Selected peaks: erythro-2-Ibah19: 6.95 (t, 2H), 4.19 (d, 1H), 3.74 (s, 2H), 3.28 (s, 3H)
Ex. Ibg26: Selected peaks: erythro-2-Ibg26: 6.96 (t, 2H)
Ex. Ibo46: Selected peaks: erythro-2-Ibo46: 4.21 (d, 1H)
Ex. Ibaf46: Selected peaks: erythro-2-Ibaf46: 4.23 (d, 1H)
Ex. Ibah73: Selected peaks: erythro-2-Ibah73: 3.75 (s, 3H), 3.29 (s, 2H)
Ex. Ibb100: Selected peaks: erythro-2-Ibb100: 4.16 (d, 1H)
Ex. Ibag325: Selected peaks: erythro-2-Ibag325: 4.20 (d, 1H), 3.90 (s, 3H)
Ex. Ibah325: Selected peaks: erythro-2-Ibah325: 4.21 (d, 1H), 3.76 (s, 3H)

NMR data of optically active threo-1 enantiomers according to the invention, where in the compound in question R¹ is not H (these compounds correspond to formula (threo-1-Ib)):
Ex. Ibb19: threo-1-Ibb19: 7.15 (m, 1H), 7.00 (m, 2H), 6.91 (m, 1H), 6.76 (t, 2H), 4.14 (d, 1H), 4.06 (m, 1H), 3.82 (m, 2H), 2.59 (m, 1H), 2.35 (m, 1H), 1.97 (s, 3H)
Ex. Ibh19: Selected peaks: threo-1-Ibh19: 6.77 (t, 2H)
Ex. Ibo19: Selected peaks: threo-1-Ibo19: 6.73 (t, 2H)
Ex. Ibv19: Selected peaks: threo-1-Ibv19: 6.74 (t, 2H), 1.17 (s, 9H)
Ex. Ibab19: Selected peaks: threo-1-Ibab19: 6.77 (t, 2H), 4.16 (d, 1H), 3.99 (s, 2H)
Ex. Ibac19: Selected peaks: threo-1-Ibac19: 6.78 (t, 2H), 4.15 (d, 1H), 3.75 (s, 2H)
Ex. Ibad19: Selected peaks: threo-1-Ibad19: 6.78 (t, 2H), 4.16 (d, 1H), 5.86 (s, 1H)
Ex. Ibae19: Selected peaks: threo-1-Ibae19: 6.78 (t, 2H), 4.15 (d, 1H), 3.95 (s, 2H), 3.42 (s, 3H)
Ex. Ibah19: Selected peaks: threo-1-Ibah19: 6.77 (t, 2H), 4.16 (d, 1H), 3.76 (s, 3H), 3.32 (s, 2H)
Ex. Ibg26: Selected peaks: threo-1-Ibg26: 6.77 (t, 2H)
Ex. Ibac26: Selected peaks: threo-1-Ibac26: 6.78 (t, 2H), 4.14 (d, 1H), 3.75 (s, 2H)
Ex. Ibad26: Selected peaks: threo-1-Ibad26: 6.79 (t, 2H), 4.15 (d, 1H), 5.86 (s, 1H)
Ex. Ibag26: Selected peaks: threo-1-Ibag26: 6.78 (t, 2H), 4.16 (d, 1H), 3.85 (s, 3H)
Ex. Ibah26: Selected peaks: threo-1-Ibah26: 6.77 (t, 2H), 4.15 (d, 1H), 3.76 (s, 3H)
Ex. Ibo46: Selected peaks: threo-1-Ibo46: 4.06 (d, 1H)
Ex. Ibs46: Selected peaks: threo-1-Ibs46: 4.05 (d, 1H)
Ex. Ibab46: Selected peaks: threo-1-Ibab46: 4.04 (d, 1H), 3.96 (s, 2H)
Ex. Ibac46: Selected peaks: threo-1-Ibac46: 4.05 (d, 1H), 3.74 (s, 2H)
Ex. Ibad46: Selected peaks: threo-1-Ibad46: 4.05 (d, 1H), 5.86 (s, 1H)
Ex. Ibaf46: Selected peaks: threo-1-Ibaf46: 4.09 (d, 1H)
Ex. Ibad53: Selected peaks: threo-1-Ibad53: 4.05 (d, 1H), 5.86 (s, 1H)
Ex. Ibab73: Selected peaks: threo-1-Ibab73: 4.15 (d, 1H), 4.00 (s, 2H)
Ex. Ibaf73: Selected peaks: threo-1-Ibaf73: 4.15 (d, 1H)
Ex. Ibag73: Selected peaks: threo-1-Ibag73: 4.15 (d, 1H), 3.89 (s, 3H)
Ex. Ibah73: Selected peaks: threo-1-Ibah73: 4.15 (d, 1H), 3.76 (s, 3H), 3.34 (s, 2H)
Ex. Ibb100: Selected peaks: threo-1-Ibb100: 4.10 (d, 1H)
Ex. Ibg235: Selected peaks: threo-1-Ibg235: 4.07 (d, 1H)
Ex. Ibag325: Selected peaks: threo-1-Ibag325: 4.09 (d, 1H), 3.89 (s, 3H)
Ex. Ibah325: Selected peaks: threo-1-Ibah325: 4.07 (d, 1H), 3.76 (s, 3H)

NMR data of optically active threo-2 enantiomers according to the invention, where in the compound in question R¹ is not H (these compounds correspond to formula (threo-2-Ib)):
Ex. Ibb19: threo-2-Ibb19: 7.15 (m, 1H), 7.00 (m, 2H), 6.91 (m, 1H), 6.76 (t, 2H), 4.14 (d, 1H), 4.06 (m, 1H), 3.82 (m, 2H), 2.59 (m, 1H), 2.35 (m, 1H), 1.97 (s, 3H)

Ex. Ibab19: Selected peaks: threo-2-Ibab19: 6.77 (t, 2H), 4.16 (d, 1H), 3.99 (s, 2H)
Ex. Ibg26: Selected peaks: threo-2-Ibg26: 6.77 (t, 2H)
Ex. Ibo46: Selected peaks: threo-2-Ibo46: 4.06 (d, 1H)
Ex. Ibs46: Selected peaks: threo-2-Ibs46: 4.05 (d, 1H)
Ex. Ibab46: Selected peaks: threo-2-Ibab46: 4.04 (d, 1H), 3.96 (s, 2H)
Ex. Ibad53: Selected peaks: threo-2-Ibad53: 4.05 (d, 1H), 5.86 (s, 1H)
Ex. Ibab73: Selected peaks: threo-2-Ibab73: 4.15 (d, 1H), 4.00 (s, 2H)
Ex. Ibg235: Selected peaks: threo-2-Ibg235: 4.07 (d, 1H)

FORMULATION EXAMPLES a) A dust is obtained by mixing 10 parts by weight of a compound of the formula (I) and 90 parts by weight of talc as inert substance and comminuting the mixture in a hammer mill.
b) A wettable powder which is readily dispersible in water is obtained by mixing 25 parts by weight of a compound of the formula (I), 64 parts by weight of kaolin-containing quartz as inert substance, 10 parts by weight of potassium lignosulphonate and 1 part by weight of sodium oleoylmethyltaurate as wetting agent and dispersant, and grinding the mixture in a pinned-disk mill
c) A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to about 277° C.) and grinding the mixture in a ball mill to a fineness of below 5 microns.
d) An emulsifiable concentrate is obtained from 15 parts by weight of a compound of the formula (I), 75 parts by weight of cyclohexanone as solvent and 10 parts by weight of oxyethylated nonylphenol as emulsifier.
e) Water-dispersible granules are obtained by mixing 75 parts by weight of a compound of the formula (I),
10 parts by weight of calcium lignosulphonate,
5 parts by weight of sodium lauryl sulphate,
3 parts by weight of polyvinyl alcohol and
7 parts by weight of kaolin, grinding the mixture in a pinned-disk mill, and granulating the powder in a fluidized bed by spray application of water as a granulating liquid.
f) Water-dispersible granules are also obtained by homogenizing and precomminuting
25 parts by weight of a compound of the formula (I),
5 parts by weight of sodium 2,2'-dinaphthylmethane-6,6'-disulphonate,
2 parts by weight of sodium oleoylmethyltaurinate,
1 part by weight of polyvinyl alcohol,
17 parts by weight of calcium carbonate and
50 parts by weight of water
in a colloid mill, then grinding the mixture in a bead mill and atomizing and drying the resulting suspension in a spray tower by means of a one-phase nozzle.

BIOLOGICAL EXAMPLES

Herbicidal Pre-Emergence Action

Seeds of monocotyledonous and dicotyledonous weed plants and crop plants were placed in wood-fibre pots in sandy loam and covered with soil. The compounds (I) according to the invention, formulated in the form of wettable powders (WP), were then applied as aqueous suspension or emulsion at a water application rate of 600 l/ha (converted) with the addition of 0.2% of wetting agent to the surface of the covering soil.

After the treatment, the pots were placed in a greenhouse and kept under good growth conditions for the test plants. After about 3 weeks, the effect was scored visually in comparison with untreated controls as percentages. For example, 100% activity=the plants have died, 50% herbicidal activity or damage=the plants have been reduced by 50% or the plant mass has been reduced by 50%, 0% activity=like control plants.

Herbicidal Post-Emergence Action

Seeds of monocotyledonous and dicotyledonous weeds and crop plants were placed in sandy loam in wood-fibre pots, covered with soil and cultivated in a greenhouse under good growth conditions. 2 to 3 weeks after sowing, the test plants were treated at the one-leaf stage, where the compounds according to the invention, formulated in the form of wettable powders (WP), were applied by spraying as aqueous suspension or emulsion at a water application rate of 600 l/ha (converted) with the addition of 0.2% of wetting agent to the green parts of the plants. After the test plants had been kept in the greenhouse under optimum growth conditions for about 3 weeks, the activity of the preparations was rated visually in comparison to untreated controls in percent (%). For example, 100% activity=the plants have died, 50% herbicidal activity or damage=the plants have been reduced by 50% or the plant mass has been reduced by 50%, 0% activity=like control plants.

The results obtained show that compounds (I) according to the invention and their salts, in particular the compounds according to the invention characterized as preferred, have good to very good herbicidal activity against harmful plants at an application rate of 320 g or less per hectare, generally also even at a respective application rate of 80 g/ha.

The biological tests were carried out in each case separately with the compounds according to the invention below which, by virtue of the good to very good herbicidal activity thereof, are particularly preferred according to the invention: erythro-Iba354, threo-Iba354, threo-2-Iba354, Iba19, threo-1-Iba19, Iba25, threo-1-Iba25, Iba46, erythro-Iba46, threo-1-Iba46, threo-2-Iba46, erythro-1-Iba52, threo-2-Iba52, threo-1-Iba52, Iba24, threo-1-Iba24, Iba181, Iba937, Ibb19, Ibe19, Ibv19, Ibb46, Ibe46, Ibv46, Ibb52, Ibe52, Ibv52, Iba51, threo-1-Iba51, Iba26, threo-1-Iba26, threo-2-Iba26, Iba53, erythro-1-Iba53, threo-1-Iba53, threo-2-Iba53, Iba370, Iba5, Iba154, Iba30, Iba161, Ibh53, Iba57, Iba138, Ibx53, Ibw53, Ibw26, Iby53, Ibh26, Ibh25, Iba80, Ibb30, Ibe30, Iby26, Iby25, Iby52, Iba235, Iba242, Iba1, Ibb73, Iba140, Iba59, Ibc19, Ibx19, Ibh289, Ibb79, Iba532, Iba64, Iba327, Iba275, Iba289 and Iba221.

The biological tests were furthermore carried out in each case separately with the compounds according to the invention below which, by virtue of the good to very good herbicidal activity thereof, are likewise particularly preferred according to the invention:
erythro-1-Iba106, erythro-1-Iba134, erythro-1-Iba28, erythro-1-Iba5, erythro-2-Iba111, erythro-2-Iba28, erythro-2-Iba3, erythro-2-Iba30, erythro-2-Iba52, erythro-2-Iba53, Iba10, Iba100, Iba1056, Iba1058, Iba106, Iba107, Iba1072, Iba108, Iba1085, Iba111, Iba113, Iba127, Iba13, Iba134, Iba136, Iba15, Iba160, Iba163, Iba165, Iba166, Iba167, Iba169, Iba184, Iba188, Iba189, Iba192, Iba2, Iba22, Iba241, Iba246, Iba262, Iba268, Iba269, Iba27, Iba28, Iba3, Iba31, Iba32, Iba328, Iba33, Iba34, Iba35, Iba352, Iba37, Iba40, Iba42, Iba424, Iba431, Iba49, Iba50, Iba516, Iba538, Iba539, Iba54, Iba55, Iba6, Iba60, Iba61, Iba67, Iba7, Iba70, Iba73, Iba76, Iba77, Iba78, Iba79, Iba81, Iba84, Iba85, Iba86, Iba87, Iba88, Iba94, Iba96, Iba97, Ibb1, erythro-2-Iba354, erythro-2-Iba355, erythro-Iba1099, erythro-Iba59, erythro-Iba79, erythro-Iba80, threo-1-Iba1, threo-1-Iba10, threo-1-Iba100, threo-1-Iba107, threo-1-Iba1085, threo-1-Iba1099, threo-1-Iba1106, threo-1-Iba111, threo-1-Iba113, threo-1-Iba127, threo-1-Iba134, threo-1-Iba138, threo-1-Iba154, threo-1-Iba160, threo-1-Iba161, threo-1-Iba165, threo-1-Iba181, threo-1-Iba187, threo-1-Iba188, threo-1-Iba19, threo-1-Iba192, threo-1-Iba20, threo-1-Iba208, threo-1-Iba214, threo-1-Iba215, threo-1-Iba235, threo-1-Iba241, threo-1-Iba242, threo-1-Iba28, threo-1-Iba3, threo-1-Iba30, threo-1-Iba32, threo-1-Iba355, threo-1-Iba37, threo-1-Iba47, threo-1-Iba532, threo-1-Iba539, threo-1-Iba55, threo-1-Iba57, threo-1-Iba59, threo-1-Iba73, threo-1-Iba79, threo-1-Iba80, threo-1-Iba84, threo-1-Iba86, threo-1-Ibo46, threo-2-Iba1085, threo-2-Iba1099, threo-2-Iba127, threo-2-Iba241, threo-2-Iba355, threo-2-Iba57, threo-2-Iba59, threo-2-Iba73, threo-2-Ibo46, erythro-2-Ibaf46, erythro-2-Ibag325, erythro-2-Ibah19, erythro-2-Ibah325, erythro-2-Ibah73, erythro-2-Ibb100, erythro-2-Ibh19, erythro-2-Ibo46, Ibab190, Ibb289, Ibh52, Ibw25, erythro-Ibg26, threo-1-Ibab19, threo-1-Ibab46, threo-1-Ibab73, threo-1-Ibac19, threo-1-Ibac26, threo-1-Ibac46, threo-1-Ibac53, threo-1-Ibad19, threo-1-Ibad26, threo-1-Ibad46, threo-1-Ibad53, threo-1-Ibae19, threo-1-Ibaf46, threo-1-Ibaf73, threo-1-Ibag26, threo-1-Ibag325, threo-1-Ibag73, threo-1-Ibah19, threo-1-Ibah26, threo-1-Ibah325, threo-1-Ibah73, threo-1-Ibb1, threo-1-Ibb100, threo-1-Ibb19, threo-1-Ibg235, threo-1-Ibg26, threo-1-Ibg35, threo-1-Ibh19, threo-1-Ibo19, threo-1-Ibs46, threo-1-Ibv19, threo-2-Ibab19, threo-2-Ibab46, threo-2-Ibab73, threo-2-Ibad53, threo-2-Ibb19, threo-2-Ibg26 and threo-2-Ibs46.

Here, these compounds according to the invention were in each case employed in the biological tests as a component of a wettable powder (WP formulation).

At an application rate of 320 g/ha, all the compounds according to the invention mentioned showed 80% to 100% herbicidal activity in the biological tests, against one, more than one or all of the harmful plants below:

ALOMY=*Alopecurus myosuroides*
AVEFA=*Avena fatua*
CYPES=*Cyperus esculentus*
ECHCG=*Echinochloa crus-galli*
LOLMU=*Lolium multiflorum*
SETVI=*Setaria viridis*
ABUTH=*Abutilon theophrasti*
AMARE=*Amaranthus retroflexus*
MATIN=*Matricaria inodora* (=*Tripleurospermum maritimum* subsp. *inodorum*)
POLCO=*Polygonum convolvulus* (=*Fallopia convolvulus*)
STEME=*Stellaria media*
VIOTR=*Viola tricolor*
VERPE=*Veronica persica*

What was determined was the respective herbicidal activity, in each case at the same point in time after application of the formulation in question. i.e. the damage to the respective harmful plant in %.

The compounds according to the invention displayed particularly good herbicidal activity against ALOMY=*Alopecurus myosuroides*, ECHCG=*Echinochloa crus-galli*, LOLMU=*Lolium multiflorum*, SETVI=*Setaria viridis*, STEME=*Stellaria media*, VIOTR=*Viola tricolor* and VERPE=*Veronica persica*.

At an application rate of 320 g/ha, the compounds threo-1-Iba354 and Ibb52 additionally displayed 80% and 100% herbicidal activity, respectively, against PHBPU=*Pharbitis purpurea*.

Furthermore, the compounds according to the invention mentioned above were applied to the following useful plants, in each case at the application rates mentioned.
ORYSA=*Oryza sativa* (common rice)
TRZAS=*Triticum aestivum* (spring) (summer wheat)
ZEAMX=*Zea mays* (maize)
BRSNW=*Brassica napus* subsp. *napus* (winter) (winter oilseed rape)

Here, the observed damage to the respective useful plants was within the acceptable range and was generally assessed as low (generally in a range from 0 to 20%).

The invention claimed is:

1. A compound of formula (Ib) and/or a salt and/or ester thereof,

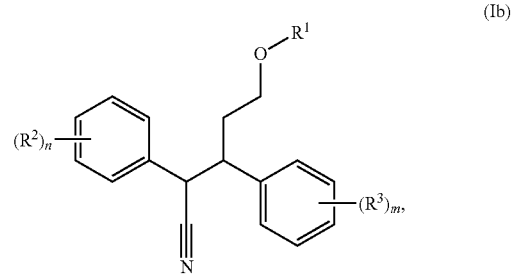

(Ib)

wherein
$R^1$ represents —C(=O)—O—$R^C$ or —C(=O)—$R^C$, where $R^C$ is in each case selected from the group consisting of:
(i) unsubstituted ($C_1$-$C_6$)-alkyl, unsubstituted ($C_2$-$C_6$)-alkenyl, unsubstituted ($C_2$-$C_6$)-alkynyl, substituted ($C_1$-$C_6$)-alkyl, substituted ($C_2$-$C_6$)-alkenyl and substituted ($C_2$-$C_6$)-alkynyl, where each of these substituted radicals is substituted by one or more radicals from the group consisting of methyl, hydroxyl, fluorine and chlorine,
(ii) ($C_3$-$C_6$)-cycloalkyl, ($C_3$-$C_6$)-cycloalkyloxy-($C_1$-$C_4$)-alkyl, phenyl, where each of these radicals is unsubstituted in the cyclic moiety or substituted by one or more identical or different radicals $R^B$, where $R^B$ is independently of any other radicals $R^B$ present selected from the group consisting of halogen (optionally fluorine, chlorine, bromine), cyano, nitro and ($C_1$-$C_4$)-alkyl (optionally methyl),
where $R^C$ optionally comprises a total of 1 to 12 carbon atoms, optionally a total of 1 to 10 carbon atoms,
$R^2$ represents 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-$CF_3$, 3-$CF_3$, 4-$CF_3$, 2-methoxy, 3-methoxy, 4-methoxy, 2-ethoxy, 3-ethoxy, 4-ethoxy, 2-methylthio, 3-methylthio, 4-methylthio, 2-methylsulphinyl, 3-methylsulphinyl, 4-methylsulphinyl, 2-methylsulphonyl, 3-methylsulphonyl, 4-methylsulphonyl, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-3-F), (3-Br-4-F), (3-Br-5-F), (4-Br-3-Cl), (3-Br-4-Cl), (4-CN-3-F), (3-CN-4-F), (3-CN-5-F), (4-CN-3-Cl), (3-CN-4-Cl), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or (2,6-$F_2$-4-Cl), and $R^3$ represents 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-CF, 2-methoxy, 3-methoxy, 2-ethoxy, 3-ethoxy, 4-ethoxy, 2-methylthio, 3-methylthio, 4-methylthio, 2-methylsulphinyl, 3-methylsulphinyl, 4-methylsulphinyl, 2-methylsulphonyl, 3-methylsulphonyl, 4-methylsulphonyl, 2-nitro, 3-nitro, 4-nitro, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, 2,5-dicyano, 2,6-dicyano, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-2-F), (4-Br-3-F), (4-CN-3-F), (4-$NO_2$-3-F), (4-OMe-3-F), (3-CN-4-F), (3-$NO_2$-4-F), (3-CN-4-Cl), (3-$NO_2$-4-Cl), (5-CN-2-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or (2,6-$F_2$-4-Cl), m represents 1, 2, or 3 and n represents 1, 2, or 3.

2. The compound of formula (Ib) of claim 1 and/or a salt and/or ester thereof, wherein m represents 0, and n represents 0.

3. The compound of formula (Ib) of claim 1 and/or a salt and/or ester thereof, wherein m represents 1, 2, or 3 and n represents 1, 2, or 3.

4. Herbicidal or plant growth-regulating composition, comprising one or more compounds of formula (Ib) and/or salt thereof as defined in claim 1 and one or more further substances selected from groups (i) and/or (ii):

(i) one or more further agrochemically active substances, selected from one or more of the group consisting of insecticides, acaricides, nematicides, further herbicides, fungicides, safeners, fertilizers and further growth regulators, (ii) one or more formulation auxiliaries customary in crop protection.

5. The composition of claim 4, wherein m represents 0, and n represents 0.

6. The composition of claim 4, wherein m represents 1, 2, or 3 and n represents 1, 2, or 3.

7. Method for controlling broad-leaved weeds and/or weed grasses and/or sedge weeds or for regulating plant growth in crops of useful plants, comprising applying an effective amount of one or more compounds of formula (Ib) and/or a salt thereof, as defined in claim 1.

* * * * *